(12) United States Patent
Hui

(10) Patent No.: US 7,329,422 B2
(45) Date of Patent: Feb. 12, 2008

(54) PHARMACEUTICAL COMPOSITIONS

(76) Inventor: Kam Man Hui, 66 Trevose Cresent, No. 04-08, 298067 Singapore (SG)

( * ) Notice: Subject to any disclaimer, the term of this patent is extended or adjusted under 35 U.S.C. 154(b) by 0 days.

(21) Appl. No.: 10/517,596

(22) PCT Filed: Jun. 12, 2003

(86) PCT No.: PCT/GB03/02595

§ 371 (c)(1), (2), (4) Date: Sep. 29, 2005

(87) PCT Pub. No.: WO03/105877

PCT Pub. Date: Dec. 24, 2003

(65) Prior Publication Data

US 2006/0165825 A1    Jul. 27, 2006

(30) Foreign Application Priority Data

Jun. 12, 2002 (GB) ................................. 0213481.5

(51) Int. Cl.
*A61K 36/70* (2006.01)
(52) U.S. Cl. ..................................... 424/750; 424/773

(58) Field of Classification Search ..................... None
See application file for complete search history.

(56) References Cited

U.S. PATENT DOCUMENTS

2001/0018076 A1*    8/2001    Han et al. ................... 424/725

OTHER PUBLICATIONS www.cnn.com/HEALTH/library/CA/00024.html—accessed Jul. 21, 2006.*
www.webmd.com/hw/rheumatoid_arthritis/aa19581.asp—accessed Nov. 2, 2006.*
Liu et al. (Zhongguo Yaolixue Tongbao (1998), vol. 14, No. 1, pp. 36-9).*

* cited by examiner

*Primary Examiner*—Susan Coe Hoffman
(74) *Attorney, Agent, or Firm*—B. Aaron Schulman; Stites & Harbison PLLC

(57) ABSTRACT

Compositions have been obtained by extracting rhizomes of *Fagopyrum dibotrys* with alcohol and concentrating the extract to a powder or syrup, optionally followed by fractionation. The extract is demonstrated to be a potent anticancer agent. Its activity at the gene level was analysed.

5 Claims, 10 Drawing Sheets

(1)

PHARMACEUTICAL COMPOSITIONS

TECHNICAL FIELD

The present invention concerns compounds and compositions which are therapeutically active, e.g. against some types of cancer. Thus it provides compounds, compositions, methods of manufacturing compositions and methods of treatment. It is primarily concerned with pharmaceuticals derived from *Fagopyrum dibotrys* (or *Fagopyrum cymosum meisen*) (golden buckwheat; jinqiaomai).

BACKGROUND ART

*Fagopyrum dibotrys* is one of the innumerable plants used in Chinese traditional medicine. The whole plant, particularly the rhizome, is used as a medicament, allegedly having a wide range of beneficial effects, including antitumour activity.

Zhang Wen-Jie et al., *Acta Botanica Yunnanica*, 1994, 16, 354-356 separated and identified a number of phenolic constituents. The compound obtained in highest yield (0.19%) was termed procyanidin B-2 and was assigned the formula (1) (see FIG. 1). This compound has 5 asymmetric centres (asterisked in FIG. 1), so potentially there are 32 stereoisomers. No information is available about which isomer(s) is/are present in the isolated material. They are 5,7,3',4'-tetrahydroxy flavon-3-1 $C_4$-$C_8$ dimers. Such a dimer or dimers was previously isolated from avocado seed (T. A. Geissmann et al. *Phytochem.*, 1965, 4, 359-368).

DISCLOSURE OF INVENTION

We have now investigated materials derived from rhizomes of *Fagopyrum dibotrys* and have demonstrated remarkable and wholly unexpected levels of activity, notably against a number of cancers. Thus in various aspects the invention provides:

(a) the use of rhizomes of *Fagopyrum dibotrys* in the manufacture of a medicament for use in the treatment of cancer;

(b) the use of procyanidin B-2 as isolated from *Fagopyrum dibotrys* in the manufacture of a medicament for use in the treatment of cancer;

(c) the use of a compound of formula (1) in the manufacture of a medicament for use in the treatment of cancer;

(d) a process of producing a composition derived from rhizomes of *Fagopyrum dibotrys* suitable for use in cancer therapy;

(e) a method of cancer therapy comprising administration of a medicament which is a composition derived from rhyiomes of *Fagopyrum dibotrys* or procyanidin B-2 as isolated from *Fagopyrum dibotrys*.

Material can be obtained from plant material by extraction with a lower ($C_1$-$C_4$) alcohol, preferably ethanol or methanol. This extract can be further purified by solvent extraction etc and by chromatography.

The material obtained from the plant or a compound isolated therefrom may be formulated in various ways for use in therapy. Conditions which may be treated include, for example, neoplastic diseases, particularly lung cancer and breast cancer. In accordance with this aspect of the present invention, the compounds provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated.

Pharmaceutical compositions according to the present invention, and for use in accordance with the present invention, may comprise, in addition to the active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

MODES FOR CARRYING OUT THE INVENTION

Production of Extract

Method A

Figure 1:
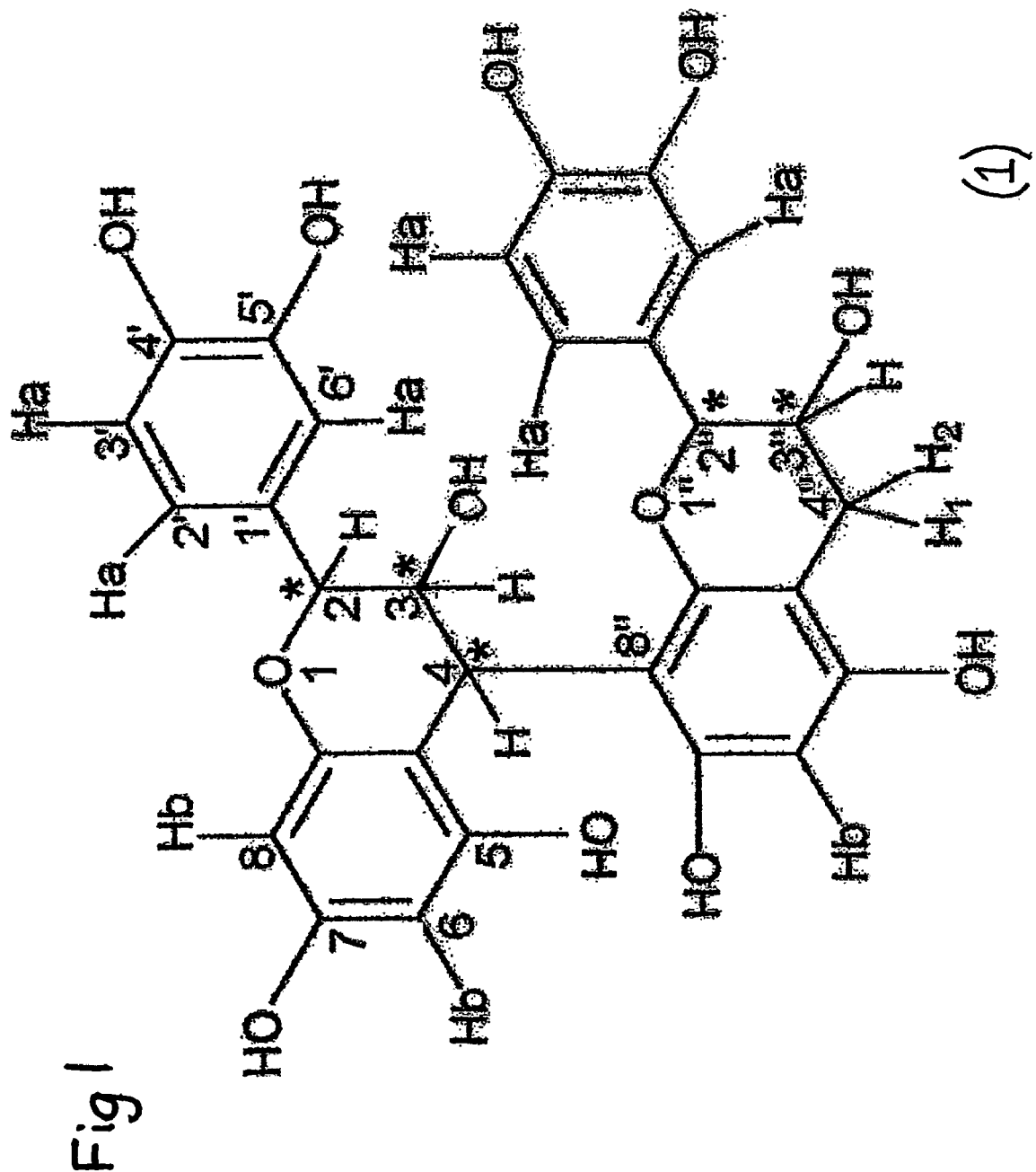
FIG. 1 shows the formula of procyanidin B-2.

Samples of *Fagopyrum dibotrys* were obtained from parts of China: Yun Nan Province; Long Quan District of Sichuan Province, Liang Shan District of Sichuan Province, and Chong Qing County of Sichuan Province. The material from Liang Shan appeared to be of the best quality and analysis showed it had by far the highest content of ketones (7.65% by weight), and a significantly higher tannin content (2.90% by weight). Therefore this material was used for further study.

*Fagopyrum dibotrys* rhizomes were broken into small particles, and 2400 kg of this particulate material was extracted with 70% ethanol 12 times using a total of 28,800 kg. The extract was concentrated by evaporation to give 1896 litres, 2184 kg. Half of this concentrate was further concentrated by evaporation under reduced pressure, which gave 278 kg of syrup. The other part was spray dried, which gave dry powder (80 kg). The syrup could be converted into a dry solid by heating in an oven. The solid could then be powdered.

The powder (spray or oven dried) contained 4.63% water, 35.35% ketones and 46.62% tannins, all by weight.

Method B

This is the result of further work on the development of a pilot plant.

1. Pre-Processing (Done in Sichuan Province, P.R.C)

1.1. Harvest the herb of Rhizoma *Fagopyri Dibotryis*, remove the stem and rootlet, clean and wash, dry at temperature below 60° C. to a moisture content of between 9%~13% (for an actual example, the moisture content was 11.97% prior to extraction).

1.2. Chop the dried clean herb into particulate to achieve the diameter of less than 2 mm.

2. Extraction of Herb 2.1 Using four 50 litre percolators, fill each percolator with 10 kg of the raw material.

2.2 Fill in 180 L 70% ethanol for the first time at 60° C. and the flow rate of 300 L/h. It took 12 h to macerate less than 60° C. Then make a circulation at 60° C. for 0.5 h. After that it took 15 minutes to discharge the liquid extract.

2.3 Fill in 300 L 70% ethanol for the second time at 60° C. and the flow rate of 300 L/h. Then it took 1 h to discharge the liquid extract.

3. Evaporation

Fill the evaporator with liquid extract, condense it at 50~60° C. to the relative density at 1.06~1.10 (50~60° C.). 14.99 kg concentrated extract was obtained and employed for drying.

4. Vacuum Drying

Half of the concentrated extract (7.495 kg), was mixed with 0.565 kg maltodextrin and 0.055 kg colloidal anhydrous silica, then dried at 50~60° C. in the vacuum oven for 6 h to the moisture content of 2.93%. A total of 2.53 kg dry material was obtained of which 20% is 0.506 kg excipient and 80% (2.024 kg) being the dry herbal extract.

Purification of Procyanidin B-2

Powder (2 kg) obtain by Method A was extracted with technical ethanol. After warming at 65° C. for 2 hrs, the solution was filtered. 13.2 g of mixture was obtained after removal of the solvent from the filtrate. The herb was macerated again overnight and warmed for 2 hrs at 65° C. and filtered. 8.2 g of brown residue was obtained from the second filtrate. TLC analysis of the two extractions showed that the constituents of them are essentially the same.

For the purification of Procyanidin B-2 with chromatography, we found that by using ETHYL ACETATE:ACETIC ACID:WATER=450:10:10 as eluent, most of the non-polar components could be removed. Three belts in the column were observed during the washing, the first one is green; the second one is red and the third one is brown. After the brown belt was washed down, Procyanidin B-2 was detected in the fractions collected. The relatively pure fractions were found to be suitable to view the component on TLC board, but not pure enough to run an NMR spectrum.

The detailed purification of Procyanidin B-2 on a column was carried out as follows: 100 g of the crude extract was dissolved in 1 L water with strong stirring. The dark solution was extracted twice with ethyl acetate (2×500 ml). A brown-glass (10.6 g) was obtained after removal of the solvent under vacuum. This step of purification could possibly remove most of the salts from the extraction.

120 g of silica gel was loaded into a column with hexane to reach the length of 60 cm. The brown glass (10.6 g) was dissolved in 15 ml ethyl acetate and added into the column. The column was washed with ETHYL ACETATE:ACETIC ACID:WATER=700:10:10 to get a mixture. In order to recover the silica gel, the column was washed with 500 ml water, followed by 500 ml methanol and then 500 ml ethyl acetate. The mixture obtained from the first run was loaded into this column again and eluted by the same solvent system. However, the fractions collected are still not pure enough. The 3.6 g mixture obtained was a pale yellow glass after being vacuum dried.

The mixture (3.6 g) was purified again by repeating the above mentioned procedures to get 0.29 g Procyanidin B-2. On TLC plate, its purity seems quite good. In its NMR spectrum, we could observe the resonances reported by Zhang et al. (op.cit.) but some impurities which cannot be identified are also present. Its Mass spectrum shows the molecular ion at m/z 577.2 ([M–H]) as the highest peak. Another peak at m/z 289.2 suggests that the fragment is the ion generated by breaking the C4-C8" bond of Procyanidin B-2.

An alternative method to purify Procyanidin B-2 is to elute the column with ethyl acetate/hexane as a gradient solvent system (increasing the volume ratio from 1/1 to 2.5/1) to remove most of the components that are less polar than Procyanidin B-2 (The washing is slow yet efficient). The mixture containing Procyanidin B-2 is collected and purified further with the first method.

The detailed spectroscopic data of Procyanidin B-2 are summarised as follow: UV$\lambda^{MeOH}$ (1 g$\epsilon$): 208(4.96), 281 (3.95); FAB-MS m/z: 577[M–H]$^-$; $^1$H-NMR [(CD$_3$)$_2$CO]; $\delta$2.73(1H, br, J=16.0 Hz), 2.89(1H, dd J=16.0, 4.0 Hz), 3.98 (1H, m), 4.32(1H, m), 4.71(1H, s), 4.98(1H, br), 5.05(1H, br), 5.93-6.03(3H, m), 6.64-6.96(6H, m).

Biological Activity

We have found that material extracted from *Fagopyrum dibotrys* possesses significant anti-tumour activity. In this study, it is named "MPCB". It was found to inhibit the production of matrix metalloproteinases from tumour cells, particularly IV collagenases. We have found that the invasion of B16-BL6 melanoma cells through the basement membrane was inhibited by MPCB in a concentration-dependent manner. We also investigated the therapeutic effects of multiple oral administration of MPCB on mice inoculated with B16-BL6 melanoma cells. The administration of MPCB also significantly reduced the metastasis incidence as compared to untreated controls.

In a phase I study, 11 patients aged 11 to 78 with advanced NSCLC who have failed all conventional chemotherapy were given MPCB in escalated doses. This was in the form of soft-shell capsules containing the plant extract (powder) obtained by Method A above. Capsules were administered orally. The highest dose achieved was 7.2 grams daily (18 capsules, administered in 3 doses at different times) and no significant side-effects were encountered at this dose. Two of the 9 patients had stabilisation of disease, with a median survival of 9.5 months, instead of the expected median survival of 4 to 5 months for the entire group. In addition, the CEA level showed signficant reductions in some of the patients. In fact, there was significant reduction in tumour mass on CT scan evaluation of one of the patient.

Figure 2A:
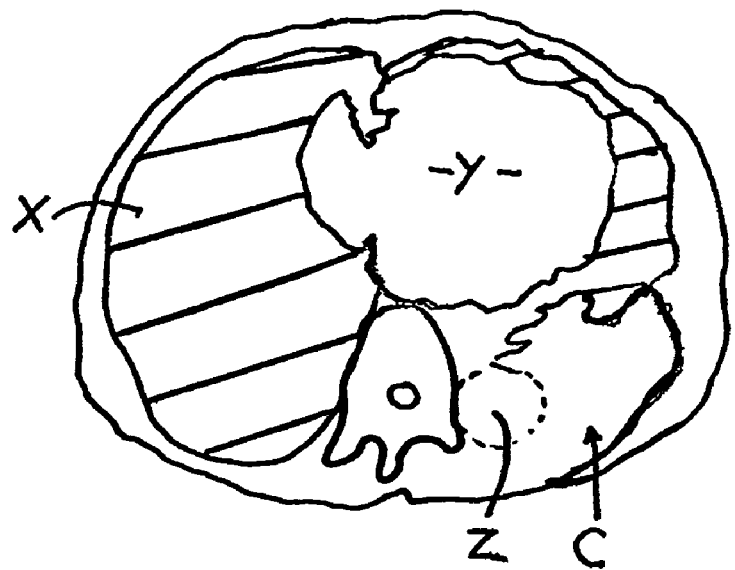
FIGS. 2A and B are drawings of CT scans of a patient taken 3 months apart.
Figure 2B:
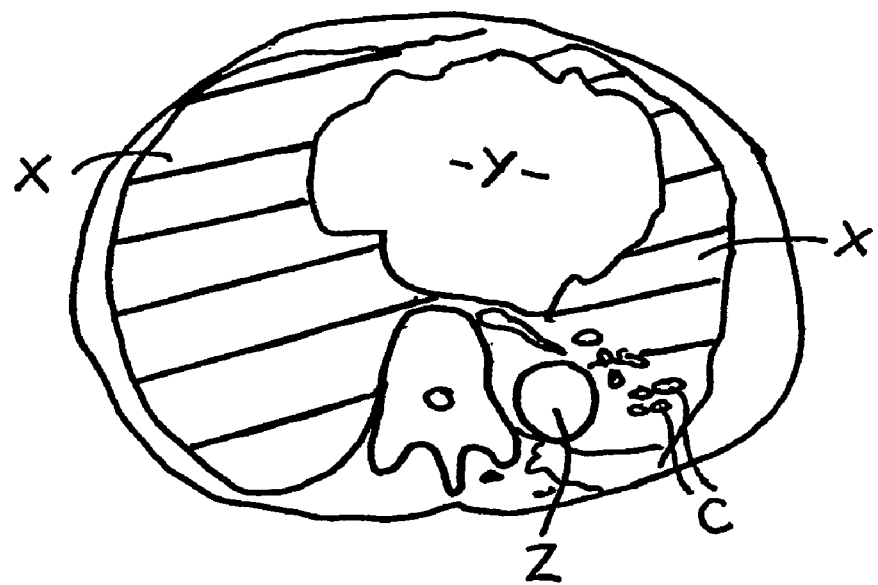

FIGS. 2 A and B show CT scans of the patient taken 3 months apart. X indicates a lung, Y indicates the heart and Z indicates the aorta. The cancerous growth (lung cancer) is the unshaded area indicated by the arrow C. It can be seen that it is much reduced in the second scan.

In an acute toxic test of the drug on mice, the calculated LD50 is 61 g/kg; 95% confidence interval 48.73 g/kg to 77.02 g/kg. According to the standard physiology index ratio between mouse and human beings, the calculated LD50 is 183.78 g/man (60 kg); 95% confidence interval 146.19 to 213.06 g/man. Based on this result, the dosage of log/day is only 5.4% of the LD dosage. In addition, it was demonstrated that at low doses, as used in this study, indices such as WBC, Platelet, RBC, RDW and MCHC did not display significant changes. A sample of the drug was submitted to the Health Sciences Authority for analysis and no significant toxic compounds such as heavy metals were detected. The method of extraction and processing of the herb has received certification from the Sichuan Health Authorities.

Test were made of the purified B-2 compound on human breast cancer cells grown in tissue culture. A marked reduction in the number of cells in the treated samples was apparent.

The experiment was repeated using human liver cancer cells. Once again it was visually evident that the number of cancer cells was substantially reduced by the drug.

Tumour-Preventive Effects of MPCB

An ethanol extract prepared using the extract prepared by Method B was employed. The dried extract contained 20% excipients. It was ground, sieved, weighed and suspended in water with the final concentration of 0.20 g/ml (inclusive of excipients).

For in vivo experiments, 4-6 weeks female SCID mice weighing 15±4 g were used. 12 SCID mice, the control group, were given distilled water while 12 SCID mice in the test group were given 1.45 g/kg of the herbal extract per day. These mice were fed orally with 1.45 g/kg of the extract from day 0 to day 21.

At day 22, all mice were given a tumor challenge of $1\times10^6$ (200 µl of $5\times10^6$ cells/ml) of the human A549 lung cancer cells. The incidence of tumor take in these mice was followed.

Figure 3:
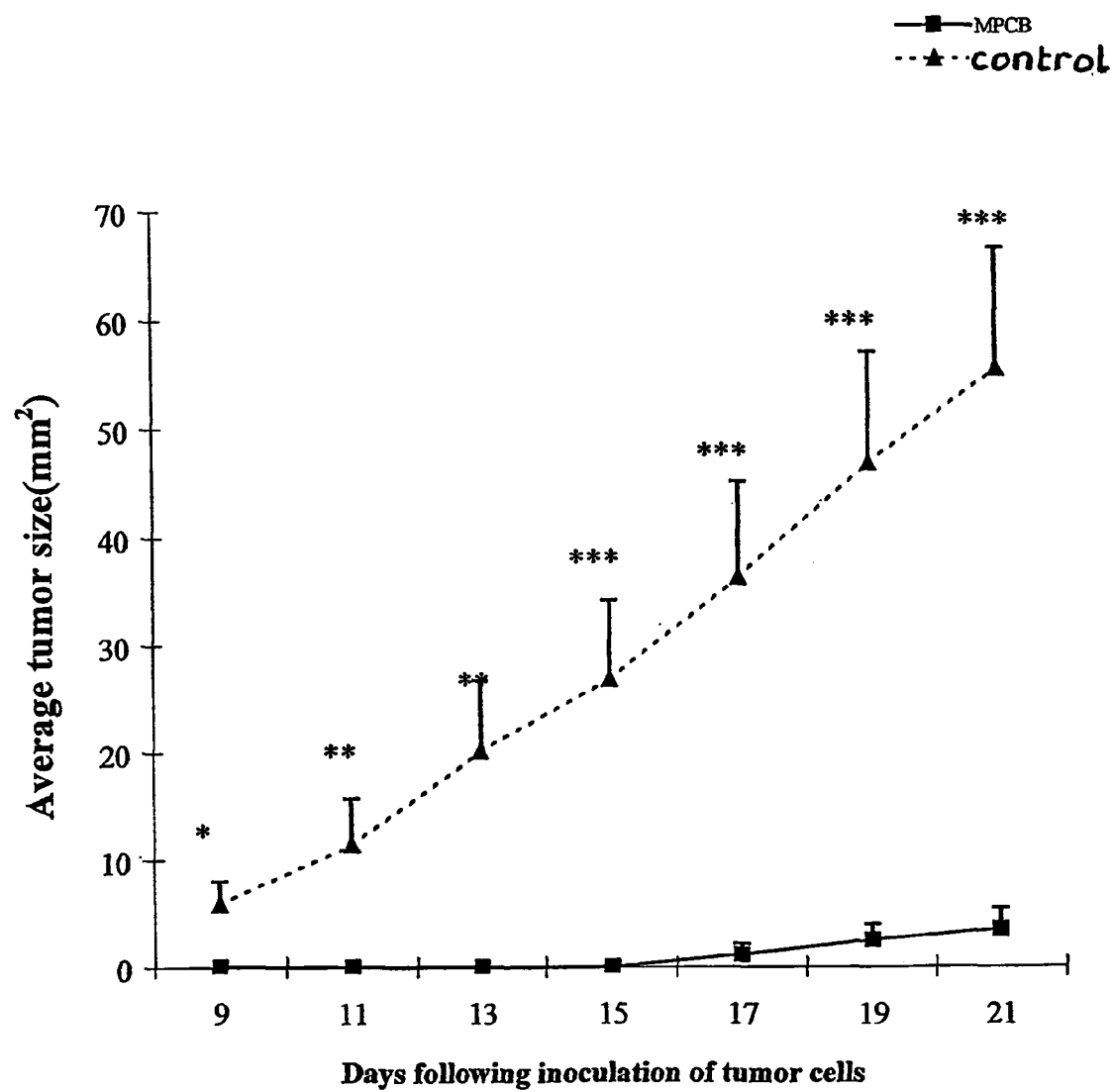
FIG. 3 is a graph showing activity in preventing the development of lung cancer.

Following the injection of the A549 cancer cells and till the end of the experiment, no behavioral and physiological abnormality was observed in both control and experimental groups. No mouse died during the experiment period. It was noted that all the SCID mice in the control group developed tumor. In comparison, only two out of twelve mice in the test group developed tumor (see graph, FIG. 3). In addition, the sizes of tumor of these two mice were much smaller than that of the mice in the control group (see graph below). The other 10 mice in the test group showed no sign of tumor.

Hence, we concluded that the ethanol extract of MPCB could prevent and retard the development of tumor.

Figure 4:
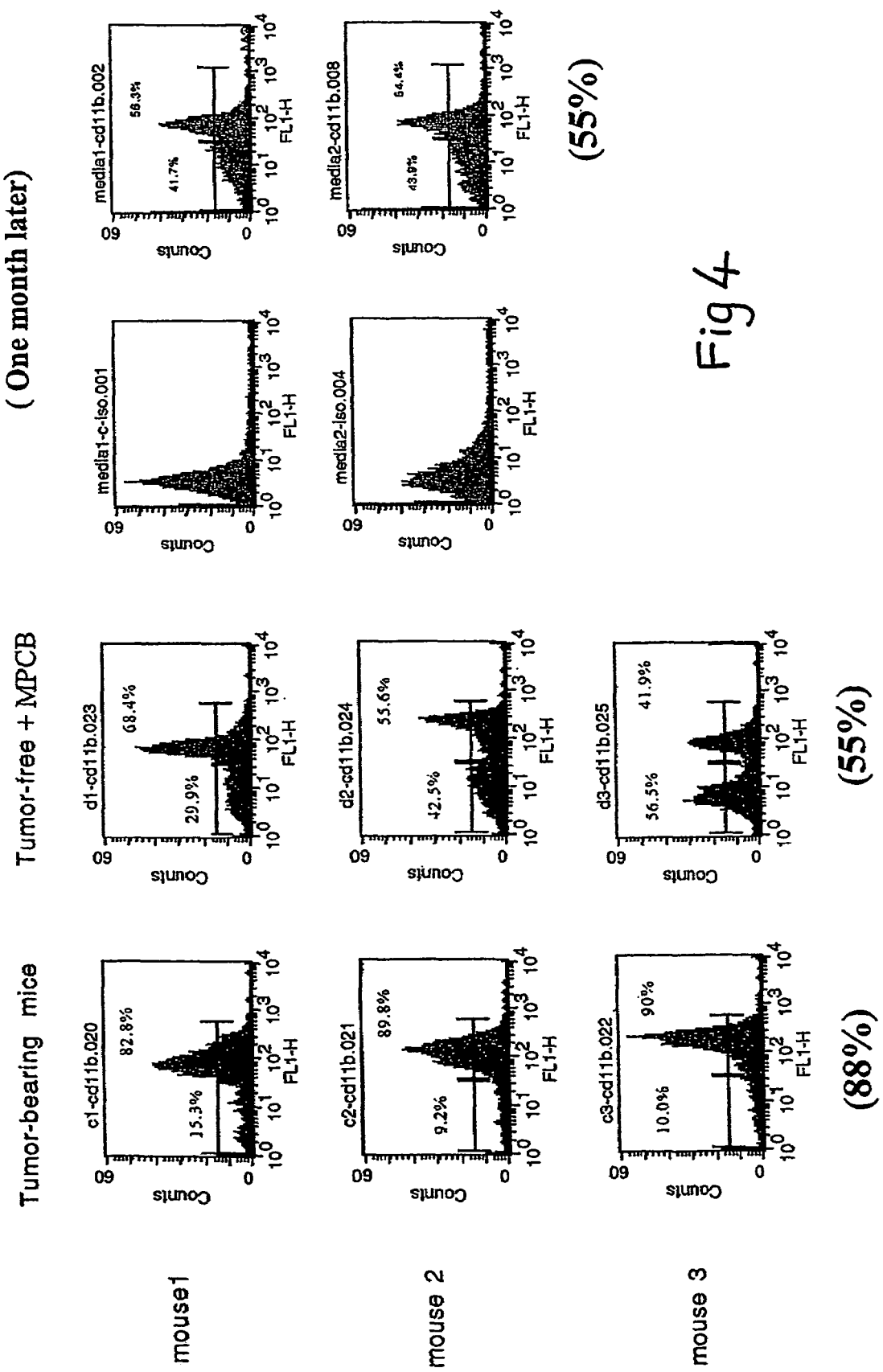
FIG. 4 shows the results of flow cytometry experiments relating to anti-CD11b (cell surface marker for monocytes).

The resistant to the development of cancer in SCID mice given MPCB is correlated with the reduction in $CD11b^+$ cells (see FIG. 4). $CD11b^+$ cells are known to produce peroxide radicals that associate with tumor promotion. Hence, the reduction in $CD11b^+$ cells would support the observation that MPCB could prevent the development of human cancer in SCID mice. This effect is long lasting and the reduction in the $CD11b^+$ cells could be demonstrated one month after the mice are no longer given MPCB.

Since MPCB can drastically decrease the number of monocytes, it is clear that it will be beneficial towards diseases resulting from or associated with inflammation.

Therapeutic Activity Against Breast Cancer $1\times10^7$ human MDA-231 breast cancer cells (200 µl of $2.5\times10^7$ cells/ml) were inoculated subcutaneously into 48 female SCID mice (4-6 weeks old, weight 15±4 g). In 8-14 days, the sizes of the tumor of the recipient mice ranged from 0.3-0.5 cm in diameter (when determined by vernier calipers). At this time, the mice were divided into four treatment groups as follows:

12 SCID mice were given distilled water (control group);

12 SCID mice were given 1.45 g/kg (⅕ $LD_{50}$) of the MPCB extract (Test group 1);

12 SCID mice-were given 0.84 g/kg of the MPCB extract (Test group 2);

12 SCID mice were given 0.39 g/kg of the MPCB extract (Test group 3).

MPCB herbal-extract as used in the preceding experiment (aqueous suspension, 0.20 g/ml) was administrated orally to the SCID mice and the development of tumor was recorded.

Following the injection of the MDA-231 human breast cancer cells till the end of the experiment, no behavioral and physiological abnormality was observed in both the control and test groups.

Figure 5:
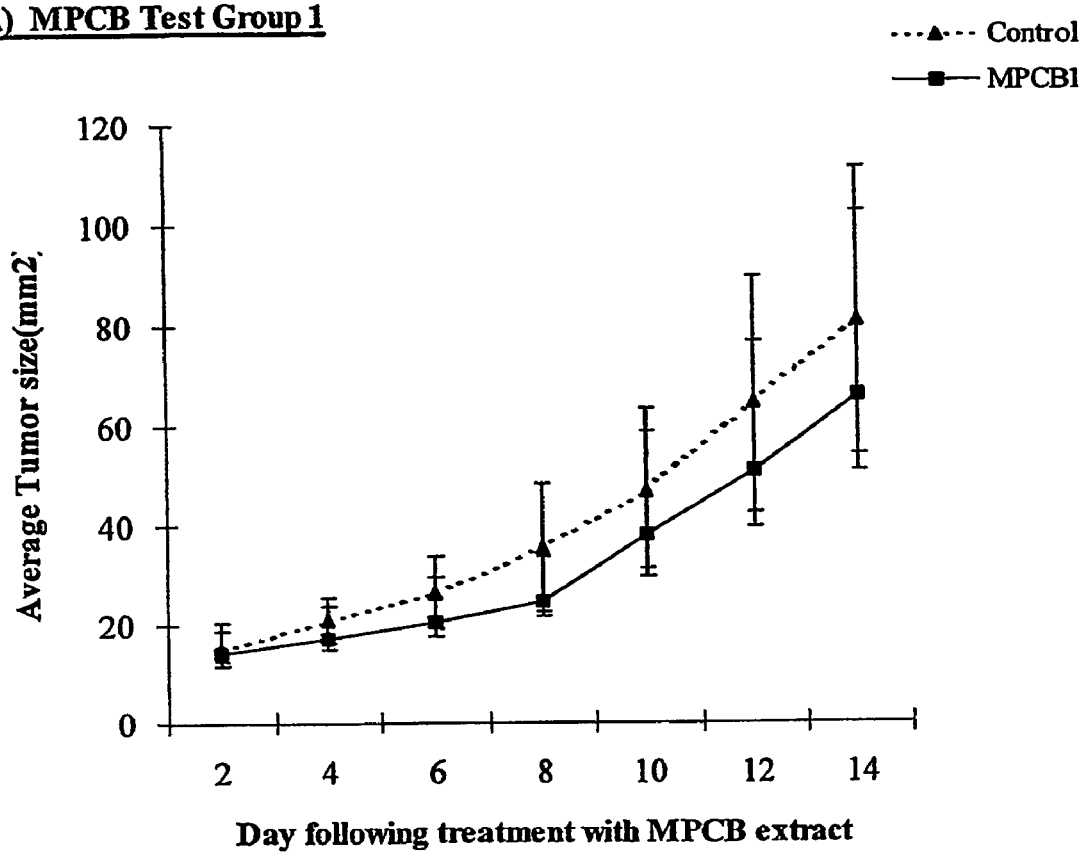
FIGS. 5-7 are graphs showing activity against breast cancer.
Figure 6:
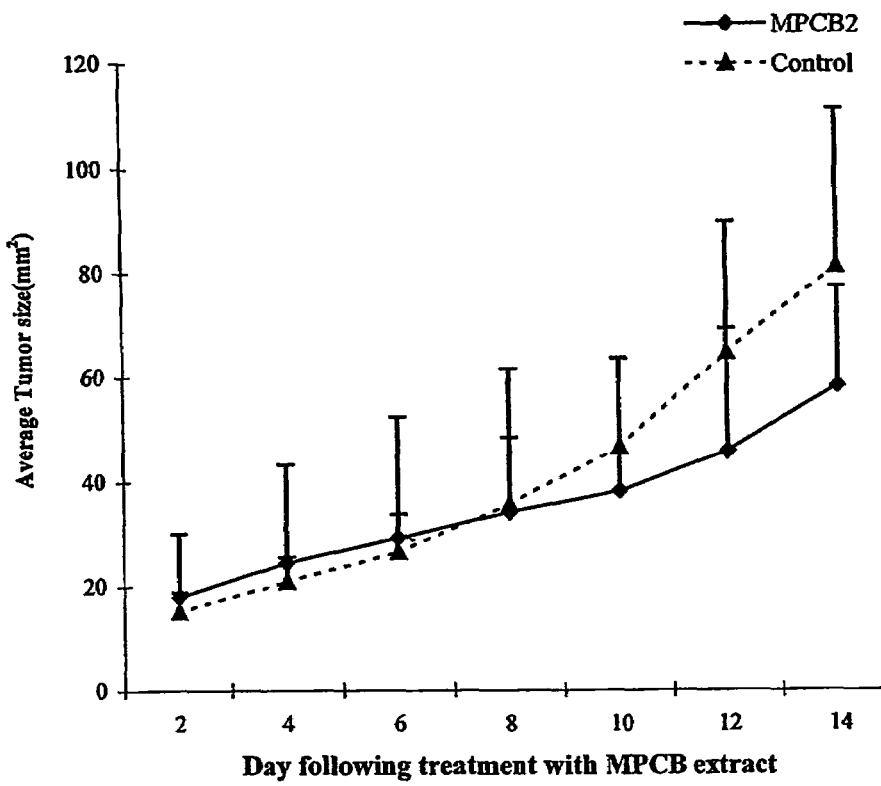
Figure 7:
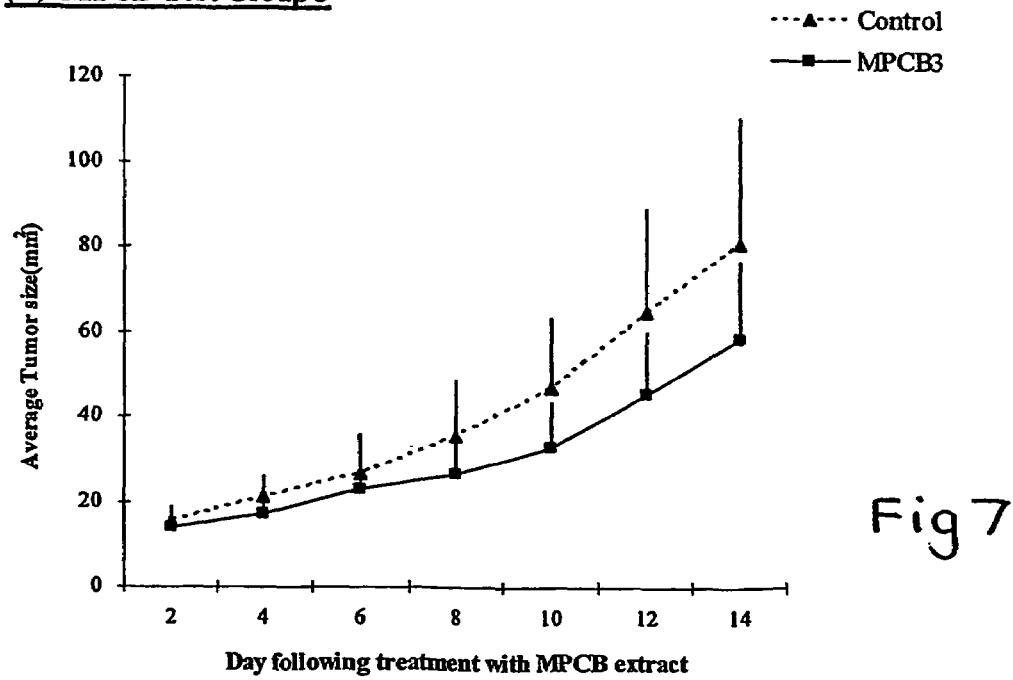

It was observed that in comparison to the control group of which the tumor developed progressively, tumor growth in all the three test groups of which the tumor-bearing SCID mice were-given the MPCB extract, the rate of tumor growth was much reduced. The data are presented in FIGS. 5-7. Hence, it was therefore concluded that MPCB has a therapeutic effect towards the growth of human breast cancer in the SCID mice model.

Therapeutic Activity Against Lung Cancer $1\times10^6$ human A549 lung cancer cells (200 µl of $5\times10^6$ cells/ml) were inoculated subcutaneously into 48 female SCID mice (4-6 weeks old, weight 15±4 g). In 8-14 days, the sizes of the tumor of the recipient mice ranged from 0.3-0.5 cm in diameter (when determined by vernier calipers). At this time, the mice were divided into four treatment groups as follows:

12 SCID mice were given distilled water (control group);

12 SCID mice were given 1.45 g/kg (⅕ $LD_{50}$) of the MPCB extract (Test group 1);

12 SCID mice were given 0.84 g/kg of the MPCB extract (Test group 2);

12 SCID mice were given 0.39 g/kg of the MPCB extract (Test group 3).

MPCB herbal extract as used in the previous experiments (aqueous suspension, 0.20 g/ml) was administrated orally to the SCID mice and the development of tumor was recorded.

Following the injection of the A549 human lung cancer cells till the end of the experiment, no behavioral and physiological abnormality was observed in both the control and test groups.

Figure 8:
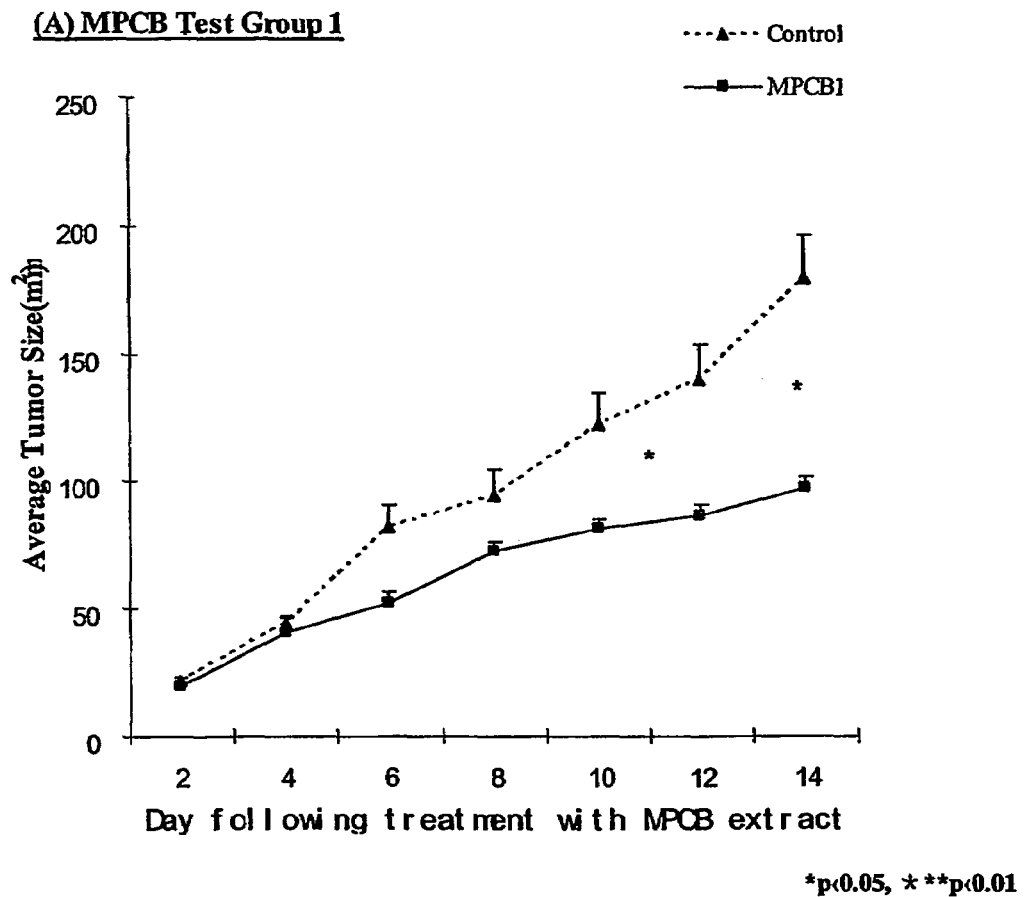
FIGS. 8-10 are graphs showing activity against lung cancer.
Figure 9:
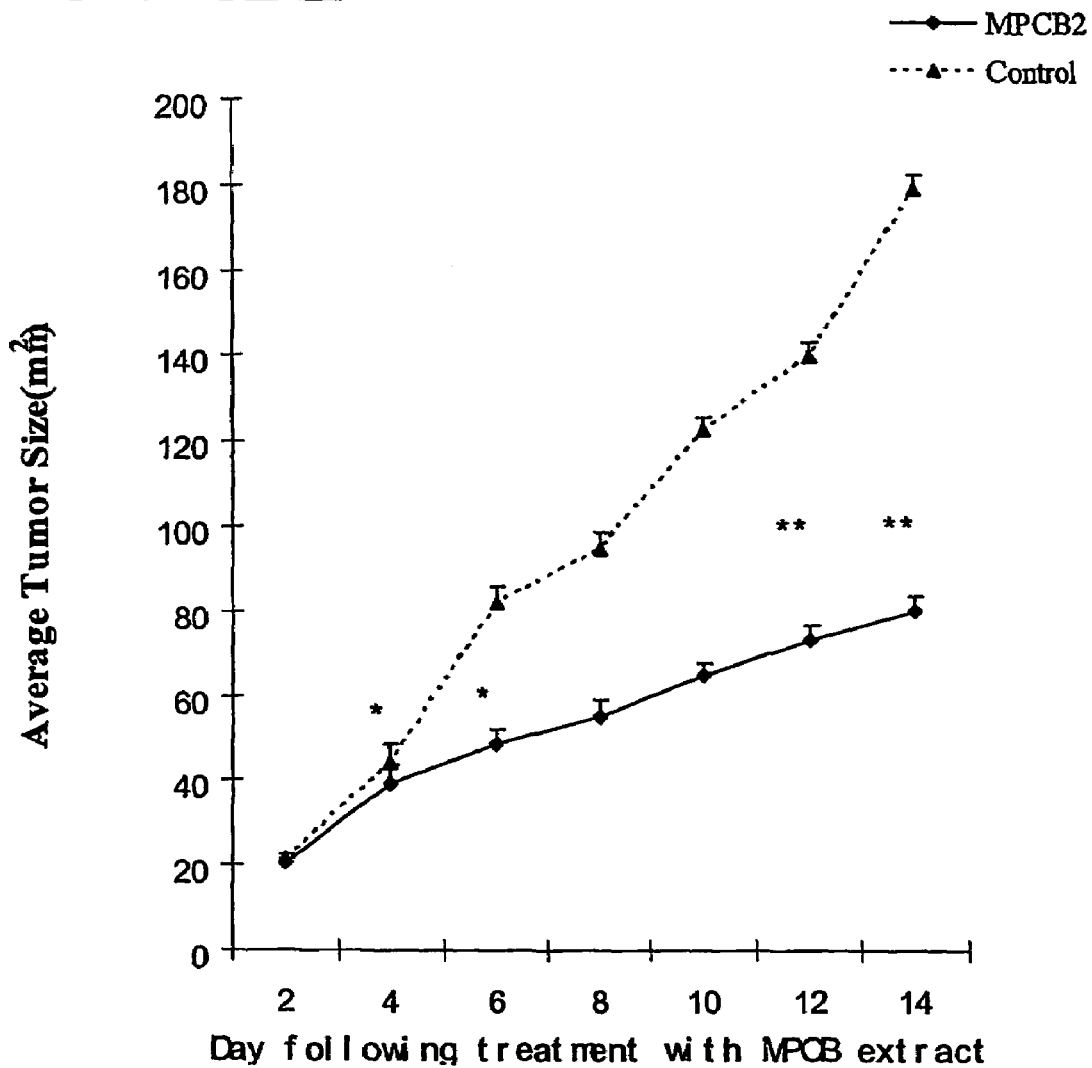
Figure 10:
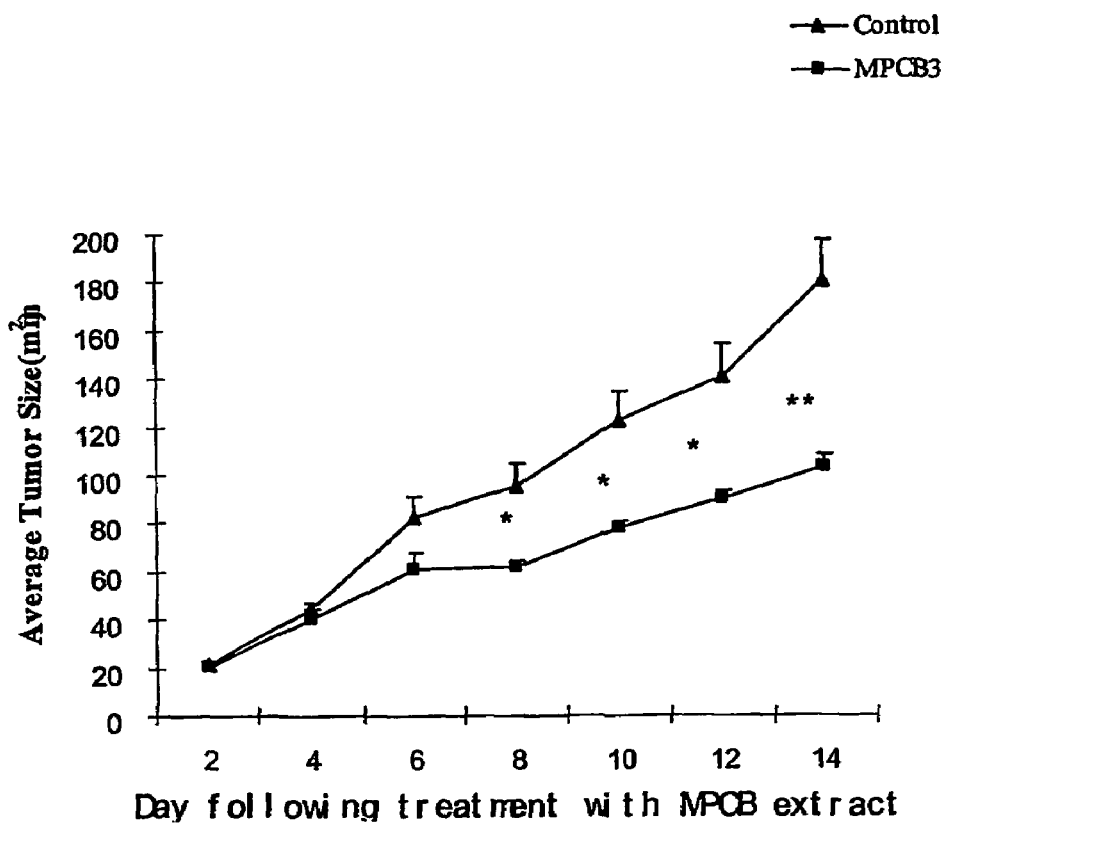

It was observed that in comparison to the control group of which the tumor developed progressively, tumor growth in all the three test groups of which the tumor-bearing SCID mice were given the MPCB extract, the rate of tumor growth was much reduced (see FIGS. 8-10). Hence, it was therefore concluded that MPCB has a therapeutic effect towards the growth of human lung cancer in the SCID mice model.

Gene Activity

The mechanism of action at the gene level was investigated using Affymetrix gene chips. Tables 1-4 list genes up-regulated at days 2 and 5, and down-regulated at days 2 and 5.

Figure 11:
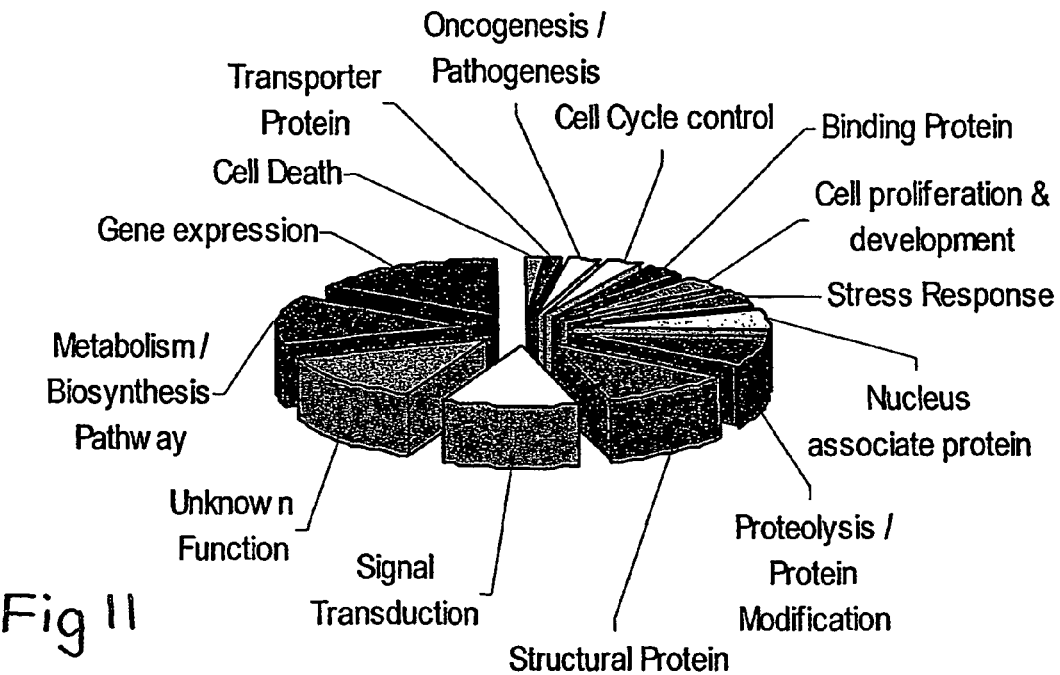
FIGS. 11 and 12 are pie charts giving a functional breakdown of up-regulated and down-regulated genes, respectively.
Figure 12:
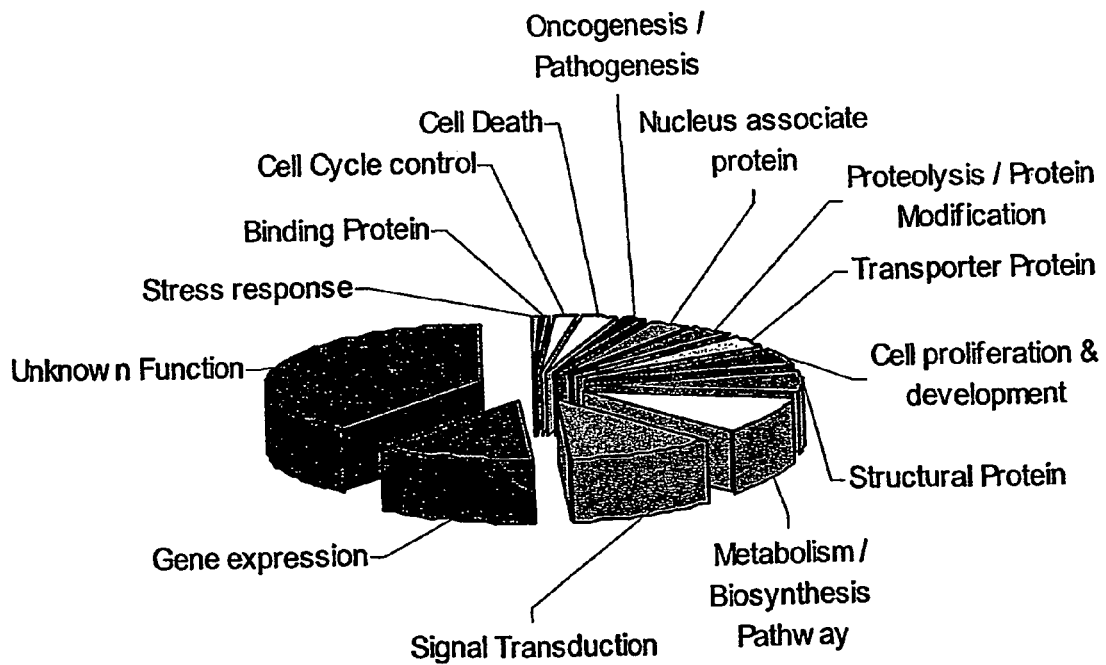

Human A549 lung cancer cells in SCID mice were treated with the MPCB extract. These genes are differentially up-regulated or down-regulated after subtracting out their level of expression in untreated tumor cells. We have classified these genes according to their reported functions (see FIGS. 11 and 12). This information allows one to easily formulate the roles of these genes in the various known biochemical pathways. For example, when 16 of the most highly up-regulated and down-regulated differentially expressed genes are employed, they could be fitted into various known pathways. In additional, when we fit some of these genes into one of the reported pathways for oncogenesis, we could demonstrate that many of these genes are down-regulate. All these data support strongly the anti-oncolytic function of the MPCB extract.

TABLE 1 genes up-regulated at day 2

| Gene Name | Gene Description |
| --- | --- |
| 200000_s_at | PRP8 pre-mRNA processing factor 8 homolog (yeast) |
| 200023_s_at | eukaryotic translation initiation factor 3, subunit 5 (epsilon, 47 kD) |
| 200044_at | splicing factor, arginine/serine-rich 9 |
| 200047_s_at | YY1 transcription factor |
| 200055_at | TAF10 RNA polymerase II, TATA box binding protein (TBP)-associated factor, 30 kD |
| 200069_at | squamous cell carcinoma antigen recognised by T cells 3 |
| 200071_at | sin3-associated polypeptide, 18 kD |
| 200083_at | ubiquitin specific protease 22 |
| 31874_at | growth arrest-specific 2 like 1 |
| 32032_at | clathrin, heavy polypeptide-like 1 [BLAST] |
| 32137_at | jagged 2 |
| 33132_at | cleavage and polyadenylation specific factor 1, 160 kD subunit |
| 33322_i_at | stratifin |
| 34764_at | activity-dependent neuroprotector |
| 36553_at | acetylserotonin O-methyltransferase-like |
| 37462_i_at | splicing factor 3a, subunit 2, 66 kD |
| 37652_at | ribosomal protein L13a |
| 38157_at | dom-3 homolog Z (*C. elegans*) |
| 39248_at | aquaporin 3 |
| 39729_at | peroxiredoxin 2 [BLAST] |
| 39835_at | SET binding factor 1 |
| 40465_at | fatty acid desaturase 2 |
| 40472_at | peroxisomal farnesylated protein |
| 41047_at | chromosome 9 open reading frame 16 |
| 41858_at | RAB30, member RAS oncogene family [BLAST] |
| 44111_at | vacuolar protein sorting 33B (yeast) |
| 44654_at | ribosomal protein S4-like 2 |
| 44696_at | protocadherin beta 17 pseudogene |
| 44783_s_at | hairy/enhancer-of-split related with YRPW motif 1 |
| 46665_at | sema domain, immunoglobulin domain (Ig), transmembrane domain (TM) and short cytoplasmic domain, (semaphorin) 4C |
| 47069_at | Rho GTPase activating protein 8 |
| 47083_at | prion protein interacting protein |
| 50314_i_at | chromosome 20 open reading frame 27 |
| 52164_at | chromosome 11 open reading frame 24 |
| 53071_s_at | hypothetical protein FLJ22222 |
| 59625_at | nucleolar protein 3 (apoptosis repressor with CARD domain) |
| 55872_at | solute carrier family 12, (potassium-chloride transporter) member 5 |
| 60474_at | chromosome 20 open reading frame 42 |
| 64474_g_at | RNA binding motif protein 15 |
| 65884_at | mannosidase, alpha, class 1B, member 1 |
| 91703_at | integrin, beta 1 (fibronectin receptor, beta polypeptide, antigen CD29 includes MDF2, MSK12) |
| 91816_f_at | CUB and Sushi multiple domains 1 |
| 200593_s_at | gb: BC003621.1 /DEF = *Homo sapiens*, heterogeneous nuclear ribonucleoprotein U (scaffold attachment factor A), clone MGC: 1992, mRNA, complete cds. /FEA = mRNA /PROD = heterogeneous nuclear ribonucleopro . . . |
| 200618_at | LIM and SH3 protein 1 |
| 200619_at | splicing factor 3b, subunit 2, 145 kD |
| 200623_s_at | calmodulin 3 (phosphorylase kinase, delta) |
| 200637_s_at | protein tyrosine phosphatase, receptor type, F |
| 200655_s_at | calmodulin 1 (phosphorylase kinase, delta) |
| 200675_at | CD81 antigen (target of antiproliferative antibody 1) |
| 200702_s_at | DEAD/H (Asp-Glu-Ala-Asp/His) box polypeptide 24 [BLAST] |
| 200707_at | protein kinase C substrate 80K-H |

TABLE 1-continued genes up-regulated at day 2

| Gene Name | Gene Description |
| --- | --- |
| 200710_at | acyl-Coenzyme A dehydrogenase, very long chain |
| 200743_s_at | ceroid-lipofuscinosis, neuronal 2, late infantile (Jansky-Bielschowsky disease) |
| 200747_s_at | nuclear mitotic apparatus protein 1 |
| 200766_at | cathepsin D (lysosomal aspartyl protease) |
| 200768_s_at | methionine adenosyltransferase II, alpha |
| 200810_s_at | cold inducible RNA binding protein |
| 200811_at | cold inducible RNA binding protein |
| 200816_s_at | platelet-activating factor acetylhydrolase, isoform Ib, alpha subunit (45 kD) |
| 200827_at | procollagen-lysine, 2-oxoglutarate 5-dioxygenase (lysine hydroxylase, Ehlers-Danlos syndrome type VI) |
| 200864_s_at | RAB11A, member RAS oncogene family |
| 200867_at | zinc finger protein 313 |
| 200875_s_at | nucleolar protein 5A (56 kD with KKE/D repeat) |
| 200884_at | creatine kinase, brain |
| 200891_s_at | signal sequence receptor, alpha (translocon-associated protein alpha) |
| 200899_s_at | meningioma expressed antigen 5 (hyaluronidase) |
| 200903_s_at | S-adenosylhomocysteine hydrolase |
| 200914_x_at | kinectin 1 (kinesin receptor) |
| 200918_s_at | signal recognition particle receptor ('docking protein') |
| 200950_at | actin related protein 2/3 complex, subunit 1A (41 kD) |
| 200959_at | fusion, derived from t(12;16) malignant liposarcoma |
| 200965_s_at | actin binding LIM protein |
| 200967_at | peptidylprolyl isomerase B (cyclophilin B) |
| 200968_s_at | peptidylprolyl isomerase B (cyclophilin B) |
| 200980_s_at | pyruvate dehydrogenase (lipoamide) alpha 1 |
| 200990_at | gb: NM_005762.1 /DEF = *Homo sapiens* KRAB-associated protein 1 (TIF1B), mRNA. /FEA = mRNA /GEN = TIF1B /PROD = KRAB-associated protein 1 /DB_XREF = gi: 5032178 /UG = Hs.228059 KRAB-associated protein 1 /FL = gb: B . . . |
| 201003_x_at | gb: NM_003349.2 /DEF = *Homo sapiens* ubiquitin-conjugating enzyme E2 variant 1 (UBE2V1), transcript variant 2, mRNA. /FEA = mRNA /GEN = UBE2V1 /PROD = ubiquitin-conjugating enzyme E2 variant 1, isoform b / . . . |
| 201008_s_at | thioredoxin interacting protein |
| 201011_at | ribophorin I |
| 201015_s_at | junction plakoglobin |
| 201024_x_at | Consensus includes gb: BG261322 /FEA = EST /DB_XREF = gi: 12771138 /DB_XREF = est: 602373079F1 /CLONE = IMAGE: 4484563 /UG = Hs.158688 KIAA0741 gene product /FL = gb: AB018284.1 gb: AF078035.1 gb: NM_015904.1 |
| 201034_at | L-3-hydroxyacyl-Coenzyme A dehydrogenase, short chain |
| 201037_at | phosphofructokinase, platelet |
| 201052_s_at | proteasome (prosome, macropain) inhibitor subunit 1 (PI31) |
| 201054_at | heterogeneous nuclear ribonucleoprotein A0 [BLAST] |
| 201064_s_at | poly(A) binding protein, cytoplasmic 4 (inducible form) |
| 201065_s_at | general transcription factor II, i [BLAST] |
| 201074_at | SWI/SNF related, matrix associated, actin dependent regulator of chromatin, subfamily c, member 1 |
| 201079_at | synaptogyrin 2 |
| 201082_s_at | dynactin 1 (p150, glued homolog, *Drosophila*) |
| 201102_s_at | phosphofructokinase, liver |
| 201113_at | Tu translation elongation factor, mitochondrial |
| 201128_s_at | ATP citrate lyase |
| 201129_at | gb: NM_006276.2 /DEF = *Homo sapiens* splicing factor, arginineserine-rich 7 (35 kD) (SFRS7), mRNA. /FEA = mRNA /GEN = SFRS7 /PROD = splicing factor, arginineserine-rich 7 (35 kD) /DB_XREF = gi: 6857827 /UG = Hs. . . . |
| 201160_s_at | cold shock domain protein A |
| 201161_s_at | cold shock domain protein A |
| 201176_s_at | archain 1 |
| 201183_s_at | chromodomain helicase DNA binding protein 4 |
| 201188_s_at | inositol 1,4,5-triphosphate receptor, type 3 |
| 201189_s_at | inositol 1,4,5-triphosphate receptor, type 3 |
| 201190_s_at | phosphotidylinositol transfer protein |
| 201198_s_at | proteasome (prosome, macropain) 26S subunit, non-ATPase, 1 |
| 201209_at | histone deacetylase 1 |
| 201225_s_at | serine/arginine repetitive matrix 1 |
| 201244_s_at | v-raf-1 murine leukemia viral oncogene homolog 1 |
| 201247_at | sterol regulatory element binding transcription factor 2 |
| 201255_x_at | HLA-B associated transcript 3 |
| 201264_at | coatomer protein complex, subunit epsilon |

TABLE 1-continued genes up-regulated at day 2

| Gene Name | Gene Description |
| --- | --- |
| 201271_s_at | RNA binding protein (autoantigenic, hnRNP-associated with lethal yellow) |
| 201296_s_at | golgi associated, gamma adaptin ear containing, ARF binding protein 1 |
| 201310_s_at | Kruppel-like factor 4 (gut) |
| 201313_at | gb: NM_001975.1 /DEF = Homo sapiens enolase 2, (gamma, neuronal) (ENO2), mRNA. /FEA = mRNA /GEN = ENO2 /PROD = enolase 2, (gamma, neuronal) /DB_XREF = gi: 5803010 /UG = Hs.146580 enolase 2, (gamma, neuronal) / . . . |
| 201315_x_at | interferon induced transmembrane protein 2 (1-8D) |
| 201331_s_at | signal transducer and activator of transcription 6, interleukin-4 induced |
| 201356_at | splicing factor 3a, subunit 1, 120 kD |
| 201360_at | cystatin C (amyloid angiopathy and cerebral hemorrhage) |
| 201362_at | polymerase (RNA) III (DNA directed) polypeptide F (39 kD) |
| 201363_s_at | polymerase (RNA) III (DNA directed) polypeptide F (39 kD) |
| 201373_at | plectin 1, intermediate filament binding protein, 500 kD |
| 201377_at | synaptosomal-associated protein, 91 kD homolog (mouse) |
| 201379_s_at | tumor protein D52-like 2 |
| 201393_s_at | insulin-like growth factor 2 receptor |
| 201413_at | hydroxysteroid (17-beta) dehydrogenase 4 |
| 201440_at | fatty acid desaturase 2 |
| 201448_at | TIA1 cytotoxic granule-associated RNA binding protein |
| 201454_s_at | Consensus includes gb: AW055008 /FEA = EST /DB_XREF = gi: 5920711 /DB_XREF = est: wy98c09.x1 /CLONE = IMAGE: 2556592 /UG = Hs.293007 aminopeptidase puromycin sensitive /FL = gb: NM_006310.1 |
| 201459_at | RuvB-like 2 (E. coli) |
| 201482_at | quiescin Q6 |
| 201489_at | peptidylprolyl isomerase F (cyclophilin F) |
| 201498_at | ubiquitin specific protease 7 (herpes virus-associated) |
| 201526_at | ADP-ribosylation factor 5 |
| 201545_s_at | poly(A) binding protein, nuclear 1 |
| 201555_at | MCM3 minichromosome maintenance deficient 3 (S. cerevisiae) |
| 201564_s_at | singed-like (fascin homolog, sea urchin) (Drosophila) |
| 201569_s_at | POM121 membrane glycoprotein-like 1 (rat) |
| 201585_s_at | splicing factor proline/glutamine rich (polypyrimidine tract binding protein associated) |
| 201598_s_at | inositol polyphosphate phosphatase-like 1 |
| 201612_at | aldehyde dehydrogenase 9 family, member A1 |
| 201618_x_at | GPAA1P anchor attachment protein 1 homolog (yeast) |
| 201620_at | membrane-bound transcription factor protease, site 1 |
| 201623_s_at | aspartyl-tRNA synthetase |
| 201624_at | aspartyl-tRNA synthetase |
| 201639_s_at | cleavage and polyadenylation specific factor 1, 160 kD subunit |
| 201641_at | bone marrow stromal cell antigen 2 |
| 201643_x_at | chromosome 5 open reading frame 7 |
| 201645_at | tenascin C (hexabrachion) |
| 201650_at | keratin 19 |
| 201669_s_at | myristoylated alanine-rich protein kinase C substrate |
| 201670_s_at | myristoylated alanine-rich protein kinase C substrate |
| 201675_at | A kinase (PRKA) anchor protein 1 |
| 201679_at | tripartite motif-containing 33 |
| 201689_s_at | tumor protein D52 |
| 201690_s_at | tumor protein D52 |
| 201697_s_at | DNA (cytosine-5-)-methyltransferase 1 |
| 201704_at | ectonucleoside triphosphate diphosphohydrolase 6 (putative function) |
| 201714_at | tubulin, gamma 1 |
| 201719_s_at | erythrocyte membrane protein band 4.1-like 2 |
| 201726_at | ELAV (embryonic lethal, abnormal vision, Drosophila)-like 1 (Hu antigen R) |
| 201746_at | tumor protein p53 (Li-Fraumeni syndrome) |
| 201747_s_at | scaffold attachment factor B |
| 201790_s_at | 7-dehydrocholesterol reductase |
| 201795_at | lamin B receptor |
| 201818_at | brain and acute leukemia, cytoplasmic |
| 201828_x_at | CAAX box 1 |
| 201833_at | histone deacetylase 2 |
| 201841_s_at | heat shock 27 kD protein 1 |
| 201853_s_at | cell division cycle 25B |
| 201885_s_at | diaphorase (NADH) (cytochrome b-5 reductase) |
| 201889_at | family with sequence similarity 3, member C |
| 201928_at | plakophilin 4 |
| 201937_s_at | aspartyl aminopeptidase |

TABLE 1-continued genes up-regulated at day 2

| Gene Name | Gene Description |
| --- | --- |
| 201970_s_at | nuclear autoantigenic sperm protein (histone-binding) |
| 202039_at | TGFB1-induced anti-apoptotic factor 1 |
| 202043_s_at | spermine synthase |
| 202060_at | Rho guanine nucleotide exchange factor (GEF) 10 |
| 202066_at | protein tyrosine phosphatase, receptor type, f polypeptide (PTPRF), interacting protein (liprin), alpha 1 |
| 202097_at | nucleoporin 153 kD |
| 202104_s_at | spastic paraplegia 7, paraplegin (pure and complicated autosomal recessive) |
| 202106_at | golgi autoantigen, golgin subfamily a, 3 |
| 202115_s_at | ATP-binding cassette, sub-family A (ABC1), member 12 |
| 202117_at | Rho GTPase activating protein 1 |
| 202119_s_at | copine III |
| 202127_at | myotubularin related protein 2 |
| 202130_at | sudD suppressor of bimD6 homolog (*A. nidulans*) |
| 202136_at | S-adenosylhomocysteine hydrolase-like 1 |
| 202139_at | aldo-keto reductase family 7, member A2 (aflatoxin aldehyde reductase) |
| 202151_s_at | CD2 antigen (cytoplasmic tail) binding protein 2 |
| 202159_at | phenylalanine-tRNA synthetase-like |
| 202161_at | protein kinase C-like 1 |
| 202171_at | zinc finger protein 161 |
| 202173_s_at | zinc finger protein 161 |
| 202180_s_at | major vault protein |
| 202182_at | GCN5 general control of amino-acid synthesis 5-like 2 (yeast) |
| 202189_x_at | polypyrimidine tract binding protein 1 [BLAST] |
| 202219_at | solute carrier family 6 (neurotransmitter transporter, creatine), member 8 |
| 202220_at | calsyntenin 1 |
| 202227_s_at | jumping translocation breakpoint |
| 202228_s_at | dynein, axonemal, intermediate polypeptide 1 |
| 202230_s_at | calcium homeostasis endoplasmic reticulum protein |
| 202240_at | polo-like kinase (*Drosophila*) |
| 202241_at | growth differentiation factor 11 |
| 202251_at | PRP4 pre-mRNA processing factor 4 homolog (yeast) |
| 202275_at | glucose-6-phosphate dehydrogenase |
| 202289_s_at | transforming, acidic coiled-coil containing protein 2 |
| 202308_at | sterol regulatory element binding transcription factor 1 |
| 202320_at | general transcription factor IIIC, polypeptide 1 (alpha subunit, 220 kD) |
| 202344_at | heat shock transcription factor 1 |
| 202357_s_at | B-factor, properdin [BLAST] |
| 202384_s_at | Treacher Collins-Franceschetti syndrome 1 |
| 202424_at | mitogen-activated protein kinase kinase 2 |
| 202430_s_at | phospholipid scramblase 1 |
| 202446_s_at | phospholipid scramblase 1 |
| 202464_s_at | 6-phosphofructo-2-kinase/fructose-2, 6-biphosphatase 3 |
| 202478_at | immunoglobulin kappa joining 1 |
| 202510_s_at | tumor necrosis factor, alpha-induced protein 2 |
| 202534_x_at | dihydrofolate reductase |
| 202536_at | EGF-like-domain, multiple 6 |
| 202540_s_at | 3-hydroxy-3-methylglutaryl-Coenzyme A reductase |
| 202561_at | tankyrase, TRF1-interacting ankyrin-related ADP-ribose polymerase |
| 202569_s_at | MAP/microtubule affinity-regulating kinase 3 |
| 202580_x_at | forkhead box M1 |
| 202589_at | thymidylate synthetase |
| 202605_at | glucuronidase, beta |
| 202686_s_at | AXL receptor tyrosine kinase |
| 202715_at | carbamoyl-phosphate synthetase 2, aspartate transcarbamylase, and dihydroorotase |
| 202718_at | insulin-like growth factor binding protein 2 (36 kD) |
| 202757_at | rotatin |
| 202804_at | ATP-binding cassette, sub-family C (CFTR/MRP), member 1 |
| 202809_s_at | down-regulated in colon cancer 1 |
| 202812_at | glucosidase, alpha; acid (Pompe disease, glycogen storage disease type II) |
| 202836_s_at | mannosidase, alpha, class 1A, member 2 |
| 202853_s_at | RYK receptor-like tyrosine kinase |
| 202870_s_at | CDC20 cell division cycle 20 homolog (*S. cerevisiae*) |
| 202890_at | Consensus includes gb: AW242297 /FEA = EST /DB_XREF = gi: 6576051 /DB_XREF = est: xm96b11.x1 /CLONE = IMAGE: 2692029 /UG = Hs.146388 microtubule-associated protein 7 /FL = gb: NM_003980.1 |
| 202917_s_at | S100 calcium binding protein A8 (calgranulin A) |

TABLE 1-continued genes up-regulated at day 2

| Gene Name | Gene Description |
| --- | --- |
| 202929_s_at | D-dopachrome tautomerase |
| 202934_at | hexokinase 2 [BLAST] |
| 202936_s_at | SRY (sex determining region Y)-box 9 (campomelic dysplasia, autosomal sex-reversal) |
| 202951_at | serine/threonine kinase 38 |
| 202962_at | kinesin family member 13B |
| 202979_s_at | ras homolog gene family, member U |
| 202998_s_at | lysyl oxidase-like 2 |
| 203021_at | secretory leukocyte protease inhibitor (antileukoproteinase) [BLAST] |
| 203062_s_at | heparan sulfate 2-O-sulfotransferase 1 |
| 203065_s_at | caveolin 1, caveolae protein, 22 kD [BLAST] |
| 203067_at | cysteine and glycine-rich protein 3 (cardiac LIM protein) |
| 203098_at | chromodomain protein, Y chromosome-like |
| 203102_s_at | mannosyl (alpha-1,6-)-glycoprotein beta-1,2-N-acetylglucosaminyltransferase |
| 203103_s_at | HIV TAT specific factor 1 |
| 203108_at | retinoic acid induced 3 |
| 203109_at | ubiquitin-conjugating enzyme E2M (UBC12 homolog, yeast) |
| 203124_s_at | solute carrier family 11 (proton-coupled divalent metal ion transporters), member 2 |
| 203126_at | inositol(myo)-1(or 4)-monophosphatase 2 |
| 203137_at | M-phase phosphoprotein 1 |
| 203153_at | interferon-induced protein with tetratricopeptide repeats 1 |
| 203155_at | SET domain, bifurcated 1 |
| 203156_at | A kinase (PRKA) anchor protein 11 |
| 203184_at | fibrillin 2 (congenital contractural arachnodactyly) |
| 203189_s_at | NADH dehydrogenase (ubiquinone) Fe—S protein 8 (23 kD) (NADH-coenzyme Q reductase) |
| 203195_s_at | nucleoporin 98 kD |
| 203198_at | cyclin-dependent kinase 9 (CDC2-related kinase) [BLAST] |
| 203219_s_at | adenine phosphoribosyltransferase |
| 203224_at | chromosome 20 open reading frame 38 |
| 203234_at | uridine phosphorylase |
| 203244_at | peroxisome receptor 1 |
| 203252_at | gb: NM_005851.1 /DEF = Homo sapiens tumor suppressor deleted in oral cancer-related 1 (DOC-1R), mRNA. /FEA = mRNA /GEN = DOC-1R /PROD = tumor suppressor deleted in oral cancer-related1 /DB_XREF = gi: 503166 . . . |
| 203262_s_at | DNA segment on chromosome X (unique) 9928 expressed sequence |
| 203276_at | lamin B1 |
| 203282_at | glucan (1,4-alpha-), branching enzyme 1 (glycogen branching enzyme, Andersen disease, glycogen storage disease type IV) |
| 203286_at | Rho-related BTB domain containing 3 |
| 203338_at | protein phosphatase 2, regulatory subunit B (B56), epsilon isoform |
| 203386_at | chromosome 21 open reading frame 108 |
| 203391_at | gb: NM_004470.1 /DEF = Homo sapiens FK506-binding protein 2 (13 kD) (FKBP2), mRNA. /FEA = mRNA /GEN = FKBP2 /PROD = FK506-binding protein 2 (13 kD) /DB_XREF = gi: 4758381 /UG = Hs.227729 FK506-binding protein 2 . . . |
| 203417_at | microfibrillar-associated protein 2 |
| 203439_s_at | stanniocalcin 2 |
| 203477_at | collagen, type XV, alpha 1 |
| 203482_at | zinc finger protein 334 |
| 203495_at | syndecan 3 (N-syndecan) |
| 203564_at | Fanconi anemia, complementation group G |
| 203612_at | bystin-like [BLAST] |
| 203683_s_at | vascular endothelial growth factor B |
| 203690_at | ariadne homolog 2 (Drosophila) |
| 203701_s_at | chromosome 20 open reading frame 13 |
| 203739_at | zinc finger protein 217 |
| 203767_s_at | steroid sulfatase (microsomal), arylsulfatase C, isozyme S |
| 203775_at | solute carrier family 25, member 13 (citrin) |
| 203802_x_at | LUC7-like (S. cerevisiae) |
| 203818_s_at | splicing factor 3a, subunit 3, 60 kD |
| 203825_at | bromodomain containing 3 |
| 203828_s_at | zinc finger protein 206 |
| 203831_at | [BLAST] |
| 203848_at | A kinase (PRKA) anchor protein 8 |
| 203867_s_at | toll interacting protein |
| 203919_at | transcription elongation factor A (SII), 2 |
| 203955_at | GRB2-associated binding protein 2 |
| 203974_at | synapsin III |

TABLE 1-continued genes up-regulated at day 2

| Gene Name | Gene Description |
|---|---|
| 203976_s_at | chromatin assembly factor 1, subunit A (p150) |
| 204022_at | abhydrolase domain containing 1 |
| 204030_s_at | schwannomin interacting protein 1 |
| 204058_at | malic enzyme 1, NADP(+)-dependent, cytosolic |
| 204133_at | cyclin E2 |
| 204142_at | SRY (sex determining region Y)-box 6 |
| 204143_s_at | SRY (sex determining region Y)-box 6 |
| 204178_s_at | RNA binding motif protein 14 |
| 204224_s_at | GTP cyclohydrolase 1 (dopa-responsive dystonia) |
| 204238_s_at | secretagogin, EF-hand calcium binding protein |
| 204274_at | Consensus includes gb: AA812215 /FEA = EST /DB_XREF = gi: 2881826 /DB_XREF = est: ob84g01.s1 /CLONE = IMAGE: 1338096 /UG = Hs.9222 estrogen receptor binding site associated, antigen, 9 /FL = gb: BC005249.1 gb: AF0 . . . |
| 204275_at | small optic lobes homolog (*Drosophila*) |
| 204295_at | surfeit 1 |
| 204367_at | Sp2 transcription factor |
| 204372_s_at | KH-type splicing regulatory protein (FUSE binding protein 2) |
| 204383_at | clathrin, heavy polypeptide-like 1 |
| 204401_at | potassium intermediate/small conductance calcium-activated channel, subfamily N, member 4 |
| 204409_s_at | eukaryotic translation initiation factor 1A, Y chromosome |
| 204480_s_at | chromosome 9 open reading frame 16 |
| 204520_x_at | bromodomain containing 1 |
| 204521_at | cleavage and polyadenylation specific factor 1, 160 kD subunit |
| 204531_s_at | breast cancer 1, early onset |
| 204584_at | L1 cell adhesion molecule (hydrocephalus, stenosis of aqueduct of Sylvius 1, MASA (mental retardation, aphasia, shuffling gait and adducted thumbs) syndrome, spastic paraplegia 1) |
| 204617_s_at | aquaporin 9 |
| 204641_at | NIMA (never in mitosis gene a)-related kinase 2 |
| 204698_at | interferon stimulated gene (20 kD) |
| 204717_s_at | solute carrier family 29 (nucleoside transporters), member 2 |
| 204805_s_at | H1 histone family, member X |
| 204808_s_at | transmembrane protein 5 |
| 204839_at | membrane-bound transcription factor protease, site 2 |
| 204849_at | transcription factor-like 5 (basic helix-loop-helix) |
| 204857_at | MAD1 mitotic arrest deficient-like 1 (yeast) |
| 204858_s_at | endothelial cell growth factor 1 (platelet-derived) |
| 204875_s_at | GDP-mannose 4,6-dehydratase |
| 204908_s_at | B-cell CLL/lymphoma 3 |
| 205000_at | DEAD/H (Asp-Glu-Ala-Asp/His) box polypeptide, Y chromosome |
| 205053_at | primase, polypeptide 1 (49 kD) |
| 205068_s_at | paternally expressed 10 |
| 205081_at | cysteine-rich protein 1 (intestinal) |
| 205155_s_at | spectrin, beta, non-erythrocytic 2 |
| 205199_at | carbonic anhydrase IX |
| 205202_at | protein-L-isoaspartate (D-aspartate) O-methyltransferase |
| 205353_s_at | prostatic binding protein |
| 205382_s_at | D component of complement (adipsin) |
| 205412_at | acetyl-Coenzyme A acetyltransferase 1 (acetoacetyl Coenzyme A thiolase) |
| 205436_s_at | H2A histone family, member X |
| 205449_at | cleavage and polyadenylation specific factor 1, 160 kD subunit |
| 205501_at | phosphodiesterase 10A |
| 205516_x_at | neuronal guanine nucleotide exchange factor |
| 205527_s_at | gem (nuclear organelle) associated protein 4 |
| 205534_at | BH-protocadherin (brain-heart) [BLAST] |
| 205546_s_at | tyrosine kinase 2 |
| 205552_s_at | 2',5'-oligoadenylate synthetase 1 (40-46 kD) |
| 205565_s_at | Friedreich ataxia |
| 205583_s_at | NIMA (never in mitosis gene a)-related kinase 11 |
| 205640_at | aldehyde dehydrogenase 3 family, member B1 |
| 205658_s_at | small nuclear RNA activating complex, polypeptide 4, 190 kD |
| 205780_at | BCL2-interacting killer (apoptosis-inducing)- |
| 205961_s_at | gb: NM_004682.1 /DEF = *Homo sapiens* PC4 and SFRS1 interacting protein 2 (PSIP2), mRNA. /FEA = mRNA /GEN = PSIP2 /PROD = PC4 and SFRS1 interacting protein 2 /DB_XREF = gi: 4758869 /UG = Hs.306179 PC4 and SFRS1 . . . |

TABLE 1-continued genes up-regulated at day 2

| Gene Name | Gene Description |
|---|---|
| 205967_at | H4 histone family, member G |
| 206023_at | neuromedin U |
| 206095_s_at | gb: NM_006625.2 /DEF = *Homo sapiens* TLS-associated serine-arginine protein 1 (TASR1), mRNA. /FEA = mRNA /GEN = TASR1 /PROD = TLS-associated serine-arginine protein 1 /DB_XREF = gi: 12056474 /UG = Hs.288038 TL . . . |
| 206102_at | tripartite motif-containing 14 |
| 206200_s_at | annexin A11 |
| 206332_s_at | interferon, gamma-inducible protein 16 |
| 206499_s_at | chromosome condensation 1 |
| 206785_s_at | killer cell lectin-like receptor subfamily C, member 2 |
| 206809_s_at | heterogeneous nuclear ribonucleoprotein A3 |
| 207002_s_at | pleiomorphic adenoma gene-like 1 |
| 207076_s_at | argininosuccinate synthetase [BLAST] |
| 207122_x_at | sulfotransferase family, cytosolic, 1A, phenol-preferring, member 2 |
| 207140_at | alkaline phosphatase, intestinal |
| 207165_at | hyaluronan-mediated motility receptor (RHAMM) |
| 207169_x_at | discoidin domain receptor family, member 1 |
| 207170_s_at | ribosomal protein L36 |
| 207196_s_at | UDP-Gal: betaGlcNAc beta 1,3-galactosyltransferase, polypeptide 5 |
| 207414_s_at | paired basic amino acid cleaving system 4 |
| 207564_x_at | O-linked N-acetylglucosamine (GlcNAc) transferase (UDP-N-acetylglucosamine:polypeptide-N-acetylglucosaminyl transferase) |
| 207622_s_at | ATP-binding cassette, sub-family F (GCN20), member 2 |
| 207714_s_at | serine (or cysteine) proteinase inhibitor, clade H (heat shock protein 47), member 1, (collagen binding protein 1) |
| 207723_s_at | killer cell lectin-like receptor subfamily C, member 3 |
| 207760_s_at | nuclear receptor co-repressor 2 |
| 207761_s_at | component of oligomeric golgi complex 4 |
| 207824_s_at | MYC-associated zinc finger protein (purine-binding transcription factor) |
| 207831_x_at | deoxyhypusine synthase |
| 207842_s_at | zyxin [BLAST] |
| 207847_s_at | mucin 1, transmembrane |
| 208072_s_at | diacylglycerol kinase, delta (130 kD) |
| 208132_x_at | HLA-B associated transcript 2 |
| 208149_x_at | DEAD/H (Asp-Glu-Ala-Asp/His) box polypeptide 11 (CHL1-like helicase homolog, *S. cerevisiae*) [BLAST] |
| 208156_x_at | gb: NM_031308.1 /DEF = *Homo sapiens* epiplakin 1 (EPPK1), mRNA. /FEA = mRNA /GEN = EPPK1 /PROD = epiplakin 1 /DB_XREF = gi: 13876385 /FL = gb: NM_031308.1 |
| 208159_x_at | DEAD/H (Asp-Glu-Ala-Asp/His) box polypeptide 11 (CHL1-like helicase homolog, *S. cerevisiae*) |
| 208248_x_at | amyloid beta (A4) precursor-like protein 2 |
| 208270_s_at | arginyl aminopeptidase (aminopeptidase B) |
| 208313_s_at | splicing factor 1 |
| 208336_s_at | glycoprotein, synaptic 2 |
| 208407_s_at | catenin (cadherin-associated protein), delta 1 |
| 208436_s_at | interferon regulatory factor 7 |
| 208617_s_at | protein tyrosine phosphatase type IVA, member 2 |
| 208621_s_at | villin 2 (ezrin) |
| 208625_s_at | eukaryotic translation initiation factor 4 gamma, 1 |
| 208636_at | actinin, alpha 1 |
| 208647_at | farnesyl-diphosphate farnesyltransferase 1 |
| 208655_at | cyclin I |
| 208676_s_at | chromosome 20 open reading frame 54 |
| 208700_s_at | transketolase (Wernicke-Korsakoff syndrome) |
| 208703_s_at | amyloid beta (A4) precursor-like protein 2 |
| 208704_x_at | amyloid beta (A4) precursor-like protein 2 |
| 208705_s_at | 5'-nucleotidase, cytosolic IA |
| 208706_s_at | 5'-nucleotidase, cytosolic IA |
| 208713_at | protein tyrosine phosphatase, non-receptor type 21 |
| 208714_at | NADH dehydrogenase (ubiquinone) flavoprotein 1 (51 kD) |
| 208719_s_at | DEAD/H (Asp-Glu-Ala-Asp/His) box polypeptide 17 (72 kD) |
| 208729_x_at | major histocompatibility complex, class I, B |
| 208773_s_at | baculoviral IAP repeat-containing 6 (apollon) |
| 208774_at | casein kinase 1, delta |
| 208788_at | transgene insertion 2, Craig B Thompson |
| 208794_s_at | SWI/SNF related, matrix associated, actin dependent regulator of chromatin, subfamily a, member 4 |
| 208798_x_at | F-box only protein 21 |
| 208804_s_at | splicing factor, arginine/serine-rich 6 |

TABLE 1-continued genes up-regulated at day 2

| Gene Name | Gene Description |
| --- | --- |
| 208809_s_at | gb: AL136632.1 /DEF = *Homo sapiens* mRNA; cDNA DKFZp564G182 (from clone DKFZp564G182); complete cds. /FEA = mRNA /GEN = DKFZp564G182 /PROD = hypothetical protein /DB_XREF = gi: 12052789 /UG = Hs.173685 hypothe . . . |
| 208820_at | PTK2 protein tyrosine kinase 2 |
| 208858_s_at | WD repeat domain 7 |
| 208863_s_at | splicing factor, arginine/serine-rich 1 (splicing factor 2, alternate splicing factor) |
| 208880_s_at | chromosome 20 open reading frame 14 |
| 208890_s_at | plexin B2 |
| 208891_at | dual specificity phosphatase 6 |
| 208892_s_at | dual specificity phosphatase 6 |
| 208906_at | ligand of numb-protein X |
| 208912_s_at | gb: BC001362.1 /DEF = *Homo sapiens*, 2,3-cyclic nucleotide 3 phosphodiesterase, clone MGC: 2262, mRNA, complete cds. /FEA = mRNA /PROD = 2,3-cyclic nucleotide 3 phosphodiesterase /DB_XREF = gi: 12655028 /UG . . . |
| 208923_at | cytoplasmic FMR1 interacting protein 1 |
| 208928_at | P450 (cytochrome) oxidoreductase |
| 208930_s_at | interleukin enhancer binding factor 3, 90 kD |
| 208931_s_at | interleukin enhancer binding factor 3, 90 kD |
| 208938_at | papillary renal cell carcinoma (translocation-associated) |
| 208968_s_at | aldo-keto reductase family 1, member B10 (aldose reductase) |
| 208978_at | cysteine-rich protein 2 |
| 208984_x_at | RNA binding motif protein 10 |
| 208988_at | F-box and leucine-rich repeat protein 11 |
| 208998_at | uncoupling protein 2 (mitochondrial, proton carrier) |
| 209007_s_at | solute carrier family 17 (sodium-dependent inorganic phosphate cotransporter), member 7 |
| 209029_at | COP9 constitutive photomorphogenic homolog subunit 7A (*Arabidopsis*) |
| 209044_x_at | splicing factor 3b, subunit 4, 49 kD |
| 209052_s_at | Wolf-Hirschhorn syndrome candidate 1 |
| 209053_s_at | Wolf-Hirschhorn syndrome candidate 1 |
| 209054_s_at | Wolf-Hirschhorn syndrome candidate 1 |
| 209075_s_at | bromodomain containing 4 |
| 209112_at | cyclin-dependent kinase inhibitor 1B (p27, Kip1) |
| 209118_s_at | platelet-activating factor acetylhydrolase, isoform Ib, pseudogene 1 |
| 209120_at | nuclear receptor subfamily 2, group F, member 2 |
| 209128_s_at | squamous cell carcinoma antigen recognised by T cells 3 |
| 209153_s_at | transcription factor 3 (E2A immunoglobulin enhancer binding factors E12/E47) |
| 209156_s_at | collagen, type VI, alpha 2 |
| 209215_at | glycoprotein A33 (transmembrane) |
| 209228_x_at | zinc finger protein 212 |
| 209236_at | solute carrier family 23 (nucleobase transporters), member 1 |
| 209262_s_at | nuclear receptor subfamily 2, group F, member 6 |
| 209263_x_at | transmembrane 4 superfamily member 7 |
| 209264_s_at | transmembrane 4 superfamily member 7 |
| 209265_s_at | thioredoxin interacting protein |
| 209289_at | nuclear factor I/B |
| 209290_s_at | nuclear factor I/B |
| 209295_at | tumor necrosis factor receptor superfamily, member 10b |
| 209318_x_at | pleiomorphic adenoma gene-like 1 |
| 209332_s_at | MAX protein |
| 209337_at | gb: AF063020.1 /DEF = *Homo sapiens* lens epithelium-derived growth factor mRNA, complete cds. /FEA = mRNA /PROD = lens epithelium-derived growth factor /DB_XREF = gi: 3283351 /UG = Hs.82110 PC4 and SFRS1 int . . . |
| 209341_s_at | inhibitor of kappa light polypeptide gene enhancer in B-cells, kinase beta |
| 209407_s_at | deformed epidermal autoregulatory factor 1 (*Drosophila*) |
| 209409_at | growth factor receptor-bound protein 10 |
| 209449_at | chromosome 6 open reading frame 28 |
| 209496_at | retinoic acid receptor responder (tazarotene induced) 2 |
| 209505_at | nuclear receptor subfamily 2, group F, member 1 |
| 209581_at | HRAS-like suppressor 3 |
| 209607_x_at | sulfotransferase family, cytosolic, 1A, phenol-preferring, member 3 |
| 209623_at | methylcrotonoyl-Coenzyme A carboxylase 2 (beta) [BLAST] |
| 209630_s_at | G protein-coupled receptor 37 (endothelin receptor type B-like) |

TABLE 1-continued

<u>genes up-regulated at day 2</u>

| Gene Name | Gene Description |
| --- | --- |
| 209675_s_at | protein tyrosine phosphatase, non-receptor type 21 |
| 209723_at | serine (or cysteine) proteinase inhibitor, clade B (ovalbumin), member 9 |
| 209729_at | growth arrest-specific 2 like 1 |
| 209754_s_at | thymopoietin |
| 209759_s_at | DEAD/H (Asp-Glu-Ala-Asp/His) box polypeptide 37 |
| 209784_s_at | jagged 2 |
| 209832_s_at | carcinoembryonic antigen-related cell adhesion molecule 1 |
| 209873_s_at | plakophilin 3 |
| 209899_s_at | DnaJ (Hsp40) homolog, subfamily C, member 8 [BLAST] |
| 210010_s_at | solute carrier family 25 (mitochondrial carrier; citrate transporter), member 1 |
| 210026_s_at | succinate dehydrogenase complex, subunit D, integral membrane protein pseudogene 1 |
| 210028_s_at | origin recognition complex, subunit 3-like (yeast) |
| 210069_at | carnitine palmitoyltransferase I, muscle |
| 210105_s_at | FYN oncogene related to SRC, FGR, YES |
| 210111_s_at | G protein-coupled receptor 61 |
| 210150_s_at | laminin, alpha 5 |
| 210208_x_at | HLA-B associated transcript 3 |
| 210336_x_at | zinc finger protein 42 (myeloid-specific retinoic acid-responsive) |
| 210337_s_at | ATP citrate lyase |
| 210371_s_at | retinoblastoma binding protein 4 |
| 210410_s_at | mutS homolog 5 (*E. coli*) |
| 210428_s_at | hepatocyte growth factor-regulated tyrosine kinase substrate |
| 210448_s_at | purinergic receptor P2X, ligand-gated ion channel, 5 |
| 210802_s_at | serine protease inhibitor, Kazal type 4 |
| 210878_s_at | chromosome 5 open reading frame 7 |
| 210891_s_at | general transcription factor II, i |
| 211052_s_at | tubulin-specific chaperone d [BLAST] |
| 211060_x_at | GPAA1P anchor attachment protein 1 homolog (yeast) [BLAST] |
| 211065_x_at | phosphofructokinase, liver [BLAST] |
| 211075_s_at | gb: Z25521.1 /DEF = *H. sapiens* integrin associated protein mRNA, complete CDS,. /FEA = mRNA /PROD = integrin associated protein /DB_XREF = gi: 396704 /FL = gb: Z25521.1 |
| 211270_x_at | polypyrimidine tract binding protein 1 |
| 211284_s_at | granulin |
| 211300_s_at | tumor protein p53 (Li-Fraumeni syndrome) |
| 211358_s_at | neuronal guanine nucleotide exchange factor |
| 211375_s_at | interleukin enhancer binding factor 3, 90 kD |
| 211385_x_at | sulfotransferase family, cytosolic, 1A, phenol-preferring, member 2 |
| 211529_x_at | HLA-G histocompatibility antigen, class I, G |
| 211564_s_at | KH-type splicing regulatory protein (FUSE binding protein 2) |
| 211596_s_at | l(3)mbt-like (*Drosophila*) [BLAST] |
| 211618_s_at | gb: M31008.1 /DEF = Human intestinal alkaline phosphatase mRNA, complete cds. /FEA = mRNA /GEN = ALPI /DB_XREF = gi: 178443 /FL = gb: M31008.1 |
| 211678_s_at | maternally expressed 3 [BLAST] |
| 211929_at | heterogeneous nuclear ribonucleoprotein A3 |
| 211967_at | F-box only protein 32 [BLAST] |
| 211986_at | AHNAK nucleoprotein (desmoyokin) |
| 212005_at | golgi associated, gamma adaptin ear containing, ARF binding protein 1 |
| 212015_x_at | polypyrimidine tract binding protein 1 [BLAST] |
| 212028_at | proline dehydrogenase (oxidase) 2 |
| 212030_at | proline dehydrogenase (oxidase) 2 |
| 212032_s_at | prostate tumor over expressed gene 1 [BLAST] |
| 212033_at | proline dehydrogenase (oxidase) 2 |
| 212037_at | pinin, desmosome associated protein |
| 212056_at | MDN1, midasin homolog (yeast) |
| 212062_at | ATPase, Class II, type 9A |
| 212067_s_at | Consensus includes gb: AL573058 /FEA = EST /DB_XREF = gi: 12931931 /DB_XREF = est: AL573058 /CLONE = CS0DI014YC05 (3 prime) /UG = Hs.1279 complement component 1, r subcomponent |
| 212068_s_at | ATPase, Class V, type 10B |
| 212069_s_at | ATPase, Class V, type 10B |
| 212089_at | lamin A/C |
| 212124_at | retinoic acid induced 17 |
| 212126_at | regulator of G-protein signalling 8 |
| 212137_at | ATP synthase mitochondrial F1 complex assembly factor 2 |

TABLE 1-continued genes up-regulated at day 2

| Gene Name | Gene Description |
| --- | --- |
| 212139_at | GCN1 general control of amino-acid synthesis 1-like 1 (yeast) |
| 212159_x_at | adaptor-related protein complex 2, alpha 2 subunit |
| 212170_at | RNA binding motif protein 12 |
| 212179_at | SAM domain and HD domain, 1 |
| 212186_at | acetyl-Coenzyme A carboxylase alpha |
| 212203_x_at | interferon induced transmembrane protein 3 (1-8U)- |
| 212206_s_at | opsin 4 (melanopsin) [BLAST] |
| 212218_s_at | F-box only protein 9 [BLAST] |
| 212231_at | F-box only protein 21 |
| 212251_at | nuclear autoantigenic sperm protein (histone-binding) [BLAST] |
| 212269_s_at | MCM3 minichromosome maintenance deficient 3 (*S. cerevisiae*) associated protein |
| 212285_s_at | agrin |
| 212300_at | Consensus includes gb: AL049795 /DEF = Human DNA sequence from clone RP4-622L5 on chromosome 1p34.2-36.11. Contains the gene for importin alpha 7 (karyopherin), up to six novel genes and the 5 end o . . . |
| 212307_s_at | O-linked N-acetylglucosamine (GlcNAc) transferase (UDP-N-acetylglucosamine:polypeptide-N-acetylglucosaminyl transferase) |
| 212316_at | Rho-related BTB domain containing 2 |
| 212319_at | synaptosomal-associated protein, 91 kD homolog (mouse) |
| 212361_s_at | ATPase, Ca++ transporting, cardiac muscle, slow twitch 2 [BLAST] |
| 212396_s_at | golgi associated, gamma adaptin ear containing, ARF binding protein 2 |
| 212403_at | solute carrier family 25 (mitochondrial oxodicarboxylate carrier), member 21 [BLAST] |
| 212408_at | golgi associated, gamma adaptin ear containing, ARF binding protein 1 |
| 212414_s_at | capicua homolog (*Drosophila*) |
| 212429_s_at | general transcription factor IIIC, polypeptide 2 (beta subunit, 110 kD) |
| 212456_at | chromosome 21 open reading frame 80 |
| 212493_s_at | chromosome 20 open reading frame 30 |
| 212498_at | brain-specific angiogenesis inhibitor 3 [BLAST] |
| 212499_s_at | collagen, type II, alpha 1 (primary osteoarthritis, spondyloepiphyseal dysplasia, congenital) [BLAST] |
| 212520_s_at | SWI/SNF related, matrix associated, actin dependent regulator of chromatin, subfamily a, member 4 |
| 212547_at | Consensus includes gb: N34842 /FEA = EST /DB_XREF = gi: 1155984 /DB_XREF = est: yy45d11.s1 /CLONE = IMAGE: 276501 /UG = Hs.6580 *Homo sapiens* cDNA: FLJ23227 fis, clone CAE00645, highly similar to AF052138 Homo . . . |
| 212561_at | ATPase, Class VI, type 11A |
| 212563_at | block of proliferation 1 |
| 212566_at | ret finger protein 2 |
| 212589_at | related RAS viral (r-ras) oncogene homolog 2 |
| 212612_at | REST corepressor |
| 212630_at | chromobox homolog 3 (HP1 gamma homolog, *Drosophila*) |
| 212643_at | collagen, type II, alpha 1 (primary osteoarthritis, spondyloepiphyseal dysplasia, congenital) [BLAST] |
| 212644_s_at | collagen, type II, alpha 1 (primary osteoarthritis, spondyloepiphyseal dysplasia, congenital) [BLAST] |
| 212647_at | related RAS viral (r-ras) oncogene homolog |
| 212685_s_at | Consensus includes gb: AI608789 /FEA = EST /DB_XREF = gi: 4617956 /DB_XREF = est: tw94g12.x1 /CLONE = IMAGE: 2267398 /UG = Hs.52515 transducin (beta)-like 2 |
| 212691_at | SH3-domain GRB2-like endophilin B2 [BLAST] |
| 212693_at | MDN1, midasin homolog (yeast) |
| 212747_at | chromosome 17 open reading frame 31 [BLAST] |
| 212752_at | cytoplasmic linker associated protein 1 |
| 212761_at | transcription factor 7-like 2 (T-cell specific, HMG-box) [BLAST] |
| 212762_s_at | transcription factor 7-like 2 (T-cell specific, HMG-box) [BLAST] |
| 212770_at | pleckstrin homology domain-containing, family A (phosphoinositide binding specific) member 4 |
| 212774_at | zinc finger protein 238 |
| 212825_at | PAX transcription activation domain interacting protein 1 like |
| 212887_at | Sec23 homolog A (*S. cerevisiae*) |
| 212890_at | integrin, beta 1 (fibronectin receptor, beta polypeptide, antigen CD29 includes MDF2, MSK12) |

TABLE 1-continued genes up-regulated at day 2

| Gene Name | Gene Description |
|---|---|
| 212900_at | SEC24 related gene family, member A (*S. cerevisiae*) |
| 212919_at | FGD1 family, member 3 [BLAST] |
| 212929_s_at | fatty-acid-Coenzyme A ligase, long-chain 6 |
| 212936_at | neurocalcin delta [BLAST] |
| 212955_s_at | polymerase (RNA) II (DNA directed) polypeptide I (14.5 kD) |
| 212973_at | Consensus includes gb: AI692341 /FEA = EST /DB_XREF = gi: 4969681 /DB_XREF = est: wd85g04.x1 /CLONE = IMAGE: 2338422 /UG = Hs.79886 ribose 5-phosphate isomerase A (ribose 5-phosphate epimerase) |
| 212987_at | F-box only protein 9 |
| 212993_at | G protein-coupled receptor kinase 7 |
| 213026_at | APG12 autophagy 12-like (*S. cerevisiae*) |
| 213029_at | son of sevenless homolog 1 (*Drosophila*) [BLAST] |
| 213032_at | son of sevenless homolog 1 (*Drosophila*) [BLAST] |
| 213041_s_at | ATP synthase, H+ transporting, mitochondrial F1 complex, delta subunit |
| 213050_at | activity-regulated cytoskeleton-associated protein |
| 213051_at | low voltage-activated T-type calcium channel alpha-1 subunit (CACNA1I) |
| 213057_at | ATP synthase mitochondrial F1 complex assembly factor 2 [BLAST] |
| 213089_at | Consensus includes gb: AU158490 /FEA = EST /DB_XREF = gi: 11020011 /DB_XREF = est: AU158490 /CLONE = PLACE3000042 /UG = Hs.303632 Human DNA sequence from clone RP11-110H4 on chromosome 5 Contains a pseudogene . . . |
| 213145_at | nucleoporin 133 kD [BLAST] |
| 213154_s_at | chromosome 17 open reading frame 31 |
| 213182_x_at | Consensus includes gb: R78668 /FEA = EST /DB_XREF = gi: 854949 /DB_XREF = est: yi74c04.r1 /CLONE = IMAGE: 144966 /UG = Hs.106070 cyclin-dependent kinase inhibitor 1C (p57, Kip2) |
| 213212_x_at | F-box only protein 21 |
| 213243_at | F-box and WD-40 domain protein 1B |
| 213263_s_at | mitogen-activated protein kinase kinase kinase 12 |
| 213294_at | aldo-keto reductase family 1, member C1 (dihydrodiol dehydrogenase 1; 20-alpha (3-alpha)-hydroxysteroid dehydrogenase) |
| 213302_at | phosphoribosylformylglycinamidine synthase (FGAR amidotransferase) |
| 213304_at | mitochondrial ribosomal protein S27 |
| 213313_at | nucleoporin 62 kD |
| 213318_s_at | HLA-B associated transcript 3 |
| 213360_s_at | chromosome 21 open reading frame 108 |
| 213378_s_at | DEAD/H (Asp-Glu-Ala-Asp/His) box polypeptide 11 (CHL1-like helicase homolog, *S. cerevisiae*) |
| 213390_at | chromosome 19 open reading frame 7 |
| 213398_s_at | mitochondrial ribosomal protein S22 |
| 213400_s_at | transducin (beta)-like 1X-linked [BLAST] |
| 213410_at | golgi associated, gamma adaptin ear containing, ARF binding protein 1 |
| 213428_s_at | collagen, type VI, alpha 1 |
| 213460_x_at | chromosome 21 open reading frame 108 |
| 213505_s_at | C-type (calcium dependent, carbohydrate-recognition domain) lectin, superfamily member 1 (cartilage-derived) |
| 213518_at | RNA binding motif protein 15 |
| 213581_at | chromosome 21 open reading frame 67 |
| 213645_at | Consensus includes gb: AF305057 /DEF = *Homo sapiens* RTS (RTS) gene, complete cds, alternatively spliced /FEA = mRNA_1 /DB_XREF = gi: 11094017 /UG = Hs.180433 rTS beta protein |
| 213668_s_at | Consensus includes gb: AI989477 /FEA = EST /DB_XREF = gi: 5836358 /DB_XREF = est: ws25bl1.x1 /CLONE = IMAGE: 2498205 /UG = Hs.83484 SRY (sex determining region Y)-box 4 |
| 213670_x_at | chromosome 21 open reading frame 108 |
| 213682_at | Consensus includes gb: AL036344 /FEA = EST /DB_XREF = gi: 5927743 /DB_XREF = est: DKFZp564A053_r1 /CLONE = DKFZp564A053 /UG = Hs.169329 DKFZP564A043 protein |
| 213704_at | Rab geranylgeranyltransferase, beta subunit |
| 213720_s_at | SWI/SNF related, matrix associated, actin dependent regulator of chromatin, subfamily a, member 4 [BLAST] |
| 213746_s_at | filamin A, alpha (actin binding protein 280) [BLAST] |
| 213773_x_at | LUC7-like (*S. cerevisiae*) |
| 213838_at | RAN binding protein 9 |
| 213842_x_at | Williams Beuren syndrome chromosome region 22 |
| 213872_at | Consensus includes gb: BE465032 /FEA = EST /DB_XREF = gi: 9510807 /DB_XREF = est: hv76g09.x1 /CLONE = IMAGE: 3179392 /UG = Hs.173685 hypothetical protein FLJ12619 |

TABLE 1-continued genes up-regulated at day 2

| Gene Name | Gene Description |
|---|---|
| 213887_s_at | polymerase (RNA) II (DNA directed) polypeptide E (25 kD) [BLAST] |
| 213892_s_at | adenine phosphoribosyltransferase |
| 213923_at | RAP2B, member of RAS oncogene family |
| 213947_s_at | Rho-related BTB domain containing 2 [BLAST] |
| 213977_s_at | neuronal guanine nucleotide exchange factor |
| 213998_s_at | DEAD/H (Asp-Glu-Ala-Asp/His) box polypeptide 17 (72 kD) |
| 214020_x_at | integrin, beta 5 |
| 214035_x_at | nuclear pore complex interacting protein |
| 214093_s_at | RNA polymerase I associated factor, 53 kD |
| 214097_at | ribosomal protein S21 |
| 214100_x_at | LUC7-like (*S. cerevisiae*) |
| 214113_s_at | RNA binding motif protein 8A |
| 214149_s_at | Consensus includes gb: AI252582 /FEA = EST /DB_XREF = gi: 3849111 /DB_XREF = est: qv25b02.x1 /CLONE = IMAGE: 1982571 /UG = Hs.24322 ATPase, H+ transporting, lysosomal (vacuolar proton pump) 9 kD |
| 214211_at | ferritin, heavy polypeptide 1 |
| 214239_x_at | zinc finger protein 144 (Mel-18) |
| 214246_x_at | cholinergic receptor, nicotinic, epsilon polypeptide |
| 214259_s_at | aldo-keto reductase family 7, member A2 (aflatoxin aldehyde reductase) |
| 214356_s_at | pumilio homolog 2 (*Drosophila*) |
| 214383_x_at | testis intracellular mediator protein |
| 214484_s_at | protease, serine, 16 (thymus) |
| 214500_at | H2A histone family, member Y |
| 214531_s_at | sorting nexin 1 |
| 214581_x_at | tumor necrosis factor receptor superfamily, member 21 |
| 214657_s_at | Consensus includes gb: AU134977 /FEA = EST /DB_XREF = gi: 10995516 /DB_XREF = est: AU134977 /CLONE = PLACE1000926 /UG = Hs.322149 Human clone 137308 mRNA, partial cds |
| 214679_x_at | Consensus includes gb: AL110227.1 /DEF = *Homo sapiens* mRNA; cDNA DKFZp434J194 (from clone DKFZp434J194). /FEA = mRNA /DB_XREF = gi: 5817165 /UG = Hs.323067 *Homo sapiens* mRNA; cDNA DKFZp434J194 (from clone . . . |
| 214753_at | Consensus includes gb: AW084068 /FEA = EST /DB_XREF = gi: 6039220 /DB_XREF = est: xc26c06.x1 /CLONE = IMAGE: 2585386 /UG = Hs.110630 Human BRCA2 region, mRNA sequence CG006 |
| 214870_x_at | Consensus includes gb: AC002045 /DEF = Human Chromosome 16 BAC clone CIT987SK-A-589H1 /FEA = mRNA_2 /DB_XREF = gi: 2951945 /UG = Hs.251928 nuclear pore complex interacting protein |
| 214911_s_at | Consensus includes gb: S78771.1 /DEF = NAT = CpG island-associated gene human, mRNA, 1741 nt. /FEA = mRNA /DB_XREF = gi: 244232 /UG = Hs.75243 bromodomain-containing 2 |
| 214919_s_at | baculoviral IAP repeat-containing 6 (apollon) |
| 215001_s_at | glutamate-ammonia ligase (glutamine synthase) |
| 215089_s_at | Protein tyrosine phosphatase, receptor type, epsilon polypeptide |
| 215210_s_at | dihydrolipoamide S-succinyltransferase (E2 component of 2-oxo-glutarate complex) |
| 215235_at | spectrin, alpha, non-erythrocytic 1 (alpha-fodrin) |
| 215245_x_at | fragile X mental retardation 1 [BLAST] |
| 215464_s_at | phosphoinositide-3-kinase, regulatory subunit 4, p150 |
| 215482_s_at | PRP31 pre-mRNA processing factor 31 homolog (yeast) |
| 215498_s_at | mitogen-activated protein kinase kinase 3 |
| 215690_x_at | GPAA1P anchor attachment protein 1 homolog (yeast) |
| 215696_s_at | aryl-hydrocarbon receptor nuclear translocator 2 |
| 215731_s_at | M-phase phosphoprotein 9 |
| 215735_s_at | tuberous sclerosis 2 |
| 215807_s_at | plexin B1 |
| 215823_x_at | Consensus includes gb: U64661 /DEF = Human poly(A)-binding protein processed pseudogene3 /FEA = mRNA /DB_XREF = gi: 1519214 /UG = Hs.283767 poly(A)-binding protein, cytoplasmic, pseudogene 3 |
| 215884_s_at | ubiquilin 2 |
| 216033_a_at | chromosome 20 open reading frame 100 |
| 216237_s_at | MCM5 minichromosome maintenance deficient 5, cell division cycle 46 (*S. cerevisiae*) [BLAST] |
| 216264_s_at | laminin, beta 2 (laminin S) |
| 216384_x_at | Consensus includes gb: AF257099 /DEF = *Homo sapiens* prothymosin alpha (PTMA) gene, complete cds /FEA = CDS /DB_XREF = gi: 8037944 /UG = Hs.283947 *Homo sapiens* prothymosin alpha (PTMA) gene, complete cds |
| 216457_s_at | pecanex-like 3 (*Drosophila*) |

TABLE 1-continued genes up-regulated at day 2

| Gene Name | Gene Description |
| --- | --- |
| 216565_x_at | Consensus includes gb: AL121994 /DEF = Human DNA sequence from clone RP4-781L3 on chromosome 1p34.3-36.11 Contains a pseudogene similar to IFITM3 (interferon inducedntransmembrane protein 3 (1-8U), . . . |
| 216620_s_at | Rho guanine nucleotide exchange factor (GEF) 10 |
| 216894_x_at | Consensus includes gb: D64137 /DEF = Human KIP2 gene for Cdk-inhibitor p57KIP2, complete cds (exon1-4) /FEA = mRNA_4 /DB_XREF = gi: 992945 /UG = Hs.106070 cyclin-dependent kinase inhibitor 1C (p57, Kip2) |
| 216913_s_at | Rho-related BTB domain containing 2 [BLAST] |
| 216952_s_at | lamin B2 |
| 217028_at | chemokine (C-X-C motif), receptor 4 (fusin) [BLAST] |
| 217168_s_at | homocysteine-inducible, endoplasmic reticulum stress-inducible, ubiquitin-like domain member 1 |
| 217188_s_at | chromosome 14 open reading frame 1 |
| 217221_x_at | RNA binding motif protein 10 |
| 217301_x_at | retinoblastoma binding protein 4 |
| 217419_x_at | Consensus includes gb: AK021586.1 /DEF = *Homo sapiens* cDNA FLJ11524 fis, clone HEMBA1002547, highly similar to *Homo sapiens* agrin precursor mRNA. /FEA = mRNA /DB_XREF = gi: 10432794 /UG = Hs_273330 *Homo s* . . . |
| 217716_s_at | sorting nexin 11 [BLAST] |
| 217717_s_at | mitochondrial ribosomal protein L42 |
| 217718_s_at | mitochondrial ribosomal protein L42 |
| 217749_at | ring finger protein 12 |
| 217751_at | spastic paraplegia 3A (autosomal dominant) |
| 217755_at | hematological and neurological expressed 1 |
| 217759_at | sperm associated antigen 10 |
| 217767_at | complement component 3 |
| 217770_at | tripartite motif-containing 33 |
| 217779_s_at | zinc finger, DHHC domain containing 7 |
| 217794_at | TAF7-like RNA polymerase II, TATA box binding protein (TBP)-associated factor, 50 kD |
| 217807_s_at | glioma tumor suppressor candidate region gene 2 |
| 217809_at | G protein-coupled receptor kinase-interactor 1 |
| 217836_s_at | chromosome 20 open reading frame 44 |
| 217853_at | ATP synthase mitochondrial F1 complex assembly factor 1 [BLAST] |
| 217906_at | cyclin D-type binding-protein 1 |
| 217911_s_at | BCL2-associated athanogene 3 [BLAST] |
| 217914_at | nucleoporin 54 kD |
| 217918_at | ORM1-like 2 (*S. cerevisiae*) |
| 217957_at | ORM1-like 2 (*S. cerevisiae*) |
| 217964_at | elongation of very long chain fatty acids (FEN1/Elo2, SUR4/Elo3, yeast)-like 2 |
| 217969_at | chromosome 11 open reading frame2 |
| 217970_s_at | solute carrier family 12, (potassium-chloride transporter) member 5 |
| 217973_at | hydroxyacid oxidase 2 (long chain) |
| 217983_s_at | RTC domain containing 1 |
| 217984_at | RTC domain containing 1 |
| 218001_at | mitochondrial ribosomal protein S2 [BLAST] |
| 218010_x_at | chromosome 20 open reading frame 149 |
| 218019_s_at | FK506 binding protein 10 (65 kDa) |
| 218035_s_at | chromosome 20 open reading frame 16 |
| 218059_at | ribosomal protein L26-like 1 |
| 218076_s_at | solute carrier family 38, member 4 |
| 218083_at | prostaglandin E synthase 2 |
| 218090_s_at | gb: NM_018117.8 /DEF = *Homo sapiens* WD40 repeat domain 11 protein (WDR11), mRNA. /FEA = mRNA /GEN = WDR11 /PROD = WD40 repeat domain 11 protein /DB_XREF = gi: 13324687 /UG = Hs.16677 WD repeat domain 15 /FL = gb . . . |
| 218096_at | chromosome 20 open reading frame 46 |
| 218112_at | mitochondrial ribosomal protein S34 |
| 218123_at | chromosome 21 open reading frame 59 |
| 218135_at | toll-like receptor 7 |
| 218145_at | chromosome 20 open reading frame 97 |
| 218149_s_at | B-cell translocation gene 4 |
| 218180_s_at | RNA binding motif protein 15 |
| 218205_s_at | eukaryotic translation initiation factor 2 alpha kinase 4 |
| 218220_at | chromosome 12 open reading frame 10 |
| 218224_at | paraneoplastic antigen MA1 [BLAST] |
| 218228_s_at | tankyrase, TRF1-interacting ankyrin-related ADP-ribose polymerase 2 |
| 218229_s_at | myosin, heavy polypeptide 7B, cardiac muscle, beta |

TABLE 1-continued genes up-regulated at day 2

| Gene Name | Gene Description |
|---|---|
| 218241_at | golgi autoantigen, golgin subfamily a, 5 |
| 218244_at | FK506 binding protein 14 (22 kDa) |
| 218263_s_at | ras homolog gene family, member U |
| 218294_s_at | PRP31 pre-mRNA processing factor 31 homolog (yeast) |
| 218315_s_at | chromosome 20 open reading frame 34 |
| 218317_x_at | ganglioside-induced differentiation-associated protein 1-like 1 |
| 218323_at | chromosome 15 open reading frame 12 |
| 218328_at | mitochondrial ribosomal protein S2 |
| 218366_x_at | WD repeat domain 13 |
| 218379_at | RNA binding motif protein 7 |
| 218388_at | 6-phosphogluconolactonase |
| 218391_at | dual specificity phosphatase 12 |
| 218415_at | vacuolar protein sorting 33B (yeast) |
| 218422_s_at | 3-oxoacid CoA transferase 2 |
| 218437_s_at | leucine zipper transcription factor-like 1 |
| 218443_s_at | DAZ associated protein 1 |
| 218448_at | chromosome 20 open reading frame 11 |
| 218450_at | heme binding protein 1 |
| 218494_s_at | SLC2A4 regulator |
| 218496_at | ribonuclease H1 pseudogene 1 |
| 218529_at | toll-like receptor 7 |
| 218592_s_at | cat eye syndrome chromosome region, candidate 5 [BLAST] |
| 218652_s_at | protein phosphatase 1, regulatory (inhibitor) subunit 14D |
| 218659_at | chromosome 20 open reading frame 36 |
| 218697_at | G-2 and S-phase expressed 1 |
| 218740_s_at | CDK5 regulatory subunit associated protein 3 |
| 218744_s_at | protein kinase C and casein kinase substrate in neurons 3 |
| 218755_at | RAB6 interacting, kinesin-like (rabkinesin6) |
| 218756_s_at | matrix metalloproteinase 28 |
| 218767_at | chromosome 12 open reading frame 5 |
| 218773_s_at | kinesin-associated protein 3 |
| 218796_at | chromosome 20 open reading frame 42 |
| 218821_at | aminopeptidase-like 1 |
| 218839_at | hairy/enhancer-of-split related with YRPW motif 1 |
| 218848_at | MEF2-interacting transcription repressor |
| 218856_at | mitochondrial ribosomal protein L35 |
| 218860_at | hypothetical protein, clone MTA.D02.090 |
| 218865_at | ATP synthase mitochondrial F1 complex assembly factor 1 |
| 218875_s_at | F-box only protein 5 [BLAST] |
| 218896_s_at | chromosome Y open reading frame 14 |
| 218908_at | alveolar soft part sarcoma chromosome region, candidate 1 |
| 218921_at | testicular cell adhesion molecule 1 |
| 218983_at | immediate early response 5 |
| 218986_s_at | aldehyde reductase (aldose reductase) like 6 |
| 219007_at | hypothetical protein FLJ13287 |
| 219041_s_at | pre-B lymphocyte gene 3 |
| 219053_s_at | epsin 3 |
| 219066_at | mitochondrial ribosomal protein S35 |
| 219117_s_at | FK506 binding protein 11 (19 kDa) |
| 219151_s_at | general transcription factor IIE, polypeptide 1 (alpha subunit, 56 kD) |
| 219165_at | arachidonate lipoxygenase 3 |
| 219166_at | mitochondrial ribosomal protein S18A |
| 219188_s_at | chromosome 20 open reading frame 40 |
| 219192_at | vacuolar protein sorting 11 (yeast) |
| 219203_at | chromosome 20 open reading frame 45 |
| 219357_at | mitochondrial ribosomal protein S28 |
| 219491_at | ganglioside-induced differentiation-associated protein 1-like 1 |
| 219534_x_at | cyclin-dependent kinase inhibitor 1C (p57, Kip2) |
| 219549_s_at | reticulon 3 |
| 219571_s_at | G protein-coupled receptor, family C, group 1, member B |
| 219763_at | zinc finger protein 317 |
| 219764_at | frizzled homolog 10 (*Drosophila*) |
| 219816_s_at | zinc finger, DHHC domain containing 4 |
| 219880_at | conserved intergenic sequence 2 |
| 219911_s_at | solute carrier family 21 (organic anion transporter), member 12 |
| 219914_at | endothelin converting enzyme-like 1 |
| 220079_s_at | pecanex-like 3 (*Drosophila*) |
| 220099_s_at | gb: NM_016007.1 /DEF = *Homo sapiens* CGI-59 protein (LOC51625), mRNA. /FEA = mRNA /GEN = LOC51625 /PROD = CGI-59 protein /DB_XREF = gi: 7706297 /UG = Hs.279867 CGI-59 protein /FL = gb: AF151817.1 gb: NM_016007.1 |

TABLE 1-continued genes up-regulated at day 2

| Gene Name | Gene Description |
| --- | --- |
| 220212_s_at | neuromedin U |
| 220597_s_at | bridging integrator 3 |
| 220690_s_at | EGF-like-domain, multiple 6 |
| 220748_s_at | serine (or cysteine) proteinase inhibitor, clade A (alpha-1 antiproteinase, antitrypsin), member 10 |
| 220925_at | transgene insertion A2, Pierre Coulombe |
| 220954_s_at | solute carrier family 2, (facilitated glucose transporter) member 8 |
| 221050_s_at | GTP binding protein 2 |
| 221203_s_at | hypoxia-inducible factor 1, alpha subunit inhibitor |
| 221264_s_at | Alpha1,2-fucosyltransferase a [BLAST] |
| 221269_s_at | SH3 domain binding glutamic acid-rich protein like 3 [BLAST] |
| 221500_s_at | syntaxin 16 |
| 221501_x_at | nuclear pore complex interacting protein |
| 221509_at | density-regulated protein |
| 221562_s_at | sirtuin silent mating type information regulation 2 homolog 3 (*S. cerevisiae*) |
| 221619_s_at | ATP-binding cassette, sub-family D (ALD), member 1, pseudogene 1 |
| 221647_s_at | DEAD/H (Asp-Glu-Ala-Asp/His) box polypeptide 35 |
| 221689_s_at | Down syndrome critical region gene 5 |
| 221699_s_at | ganglioside-induced differentiation-associated protein 1-like 1 [BLAST] |
| 221712_s_at | protocadherin beta 17 pseudogene [BLAST] |
| 221725_at | WAS protein family, member 2 |
| 221741_s_at | chromosome 20 open reading frame 21 |
| 221746_at | ubiquitin-like 4 |
| 221759_at | ribosomal protein S4-like 2 |
| 221766_s_at | Consensus includes gb: AW246673 /FEA = EST /DB_XREF = gi: 6589666 /DB_XREF = est: 2821951.3prime /CLONE = IMAGE: 2821951 /UG = Hs.10784 hypothetical protein FLJ20037 |
| 221786_at | Consensus includes gb: BF197222 /FEA = EST /DB_XREF = gi: 11085906 /DB_XREF = est: 7m88b07.x1 /CLONE = IMAGE: 3561949 /UG = Hs.12342 *Homo sapiens* clone 24538 mRNA sequence |
| 221789_x_at | solute carrier family 25 (mitochondrial oxodicarboxylate carrier), member 21 |
| 221816_s_at | ankyrin repeat and SOCS box-containing 3 [BLAST] |
| 221827_at | chromosome 20 open reading frame 18 |
| 221919_at | heterogeneous nuclear ribonucleoprotein A1 |
| 221931_s_at | chromosome 20 open reading frame 150 |
| 221932_s_at | insulin-like growth factor 2, antisense |
| 221989_at | ribosomal protein L10 |
| 222010_at | acetyl-Coenzyme A acetyltransferase 2 (acetoacetyl Coenzyme A thiolase) |
| 222011_s_at | acetyl-Coenzyme A acetyltransferase 2 (acetoacetyl Coenzyme A thiolase) |
| 222037_at | MCM4 minichromosome maintenance deficient 4 (*S. cerevisiae*) |
| 222040_at | heterogeneous nuclear ribonucleoprotein A1 |
| 222122_s_at | retinoic acid induced 17 [BLAST] |
| 222131_x_at | solute carrier family 25 (mitochondrial oxodicarboxylate carrier), member 21 |
| 222154_s_at | golgi reassembly stacking protein 2, 55 kDa |
| 222155_s_at | chromosome 1 open reading frame 28 |
| 222206_s_at | p21(CDKN1A)-activated kinase 6 |
| 222369_at | ribosomal protein L36a |

TABLE 2 genes up-regulated at day 5

| Gene Name | Gene Description |
| --- | --- |
| 200000_s_at | PRP8 pre-mRNA processing factor 8 homolog (yeast) |
| 200023_s_at | eukaryotic translation initiation factor 3, subunit 5 (epsilon, 47 kD) |
| 200044_at | splicing factor, arginine/serine-rich 9 |
| 200047_s_at | YY1 transcription factor |
| 200055_at | TAF10 RNA polymerase II, TATA box binding protein (TBP)-associated factor, 30 kD |
| 200069_at | squamous cell carcinoma antigen recognised by T cells 3 |
| 200071_at | sin3-associated polypeptide, 18 kD |

TABLE 2-continued genes up-regulated at day 5

| Gene Name | Gene Description |
| --- | --- |
| 200083_at | ubiquitin specific protease 22 |
| 31874_at | growth arrest-specific 2 like 1 |
| 32137_at | jagged 2 |
| 33132_at | cleavage and polyadenylation specific factor 1, 160 kD subunit |
| 33322_i_at | stratifin |
| 34764_at | activity-dependent neuroprotector |
| 36553_at | acetylserotonin O-methyltransferase-like |
| 37462_i_at | splicing factor 3a, subunit 2, 66 kD |
| 37652_at | ribosomal protein L13a |
| 38157_at | dom-3 homolog Z (C. elegans) |
| 39248_at | aquaporin 3 |
| 39729_at | peroxiredoxin 2 [BLAST] |
| 39835_at | SET binding factor 1 |
| 40465_at | fatty acid desaturase 2 |
| 40472_at | peroxisomal farnesylated protein |
| 41047_at | chromosome 9 open reading frame 16 |
| 41858_at | RAB30, member RAS oncogene family [BLAST] |
| 44111_at | vacuolar protein sorting 33B (yeast) |
| 44654_at | ribosomal protein S4-like 2 |
| 44696_at | protocadherin beta 17 pseudogene |
| 46665_at | sema domain, immunoglobulin domain (Ig), transmembrane domain (TM) and short cytoplasmic domain, (semaphorin) 4C |
| 47069_at | Rho GTPase activating protein 8 |
| 47083_at | prion protein interacting protein |
| 50314_i_at | chromosome 20 open reading frame 27 |
| 52164_at | chromosome 11 open reading frame 24 |
| 53071_s_at | hypothetical protein FLJ22222 |
| 59625_at | nucleolar protein 3 (apoptosis repressor with CARD domain) |
| 55872_at | solute carrier family 12, (potassium-chloride transporter) member 5 |
| 60474_at | chromosome 20 open reading frame 42 |
| 64474_g_at | RNA binding motif protein 15 |
| 65884_at | mannosidase, alpha, class 1B, member 1 |
| 91703_at | integrin, beta 1 (fibronectin receptor, beta polypeptide, antigen CD29 includes MDF2, MSK12) |
| 200593_s_at | gb: BC003621.1 /DEF = Homo sapiens, heterogeneous nuclear ribonucleoprotein U (scaffold attachment factor A), clone MGC: 1992, mRNA, complete cds. /FEA = mRNA /PROD = heterogeneous nuclear ribonucleopro . . . |
| 200618_at | LIM and SH3 protein 1 |
| 200619_at | splicing factor 3b, subunit 2, 145 kD |
| 200637_s_at | protein tyrosine phosphatase, receptor type, F |
| 200655_s_at | calmodulin 1 (phosphorylase kinase, delta) |
| 200675_at | CD81 antigen (target of antiproliferative antibody 1) |
| 200702_s_at | DEAD/H (Asp-Glu-Ala-Asp/His) box polypeptide 24 [BLAST] |
| 200707_at | protein kinase C substrate 80K—H |
| 200710_at | acyl-Coenzyme A dehydrogenase, very long chain |
| 200743_s_at | ceroid-lipofuscinosis, neuronal 2, late infantile (Jansky-Bielschowsky disease) |
| 200747_s_at | nuclear mitotic apparatus protein 1 |
| 200766_at | cathepsin D (lysosomal aspartyl protease) |
| 200810_s_at | cold inducible RNA binding protein |
| 200816_s_at | platelet-activating factor acetylhydrolase, isoform Ib, alpha subunit (45 kD) |
| 200827_at | procollagen-lysine, 2-oxoglutarate 5-dioxygenase (lysine hydroxylase, Ehlers-Danlos syndrome type VI) |
| 200864_s_at | RAB11A, member RAS oncogene family |
| 200867_at | zinc finger protein 313 |
| 200875_s_at | nucleolar protein 5A (56 kD with KKE/D repeat) |
| 200884_at | creatine kinase, brain |
| 200891_s_at | signal sequence receptor, alpha (translocon-associated protein alpha) |
| 200903_s_at | S-adenosylhomocysteine hydrolase |
| 200914_x_at | kinectin 1 (kinesin receptor) |
| 200918_s_at | signal recognition particle receptor ('docking protein') |
| 200950_at | actin related protein 2/3 complex, subunit 1A (41 kD) |
| 200959_at | fusion, derived from t(12; 16) malignant liposarcoma |
| 200965_s_at | actin binding LIM protein |
| 200967_at | peptidylprolyl isomerase B (cyclophilin B) |
| 200968_s_at | peptidylprolyl isomerase B (cyclophilin B) |
| 200980_s_at | pyruvate dehydrogenase (lipoamide) alpha 1 |
| 200990_at | gb: NM_005762.1 /DEF = Homo sapiens KRAB-associated protein 1 (TIF1B), mRNA. /FEA = mRNA /GEN = TIF1B /PROD = KRAB-associated protein 1 |

TABLE 2-continued genes up-regulated at day 5

| Gene Name | Gene Description |
|---|---|
| | /DB_XREF = gi: 5032178 /UG = Hs.228059 KRAB-associated protein 1 /FL = gb: B . . . |
| 201003_x_at | gb: NM_003349.2 /DEF = Homo sapiens ubiqtiitin-conjugating enzyme E2 variant 1 (UBE2V1), transcript variant 2, mRNA. /FEA = mRNA /GEN = UBE2V1 /PROD = ubiquitin-conjugating enzyme E2 variant 1, isoform b / . . . |
| 201008_s_at | thioredoxin interacting protein |
| 201011_at | ribophorin I |
| 201015_s_at | junction plakoglobin |
| 201024_x_at | Consensus includes gb: BG261322 /FEA = EST /DB_XREF = gi: 12771138 /DB_XREF = est: 602373079F1 /CLONE = IMAGE: 4484563 /UG = Hs.158688 KIAA0741 gene product /FL = gb: AB018284.1 gb: AF078035.1 gb: NM_015904.1 |
| 201034_at | L-3-hydroxyacyl-Coenzyme A dehydrogenase, short chain |
| 201037_at | phosphofructokinase, platelet |
| 201052_s_at | proteasome (prosome, macropain) inhibitor subunit 1 (PI31) |
| 201054_at | heterogeneous nuclear ribonucleoprotein A0 [BLAST] |
| 201064_s_at | poly(A) binding protein, cytoplasmic 4 (inducible form) |
| 201065_s_at | general transcription factor II, i [BLAST] |
| 201074_at | SWI/SNF related, matrix associated, actin dependent regulator of chromatin, subfamily c, member 1 |
| 201079_at | synaptogyrin 2 |
| 201082_s_at | dynactin 1 (p150, glued homolog, Drosophila) |
| 201102_s_at | phosphofructokinase, liver |
| 201113_at | Tu translation elongation factor, mitochondrial |
| 201128_s_at | ATP citrate lyase |
| 201129_at | gb: NM_006276.2 /DEF = Homo sapiens splicing factor, arginineserine-rich 7 (35 kD) (SFRS7), mRNA. /FEA = mRNA /GEN = SFRS7 /PROD = splicing factor, arginineserine-rich 7 (35 kD) /DB_XREF = gi: 6857827 /UG = Hs. . . . |
| 201160_s_at | cold shock domain protein A |
| 201161_s_at | cold shock domain protein A |
| 201176_s_at | archain 1 |
| 201188_s_at | inositol 1,4,5-triphosphate receptor, type 3 |
| 201189_s_at | inositol 1,4,5-triphosphate receptor, type 3 |
| 201198_s_at | proteasome (prosome, macropain) 26S subunit, non-ATPase, 1 |
| 201209_at | histone-deacetylase 1 |
| 201244_s_at | v-raf-1 murine leukemia viral oncogene homolog 1 |
| 201247_at | sterol regulatory element binding transcription factor 2 |
| 201255_x_at | HLA-B associated transcript 3 |
| 201264_at | coatomer protein complex, subunit epsilon |
| 201271_s_at | RNA binding protein (autoantigenic, hnRNP-associated with lethal yellow) |
| 201296_s_at | golgi associated, gamma adaptin ear containing, ARF binding protein 1 |
| 201310_s_at | Kruppel-like factor 4 (gut) |
| 201313_at | gb: NM_001975.1 /DEF = Homo sapiens enolase 2, (gamma, neuronal) (ENO2), mRNA. /FEA = mRNA /GEN = ENO2 /PROD = enolase 2, (gamma, neuronal) /DB_XREF = gi: 5803010 /UG = Hs.146580 enolase 2, (gamma, neuronal) / . . . |
| 201315_x_at | interferon induced transmembrane protein 2 (1-8D) |
| 201331_s_at | signal transducer and activator of transcription-6, interleukin-4 induced |
| 201356_at | splicing factor 3a, subunit 1, 120 kD |
| 201360_at | cystatin C (amyloid angiopathy and cerebral hemorrhage) |
| 201362_at | polymerase (RNA) III (DNA directed) polypeptide F (39 kD) |
| 201363_s_at | polymerase (RNA) III (DNA directed) polypeptide F (39 kD) |
| 201373_at | plectin 1, intermediate filament binding protein, 500 kD |
| 201379_s_at | tumor protein D52-like 2 |
| 201413_at | hydroxysteroid (17-beta) dehydrogenase 4 |
| 201440_at | fatty acid desaturase 2 |
| 201448_at | TIA1 cytotoxic granule-associated RNA binding protein |
| 201454_s_at | Consensus includes gb: AW055008 /FEA = EST /DB_XREF = gi: 5920711 /DB_XREF = est: wy98c09.x1 /CLONE = IMAGE: 2556592 /UG = Hs.293007 aminopeptidase puromycin sensitive /FL = gb: NM_006310.1 |
| 201459_at | RuvB-like 2 (E. coli) |
| 201482_at | quiescin Q6 |
| 201489_at | peptidylprolyl isomerase F (cyclophilin F) |
| 201498_at | ubiquitin specific protease 7 (herpes virus-associated) |
| 201526_at | ADP-ribosylation factor 5 |
| 201545_s_at | poly(A) binding protein, nuclear 1 |
| 201555_at | MCM3 minichromosome maintenance deficient 3 (S. cerevisiae) |
| 201564_s_at | singed-like (fascin homolog, sea urchin) (Drosophila) |
| 201578_at | podocalyxin-like |

TABLE 2-continued genes up-regulated at day 5

| Gene Name | Gene Description |
|---|---|
| 201585_s_at | splicing factor proline/glutamine rich (polypyrimidine tract binding protein associated) |
| 201586_s_at | splicing factor proline/glutamine rich (polypyrimidine tract binding protein associated) |
| 201598_s_at | inositol polyphosphate phosphatase-like 1 |
| 201601_x_at | interferon induced transmembrane protein 1 (9-27) |
| 201612_at | aldehyde dehydrogenase 9 family, member A1 |
| 201620_at | membrane-bound transcription factor protease, site 1 |
| 201623_s_at | aspartyl-tRNA synthetase |
| 201624_at | aspartyl-tRNA synthetase |
| 201639_s_at | cleavage and polyadenylation specific factor 1, 160 kD subunit |
| 201643_x_at | chromosome 5 open reading frame 7 |
| 201645_at | tenascin C (hexabrachion) |
| 201650_at | keratin 19 |
| 201675_at | A kinase (PRKA) anchor protein 1 |
| 201679_at | tripartite motif-containing 33 |
| 201689_s_at | tumor protein D52 |
| 201690_s_at | tumor protein D52 |
| 201697_s_at | DNA (cytosine-5-)-methyltransferase 1 |
| 201704_at | ectonucleoside triphosphate diphosphohydrolase 6 (putative function) |
| 201714_at | tubulin, gamma 1 |
| 201719_s_at | erythrocyte membrane protein band 4.1-like 2 |
| 201726_at | ELAV (embryonic lethal, abnormal vision, *Drosophila*)-like 1 (Hu antigen R) |
| 201746_at | tumor protein p53 (Li-Fraumeni syndrome) |
| 201747_s_at | scaffold attachment factor B |
| 201790_s_at | 7-dehydrocholesterol reductase |
| 201795_at | lamin B receptor |
| 201818_at | brain and acute leukemia, cytoplasmic |
| 201828_x_at | CAAX box 1 |
| 201833_at | histone deacetylase 2 |
| 201841_s_at | heat shock 27 kD protein 1 |
| 201853_s_at | cell division cycle 25B |
| 201885_s_at | diaphorase (NADH) (cytochrome b-5 reductase) |
| 201889_at | family with sequence similarity 3, member C |
| 201928_at | plakophilin 4 |
| 201937_s_at | aspartyl aminopeptidase |
| 201970_s_at | nuclear autoantigenic sperm protein (histone-binding) |
| 202039_at | TGFB1-induced anti-apoptotic factor 1 |
| 202043_s_at | spermine synthase |
| 202060_at | Rho guanine nucleotide exchange factor (GEF) 10 |
| 202066_at | protein tyrosine phosphatase, receptor type, f polypeptide (PTPRF), interacting protein (liprin), alpha 1 |
| 202097_at | nucleoporin 153 kD |
| 202104_s_at | spastic paraplegia 7, paraplegin (pure and complicated autosomal recessive) |
| 202115_s_at | ATP-binding cassette, sub-family A (ABC1), member 12 |
| 202119_s_at | copine III |
| 202127_at | myotubularin related protein 2 |
| 202130_at | sudD suppressor of bimD6 homolog (*A. nidulans*) |
| 202133_at | centaurin, beta 2 |
| 202136_at | S-adenosylhomocysteine hydrolase-like 1 |
| 202139_at | aldo-keto reductase family 7, member A2 (aflatoxin aldehyde reductase) |
| 202151_s_at | CD2 antigen (cytoplasmic tail) binding protein 2 |
| 202159_at | phenylalanine-tRNA synthetase-like |
| 202161_at | protein kinase C-like 1 |
| 202171_at | zinc finger protein 161 |
| 202180_s_at | major vault protein |
| 202182_at | GCN5 general control of amino-acid synthesis 5-like 2 (yeast) |
| 202189_x_at | polypyrimidine tract binding protein 1 [BLAST] |
| 202219_at | solute carrier family 6 (neurotransmitter transporter, creatine), member 8 |
| 202220_at | calsyntenin 1 |
| 202228_s_at | dynein, axonemal, intermediate polypeptide 1 |
| 202230_s_at | calcium homeostasis endoplasmic reticulum protein |
| 202240_at | polo-like kinase (*Drosophila*) |
| 202241_at | growth differentiation factor 11 |
| 202251_at | PRP4 pre-mRNA processing factor 4 homolog (yeast) |
| 202275_at | glucose-6-phosphate dehydrogenase |
| 202289_s_at | transforming, acidic coiled-coil containing protein 2 |
| 202308_at | sterol regulatory element binding transcription factor 1 |

TABLE 2-continued genes up-regulated at day 5

| Gene Name | Gene Description |
|---|---|
| 202320_at | general transcription factor IIIC, polypeptide 1 (alpha subunit, 220 kD) |
| 202344_at | heat shock transcription factor 1 |
| 202357_s_at | B-factor, properdin [BLAST] |
| 202384_s_at | Treacher Collins-Franceschetti syndrome 1 |
| 202409_at | insulin-like growth factor 2 (somatomedin A) |
| 202411_at | interferon, alpha-inducible protein 27 |
| 202424_at | mitogen-activated protein kinase kinase 2 |
| 202430_s_at | phospholipid scramblase 1 |
| 202446_s_at | phospholipid scramblase 1 |
| 202464_s_at | 6-phosphofructo-2-kinase/fructose-2,6-biphosphatase 3 |
| 202478_at | immunoglobulin kappa joining 1 |
| 202510_s_at | tumor necrosis factor, alpha-induced protein 2 |
| 202534_x_at | dihydrofolate reductase |
| 202536_at | EGF-like-domain, multiple 6 |
| 202540_s_at | 3-hydroxy-3-methylglutaryl-Coenzyme A reductase |
| 202569_s_at | MAP/microtubule affinity-regulating kinase 3 |
| 202589_at | thymidylate synthetase |
| 202605_at | glucuronidase, beta |
| 202686_s_at | AXL receptor tyrosine kinase |
| 202715_at | carbamoyl-phosphate synthetase 2, aspartate transcarbamylase, and dihydroorotase |
| 202718_at | insulin-like growth factor binding protein 2 (36 kD) |
| 202757_at | rotatin |
| 202804_at | ATP-binding cassette, sub-family C (CFTR/MRP), member 1 |
| 202809_s_at | down-regulated in colon cancer 1 |
| 202812_at | glucosidase, alpha; acid (Pompe disease, glycogen storage disease type II) |
| 202836_s_at | mannosidase, alpha, class 1A, member 2 |
| 202853_s_at | RYK receptor-like tyrosine kinase |
| 202870_s_at | CDC20 cell division cycle 20 homolog (*S. cerevisiae*) |
| 202890_at | Consensus includes gb: AW242297 /FEA = EST /DB_XREF = gi: 6576051 /DB_XREF = est: xm96b11.x1 /CLONE = IMAGE: 2692029 /UG = Hs.146388 microtubule-associated protein 7 /FL = gb: NM_003980.1 |
| 202917_s_at | S100 calcium binding protein A8 (calgranulin A) |
| 202929_s_at | D-dopachrome tautomerase |
| 202934_at | hexokinase 2 [BLAST] |
| 202936_s_at | SRY (sex determining region Y)-box 9 (campomelic dysplasia, autosomal sex-reversal) |
| 202951_at | serine/threonine kinase 38 |
| 202962_at | kinesin family member 13B |
| 202979_s_at | ras homolog gene family, member U |
| 202998_s_at | lysyl oxidase-like 2 |
| 203021_at | secretory leukocyte protease inhibitor (antileukoproteinase) [BLAST] |
| 203062_s_at | heparan sulfate 2-O-sulfotransferase 1 |
| 203065_s_at | caveolin 1, caveolae protein, 22 kD [BLAST] |
| 203067_at | cysteine and glycine-rich protein 3 (cardiac LIM protein) |
| 203098_at | chromodomain protein, Y chromosome-like |
| 203102_s_at | mannosyl (alpha-1,6-)-glycoprotein beta-1,2-N-acetylglucosaminyltransferase |
| 203103_s_at | HIV TAT specific factor 1 |
| 203108_at | retinoic acid induced 3 |
| 203124_s_at | solute carrier family 11 (proton-coupled divalent metal ion transporters), member 2 |
| 203126_at | inositol(myo)-1(or 4)-monophosphatase 2 |
| 203137_at | M-phase phosphoprotein 1 |
| 203153_at | interferon-induced protein with tetratricopeptide repeats 1 |
| 203155_at | SET domain, bifurcated 1 |
| 203184_at | fibrillin 2 (congenital contractural arachnodactyly) |
| 203189_s_at | NADH dehydrogenase (ubiquinone) Fe—S protein 8 (23 kD) (NADH-coenzyme Q reductase) |
| 203198_at | cyclin-dependent kinase 9 (CDC2-related kinase) [BLAST] |
| 203219_s_at | adenine phosphoribosyltransferase |
| 203224_at | chromosome 20 open reading frame 38 |
| 203234_at | uridine phosphorylase |
| 203244_at | peroxisome receptor 1 |
| 203252_at | gb: NM_005851.1 /DEF = *Homo sapiens* tumor suppressor deleted in oral cancer-related 1 (DOC-1R), mRNA. /FEA = mRNA /GEN = DOC-1R /PROD = tumor suppressor deleted in oral cancer-related1 /DB_XREF = gi: 503166 . . . |
| 203262_s_at | DNA segment on chromosome X (unique) 9928 expressed sequence |
| 203276_at | lamin B1 |

TABLE 2-continued genes up-regulated at day 5

| Gene Name | Gene Description |
|---|---|
| 203282_at | glucan (1,4-alpha-), branching enzyme 1 (glycogen branching enzyme, Andersen disease, glycogen storage disease type IV) |
| 203286_at | Rho-related BTB domain containing 3 |
| 203338_at | protein phosphatase 2, regulatory subunit B (B56)-, epsilon isoform |
| 203386_at | chromosome 21 open reading frame 108 |
| 203391_at | gb: NM_004470.1 /DEF = Homo sapiens FK506-binding protein 2 (13 kD) (FKBP2), mRNA. /FEA = mRNA /GEN = FKBP2 /PROD = FK506-binding protein 2 (13 kD) /DB_XREF = gi: 4758381 /UG = Hs.227729 FK506-binding protein 2 . . . |
| 203417_at | microfibrillar-associated protein 2 |
| 203439_s_at | stanniocalcin 2 |
| 203477_at | collagen, type XV, alpha 1 |
| 203482_at | zinc finger protein 334 |
| 203495_at | syndecan 3 (N-syndecan) |
| 203552_at | mitogen-activated protein kinase kinase kinase kinase 5 [BLAST] |
| 203564_at | Fanconi anemia, complementation group G |
| 203612_at | bystin-like [BLAST] |
| 203683_s_at | vascular endothelial growth factor B |
| 203701_s_at | chromosome 20 open reading frame 13 |
| 203739_at | zinc finger protein 217 |
| 203767_s_at | steroid sulfatase (microsomal), arylsulfatase C, isozyme S |
| 203775_at | solute carrier family 25, member 13 (citrin) |
| 203802_x_at | LUC7-like (S. cerevisiae) |
| 203818_s_at | splicing factor 3a, subunit 3, 60 kD |
| 203825_at | bromodomain containing 3 |
| 203828_s_at | zinc finger protein 206 |
| 203831_at | [BLAST] |
| 203848_at | A kinase (PRKA) anchor protein 8 |
| 203867_s_at | toll interacting protein |
| 203919_at | transcription elongation factor A (SII), 2 |
| 203955_at | GRB2-associated binding protein 2 |
| 203974_at | synapsin III |
| 203976_s_at | chromatin assembly factor 1, subunit A (p150) |
| 204022_at | abhydrolase domain containing 1 |
| 204030_s_at | schwannomin interacting protein 1 |
| 204058_at | malic enzyme 1, NADP(+)-dependent, cytosolic |
| 204133_at | cyclin E2 |
| 204136_at | collagen, type VII, alpha 1 (epidermolysis bullosa, dystrophic, dominant and recessive) |
| 204142_at | SRY (sex determining region Y)-box 6 |
| 204143_s_at | SRY (sex determining region Y)-box 6 |
| 204178_s_at | RNA binding motif protein 14 |
| 204224_s_at | GTP cyclohydrolase 1 (dopa-responsive dystonia) |
| 204238_s_at | secretagogin, EF-hand calcium binding protein |
| 204274_at | Consensus includes gb: AA812215 /FEA = EST /DB_XREF = gi: 2881826 /DB_XREF = est: ob84g01.s1 /CLONE = IMAGE: 1338096 /UG = Hs.9222 estrogen receptor binding site associated, antigen, 9 /FL = gb: BC005249.1 gb: AF0 . . . |
| 204275_at | small optic lobes homolog (Drosophila) |
| 204295_at | surfeit 1 |
| 204372_s_at | KH-type splicing regulatory protein (FUSE binding protein 2) |
| 204383_at | clathrin, heavy polypeptide-like 1 |
| 204401_at | potassium intermediate/small conductance calcium-activated channel, subfamily N, member 4 |
| 204409_s_at | eukaryotic translation initiation factor 1A, Y chromosome |
| 204475_at | matrix metalloproteinase 1 (interstitial collagenase) |
| 204480_s_at | chromosome 9 open reading frame 16 |
| 204520_x_at | bromodomain containing 1 |
| 204521_at | cleavage and polyadenylation specific factor 1, 160 kD subunit |
| 204531_s_at | breast cancer 1, early onset |
| 204617_s_at | aquaporin 9 |
| 204698_at | interferon stimulated gene (20 kD) |
| 204717_s_at | solute carrier family 29 (nucleoside transporters), member 2 |
| 204808_s_at | transmembrane protein 5 |
| 204839_at | membrane-bound transcription factor protease, site 2 |
| 204849_at | transcription factor-like 5 (basic helix-loop-helix) |
| 204857_at | MAD1 mitotic arrest deficient-like 1 (yeast) |
| 204858_s_at | endothelial cell growth factor 1 (platelet-derived) |
| 204875_s_at | GDP-mannose 4,6-dehydratase |
| 204908_s_at | B-cell CLL/lymphoma 3 |

TABLE 2-continued genes up-regulated at day 5

| Gene Name | Gene Description |
| --- | --- |
| 204990_s_at | integrin, beta 4 |
| 205000_at | DEAD/H (Asp-Glu-Ala-Asp/His) box polypeptide, Y chromosome |
| 205053_at | primase, polypeptide 1 (49 kD) |
| 205068_s_at | paternally expressed 10 |
| 205155_s_at | spectrin, beta, non-erythrocytic 2 |
| 205199_at | carbonic anhydrase IX |
| 205202_at | protein-L-isoaspartate (D-aspartate) O-methyltransferase |
| 205353_s_at | prostatic binding protein |
| 205382_s_at | D component of complement (adipsin) |
| 205412_at | acetyl-Coenzyme A acetyltransferase 1 (acetoacetyl Coenzyme A thiolase) |
| 205436_s_at | H2A histone family, member X |
| 205449_at | cleavage and polyadenylation specific factor 1, 160 kD subunit |
| 205501_at | phosphodiesterase 10A |
| 205516_x_at | neuronal guanine nucleotide exchange factor |
| 205527_s_at | gem (nuclear organelle) associated protein 4 |
| 205534_at | BH-protocadherin (brain-heart) [BLAST] |
| 205546_s_at | tyrosine kinase 2 |
| 205552_s_at | 2',5'-oligoadenylate synthetase 1 (40-46 kD) |
| 205565_s_at | Friedreich ataxia |
| 205583_s_at | NIMA (never in mitosis gene a)-related kinase 11 |
| 205658_s_at | small nuclear RNA activating complex, polypeptide 4, 190 kD |
| 205780_at | BCL2-interacting/killer (apoptosis-inducing) |
| 205961_s_at | gb: NM_004682.1 /DEF = Homo sapiens PC4 and SFRS1 interacting protein 2 (PSIP2), mRNA. /FEA = mRNA /GEN = PSIP2 /PROD = PC4 and SFRS1 interacting protein 2 /DB_XREF = gi: 4758869 /UG = Hs.306179 PC4 and SFRS1 . . . |
| 206023_at | neuromedin U |
| 206095_s_at | gb: NM_006625.2 /DEF = Homo sapiens TLS-associated serine-arginine protein 1 (TASR1), mRNA. /FEA = mRNA /GEN = TASR1 /PROD = TLS-associated serine-arginine protein 1 /DB_XREF = gi: 12056474 /UG = Hs.288038 TL . . . |
| 206102_at | tripartite motif-containing 14 |
| 206200_s_at | annexin A11 |
| 206332_s_at | interferon, gamma-inducible protein 16 |
| 206499_s_at | chromosome condensation 1 |
| 206785_s_at | killer cell lectin-like receptor subfamily C, member 2 |
| 206809_s_at | heterogeneous nuclear ribonucleoprotein A3 |
| 207002_s_at | pleiomorphic adenoma gene-like 1 |
| 207076_s_at | argininosuccinate synthetase [BLAST] |
| 207122_x_at | sulfotransferase family, cytosolic, 1A, phenol-preferring, member 2 |
| 207140_at | alkaline phosphatase, intestinal |
| 207165_at | hyaluronan-mediated motility receptor (RHAMM) |
| 207196_s_at | UDP-Gal: betaGlcNAc beta 1,3-galactosyltransferase, polypeptide 5 |
| 207414_s_at | paired basic amino acid cleaving system 4 |
| 207564_x_at | O-linked N-acetylglucosamine (GlcNAc) transferase (UDP-N-acetylglucosamine:polypeptide-N-acetylglucosaminyl transferase) |
| 207622_s_at | ATP-binding cassette, sub-family F (GCN20), member 2 |
| 207714_s_at | serine (or cysteine) proteinase inhibitor, clade H (heat shock protein 47), member 1, (collagen binding protein 1) |
| 207723_s_at | killer cell lectin-like receptor subfamily C, member 3 |
| 207760_s_at | nuclear receptor co-repressor 2 |
| 207761_s_at | component of oligomeric golgi complex 4 |
| 207824_s_at | MYC-associated zinc finger protein (purine-binding transcription factor) |
| 207831_x_at | deoxyhypusine synthase |
| 207842_s_at | zyxin [BLAST] |
| 207847_s_at | mucin 1, transmembrane |
| 208072_s_at | diacylglycerol kinase, delta (130 kD) |
| 208149_x_at | DEAD/H (Asp-Glu-Ala-Asp/His) box polypeptide 11 (CHL1-like helicase homolog, S. cerevisiae) [BLAST] |
| 208152_s_at | gb: NM_004728.1 /DEF = Homo sapiens DEADH (Asp-Glu-Ala-AspHis) box polypeptide 21 (DDX21), mRNA. /FEA = mRNA /GEN = DDX21 /PROD = DEADH (Asp-Glu-Ala-AspHis) box polypeptide 21 /DB_XREF = gi: 13787208 /FL = gb . . . |
| 208156_x_at | gb: NM_031308.1 /DEF = Homo sapiens epiplakin 1 (EPPK1), mRNA. /FEA = mRNA /GEN = EPPK1 /PROD = epiplakin 1 /DB_XREF = gi: 13876385 /FL = gb: NM_031308.1 |
| 208159_x_at | DEAD/H (Asp-Glu-Ala-Asp/His) box polypeptide 11 (CHL1-like helicase homolog, S. cerevisiae) |

TABLE 2-continued genes up-regulated at day 5

| Gene Name | Gene Description |
|---|---|
| 208248_x_at | amyloid beta (A4) precursor-like protein 2 |
| 208270_s_at | arginyl aminopeptidase (aminopeptidase B) |
| 208313_s_at | splicing factor 1 |
| 208336_s_at | glycoprotein, synaptic 2 |
| 208407_s_at | catenin (cadherin-associated protein), delta 1 |
| 208436_s_at | interferon regulatory factor 7 |
| 208617_s_at | protein tyrosine phosphatase type IVA, member 2 |
| 208621_s_at | villin 2 (ezrin) |
| 208625_s_at | eukaryotic translation initiation factor 4 gamma, 1 |
| 208636_at | actinin, alpha 1 |
| 208647_at | farnesyl-diphosphate farnesyltransferase 1 |
| 208655_at | cyclin I |
| 208676_s_at | chromosome 20 open reading frame 54 |
| 208700_s_at | transketolase (Wernicke-Korsakoff syndrome) |
| 208703_s_at | amyloid beta (A4) precursor-like protein 2 |
| 208713_at | protein tyrosine phosphatase, non-receptor type 21 |
| 208714_at | NADH dehydrogenase (ubiquinone) flavoprotein 1 (51 kD) |
| 208719_s_at | DEAD/H (Asp-Glu-Ala-Asp/His) box polypeptide 17 (72 kD) |
| 208729_x_at | major histocompatibility complex, class I, B |
| 208774_at | casein kinase 1, delta |
| 208794_s_at | SWI/SNF related, matrix associated, actin dependent regulator of chromatin, subfamily a, member 4 |
| 208804_s_at | splicing factor, arginine/serine-rich 6 |
| 208809_s_at | gb: AL136632.1 /DEF = *Homo sapiens* mRNA; cDNA DKFZp564G182 (from clone DKFZp564G182); complete cds. /FEA = mRNA /GEN = DKFZp564G182 /PROD = hypothetical protein /DB_XREF = gi: 12052789 /UG = Hs.173685 hypothe . . . |
| 208820_at | PTK2 protein tyrosine kinase 2 |
| 208858_s_at | WD repeat domain 7 |
| 208863_s_at | splicing factor, arginine/serine-rich 1 (splicing factor 2, alternate splicing factor) |
| 208880_s_at | chromosome 20 open reading frame 14 |
| 208890_s_at | plexin B2 |
| 208891_at | dual specificity phosphatase 6 |
| 208892_s_at | dual specificity phosphatase 6 |
| 208906_at | ligand of numb-protein X |
| 208912_s_at | gb: BC001362.1 /DEF = *Homo sapiens*, 2,3-cyclic nucleotide 3 phosphodiesterase, clone MGC: 2262, mRNA, complete cds. /FEA = mRNA /PROD = 2,3-cyclic nucleotide 3 phosphodiesterase /DB_XREF = gi: 12655028 /UG . . . |
| 208923_at | cytoplasmic FMR1 interacting protein 1 |
| 208928_at | P450 (cytochrome) oxidoreductase |
| 208930_s_at | interleukin enhancer binding factor 3, 90 kD |
| 208938_at | papillary renal cell carcinoma (translocation-associated) |
| 208968_s_at | aldo-keto reductase family 1, member B10 (aldose reductase) |
| 208978_at | cysteine-rich protein 2 |
| 208984_x_at | RNA binding motif protein 10 |
| 208998_at | uncoupling protein 2 (mitochondrial, proton carrier) |
| 209007_s_at | solute carrier family 17 (sodium-dependent inorganic phosphate cotransporter), member 7 |
| 209029_at | COP9 constitutive photomorphogenic homolog subunit 7A (*Arabidopsis*) |
| 209053_s_at | Wolf-Hirschhorn syndrome candidate 1 |
| 209054_s_at | Wolf-Hirschhorn syndrome candidate 1 |
| 209075_s_at | bromodomain containing 4 |
| 209118_s_at | platelet-activating factor acetylhydrolase, isoform Ib, pseudogene 1 |
| 209120_at | nuclear receptor subfamily 2, group F, member 2 |
| 209122_at | adipose differentiation-related protein |
| 209140_x_at | major histocompatibility complex, class I, B |
| 209153_s_at | transcription factor 3 (E2A immunoglobulin enhancer binding factors E12/E47) |
| 209156_s_at | collagen, type VI, alpha 2 |
| 209173_at | anterior gradient 2 homolog (*Xenepus laevis*) |
| 209215_at | glycoprotein A33 (transmembrane) |
| 209228_x_at | zinc finger protein 212 |
| 209236_at | solute carrier family 23 (nucleobase transporters), member 1 |
| 209262_s_at | nuclear receptor subfamily 2, group F, member 6 |
| 209263_x_at | transmembrane 4 superfamily member 7 |
| 209265_s_at | thioredoxin interacting protein |
| 209289_at | nuclear factor I/B |
| 209290_s_at | nuclear factor I/B |
| 209332_s_at | MAX protein |

TABLE 2-continued genes up-regulated at day 5

| Gene Name | Gene Description |
|---|---|
| 209337_at | gb: AF063020.1 /DEF = *Homo sapiens* lens epithelium-derived growth factor mRNA, complete cds. /FEA = mRNA /PROD = lens epithelium-derived growth factor /DB_XREF = gi: 3283351 /UG = Hs.82110 PC4 and SFRS1 int . . . |
| 209341_s_at | inhibitor of kappa light polypeptide gene enhancer in B-cells, kinase beta |
| 209407_s_at | deformed epidermal autoregulatory factor 1 (*Drosophila*) |
| 209409_at | growth factor receptor-bound protein 10 |
| 209449_at | chromosome 6 open reading frame 28 |
| 209496_at | retinoic acid receptor responder (tazarotene induced) 2 |
| 209505_at | nuclear receptor subfamily 2, group F, member 1 |
| 209581_at | HRAS-like suppressor 3 |
| 209607_x_at | sulfotransferase family, cytosolic, 1A, phenol-preferring, member 3 |
| 209623_at | methylcrotonoyl-Coenzyme A carboxylase 2 (beta) [BLAST] |
| 209630_s_at | G protein-coupled receptor 37 (endothelin receptor type B-like) |
| 209723_at | serine (or cysteine) proteinase inhibitor, clade B (ovalbumin), member 9 |
| 209729_at | growth arrest-specific 2 like 1 |
| 209759_s_at | DEAD/H (Asp-Glu-Ala-Asp/His) box polypeptide 37 |
| 209784_s_at | jagged 2 |
| 209873_s_at | plakophilin 3 |
| 209899_s_at | DnaJ (Hsp40) homolog, subfamily C, member 8 [BLAST] |
| 210010_s_at | solute carrier family 25 (mitochondrial carrier; citrate transporter), member 1 |
| 210026_s_at | succinate dehydrogenase complex, subunit D, integral membrane protein pseudogene 1 |
| 210028_s_at | origin recognition complex, subunit 3-like (yeast) |
| 210069_at | carnitine palmitoyltransferase I, muscle |
| 210095_s_at | insulin-like growth factor binding protein 3 |
| 210105_s_at | FYN oncogene related to SRC, FGR, YES |
| 210111_s_at | G protein-coupled receptor 61 |
| 210150_s_at | laminin, alpha 5 |
| 210208_x_at | HLA-B associated transcript 3 |
| 210336_x_at | zinc finger protein 42 (myeloid-specific retinoic acid-responsive) |
| 210337_s_at | ATP citrate lyase |
| 210371_s_at | retinoblastoma binding protein 4 |
| 210410_s_at | mutS homolog 5 (*E. coli*) |
| 210448_s_at | purinergic receptor P2X, ligand-gated ion channel, 5 |
| 210802_s_at | serine protease inhibitor, Kazal type 4 |
| 210878_s_at | chromosome 5 open reading frame 7 |
| 210891_s_at | general transcription factor II, i |
| 211052_s_at | tubulin-specific chaperone d [BLAST] |
| 211060_x_at | GPAA1P anchor attachment protein 1 homolog (yeast) [BLAST] |
| 211065_x_at | phosphofructokinase, liver [BLAST] |
| 211075_s_at | gb: Z25521.1 /DEF = *H. sapiens integrin associated protein* mRNA, complete CDS,. /FEA = mRNA /PROD = integrin associated protein /DB_XREF = gi: 396704 /FL = gb: Z25521.1 |
| 211270_x_at | polypyrimidine tract binding protein 1 |
| 211284_s_at | granulin |
| 211300_s_at | tumor protein p53 (Li-Fraumeni syndrome) |
| 211358_s_at | neuronal guanine nucleotide exchange factor |
| 211375_s_at | interleukin enhancer binding factor 3, 90 kD |
| 211385_x_at | sulfotransferase family, cytosolic, 1A, phenol-preferring, member 2 |
| 211529_x_at | HLA-G histocompatibility antigen, class I, G |
| 211564_s_at | KH-type splicing regulatory protein (FUSE binding protein 2) |
| 211596_s_at | 1(3)mbt-like (*Drosophila*) [BLAST] |
| 211618_s_at | gb: M31008.1 /DEF = Human intestinal alkaline phosphatase mRNA, complete cds. /FEA = mRNA /GEN = ALPI /DB_XREF = gi: 178443 /FL = gb: M31008.1 |
| 211678_s_at | maternally expressed 3 [BLAST] |
| 211911_x_at | major histocompatibility complex, class I, B [BLAST] |
| 211929_at | heterogeneous nuclear ribonucleoprotein A3 |
| 211967_at | F-box only protein 32 [BLAST] |
| 211969_at | heat shock 90 kD protein 1, alpha |
| 211986_at | AHNAK nucleoprotein (desmoyokin) |
| 212015_x_at | polypyrimidine tract binding protein 1 [BLAST] |
| 212028_at | proline dehydrogenase (oxidase) 2 |
| 212030_at | proline dehydrogenase (oxidase) 2 |
| 212032_s_at | prostate tumor over expressed gene 1 [BLAST] |

TABLE 2-continued genes up-regulated at day 5

| Gene Name | Gene Description |
|---|---|
| 212033_at | proline dehydrogenase (oxidase) 2 |
| 212037_at | pinin, desmosome associated protein |
| 212056_at | MDN1, midasin homolog (yeast) |
| 212062_at | ATPase, Class II, type 9A |
| 212067_s_at | Consensus includes gb: AL573058 /FEA = EST /DB_XREF = gi: 12931931 /DB_XREF = est: AL573058 /CLONE = CS0DI014YC05 (3 prime) /UG = Hs.1279 complement component 1, r subcomponent |
| 212068_s_at | ATPase, Class V, type 10B |
| 212069_s_at | ATPase, Class V, type 10B |
| 212124_at | retinoic acid induced 17 |
| 212137_at | ATP synthase mitochondrial F1 complex assembly factor 2 |
| 212139_at | GCN1 general control of amino-acid synthesis 1-like 1 (yeast) |
| 212143_s_at | insulin-like growth factor binding protein 3 |
| 212159_x_at | adaptor-related protein complex 2, alpha 2 subunit |
| 212170_at | RNA binding motif protein 12 |
| 212186_at | acetyl-Coenzyme A carboxylase alpha |
| 212203_x_at | interferon induced transmembrane protein 3 (1-8U) |
| 212218_s_at | F-box only protein 9 [BLAST] |
| 212231_at | F-box only protein 21 |
| 212251_at | nuclear autoantigenic sperm protein (histone-binding) [BLAST] |
| 212269_s_at | MCM3 minichromosome maintenance deficient 3 (*S. cerevisiae*) associated protein |
| 212285_s_at | agrin |
| 212300_at | Consensus includes gb: AL049795 /DEF = Human DNA sequence from clone RP4-622L5 on chromosome 1p34.2-36.11. Contains the gene for importin alpha 7 (karyopherin), up to six novel genes and the 5 end o . . . |
| 212307_s_at | O-linked N-acetylglucosamine (GlcNAc) transferase (UDP-N-acetylglucosamine:polypeptide-N-acetylglucosaminyl transferase) |
| 212316_at | Rho-related BTB domain containing 2 |
| 212319_at | synaptosomal-associated protein, 91 kD homolog (mouse) |
| 212361_s_at | ATPase, Ca++ transporting, cardiac muscle, slow twitch 2 [BLAST] |
| 212396_s_at | golgi associated, gamma adaptin ear containing, ARF binding protein 2 |
| 212403_at | solute carrier family 25 (mitochondrial oxodicarboxylate carrier), member 21 [BLAST] |
| 212414_s_at | capicua homolog (*Drosophila*) |
| 212429_s_at | general transcription factor IIIC, polypeptide 2 (beta subunit, 110 kD) |
| 212456_at | chromosome 21 open reading frame 80 |
| 212493_s_at | chromosome 20 open reading frame 30 |
| 212498_at | brain-specific angiogenesis inhibitor 3 [BLAST] |
| 212499_s_at | collagen, type II, alpha I (primary osteoarthritis, spondyloepiphyseal dysplasia, congenital) [BLAST] |
| 212520_s_at | SWI/SNF related, matrix associated, actin dependent regulator of chromatin, subfamily a, member 4 |
| 212547_at | Consensus includes gb: N34842 /FEA = EST /DB_XREF = gi: 1155984 /DB_XREF = est: yy45d11.s1 /CLONE = IMAGE: 276501 /UG = Hs.6580 *Homo sapiens* cDNA: FLJ23227 fis, clone CAE00645, highly similar to AF052138 *Homo* . . . |
| 212561_at | ATPase, Class VI, type 11A |
| 212563_at | block of proliferation 1 |
| 212566_at | ret finger protein 2 |
| 212589_at | related RAS viral (r-ras) oncogene homolog 2 - |
| 212612_at | REST corepressor |
| 212630_at | chromobox homolog 3 (HP1 gamma homolog, *Drosophila*) |
| 212644_s_at | collagen, type II, alpha 1 (primary osteoarthritis, spondyloepiphyseal dysplasia, congenital) [BLAST] |
| 212647_at | related RAS viral (r-ras) oncogene homolog |
| 212691_at | SH3-domain GRB2-like endophilin B2 [BLAST] |
| 212693_at | MDN1, midasin homolog (yeast) |
| 212747_at | chromosome 17 open reading frame 31 [BLAST] |
| 212752_at | cytoplasmic linker associated protein 1 |
| 212761_at | transcription factor 7-like 2 (T-cell specific, HMG-box) [BLAST] |
| 212762_s_at | transcription factor 7-like 2 (T-cell specific, HMG-box) [BLAST] |
| 212770_at | pleckatrin homology domain-containing, family A (phosphoinositide binding specific) member 4 |
| 212774_at | zinc finger protein 238 |
| 212825_at | PAX transcription activation domain interacting protein 1 like |

TABLE 2-continued genes up-regulated at day 5

| Gene Name | Gene Description |
|---|---|
| 212887_at | Sec23 homolog A (*S. cerevisiae*) |
| 212890_at | integrin, beta 1 (fibronectin receptor, beta polypeptide, antigen CD29 includes MDF2, MSK12) |
| 212900_at | SEC24 related gene family, member A (*S. cerevisiae*) |
| 212919_at | FGD1 family, member 3 [BLAST] |
| 212929_s_at | fatty-acid-Coenzyme A ligase, long-chain 6 |
| 212936_at | neurocalcin delta [BLAST] |
| 212955_s_at | polymerase (RNA) II (DNA directed) polypeptide I (14.5 kD) |
| 212973_at | Consensus includes gb: AI692341 /FEA = EST /DB_XREF = gi: 4969681 /DB_XREF = est: wd85g04.x1 /CLONE = IMAGE: 2338422 /UG = Hs.79886 ribose 5-phosphate isomerase A (ribose 5-phosphate epimerase) |
| 212993_at | G protein-coupled receptor kinase 7 |
| 213026_at | APG12 autophagy 12-like (*S. cerevisiae*) |
| 213029_at | son of sevenless homolog 1 (*Drosophila*) [BLAST] |
| 213032_at | son of sevenless homolog 1 (*Drosophila*) [BLAST] |
| 213041_s_at | ATP synthase, H+ transporting, mitochondrial F1 complex, delta subunit |
| 213050_at | activity-regulated cytoskeleton-associated protein |
| 213051_at | low voltage-activated T-type calcium channel alpha-1 subunit (CACNA1I) |
| 213057_at | ATP synthase mitochondrial F1 complex assembly factor 2 [BLAST] |
| 213089_at | Consensus includes gb: AU158490 /FEA = EST /DB_XREF = gi: 11020011 /DB_XREF = est: AU158490 /CLONE = PLACE3000042 /UG = Hs.303632 Human DNA sequence from clone RP11-110H4 on chromosome 5 Contains a pseudogene . . . |
| 213145_at | nucleoporin 133 kD [BLAST] |
| 213182_x_at | Consensus includes gb: R78668 /FEA = EST /DB_XREF = gi: 854949 /DB_XREF = est: yi74c04.r1 /CLONE = IMAGE: 144966 /UG = Hs.106070 cyclin-dependent kinase inhibitor 1C (p57, Kip2) |
| 213212_x_at | F-box only protein 21 |
| 213263_s_at | mitogen-activated protein kinase kinase kinase 12 |
| 213294_at | aldo-keto reductase family 1, member C1 (dihydrodiol dehydrogenase 1; 20-alpha (3-alpha)-hydroxysteroid dehydrogenase) |
| 213313_at | nucleoporin 62 kD |
| 213318_s_at | HLA-B associated transcript 3 |
| 213338_at | zinc finger protein 363 |
| 213360_s_at | chromosome 21 open reading frame 108 |
| 213378_s_at | DEAD/H (Asp-Glu-Ala-Asp/His) box polypeptide 11 (CHL1-like helicase homolog, *S. cerevisiae*) - |
| 213390_at | chromosome 19 open reading frame 7 |
| 213398_s_at | mitochondrial ribosomal protein S22 |
| 213400_s_at | transducin (beta)-like 1X-linked [BLAST] |
| 213428_s_at | collagen, type VI, alpha 1 |
| 213505_s_at | C-type (calcium dependent, carbohydrate-recognition domain) lectin, superfamily member 1 (cartilage-derived) |
| 213518_at | RNA binding motif protein 15 |
| 213581_at | chromosome 21 open reading frame 67 |
| 213645_at | Consensus includes gb: AF305057 /DEF = *Homo sapiens* RTS (RTS) gene, complete cds, alternatively spliced /FEA = mRNA_1 /DB_XREF = gi: 11094017 /UG = Hs.180433 rTS beta protein |
| 213668_s_at | Consensus includes gb: AI989477 /FEA = EST /DB_XREF = gi: 5836358 /DB_XREF = est: ws25b11.x1 /CLONE = IMAGE: 2498205 /UG = Hs.83484 SRY (sex determining region Y)-box 4 |
| 213670_x_at | chromosome 21 open reading frame 108 |
| 213682_at | Consensus includes gb: AL036344 /FEA = EST /DB_XREF = gi: 5927743 /DB_XREF = est: DKFZp564A053_r1 /CLONE = DKFZp564A053 /UG = Hs.169329 DKFZP564A043 protein |
| 213704_at | Rab geranylgeranyltransferase, beta subunit |
| 213720_s_at | SWI/SNF related, matrix associated, actin dependent regulator of chromatin, subfamily a, member 4 [BLAST] |
| 213746_s_at | filamin A, alpha (actin binding protein 280) [BLAST] |
| 213773_x_at | LUC7-like (*S. cerevisiae*) |
| 213838_at | RAN binding protein 9 |
| 213842_x_at | Williams Beuren syndrome chromosome region 22 |
| 213887_s_at | polymerase (RNA) II (DNA directed) polypeptide E (25 kD) [BLAST] |
| 213892_s_at | adenine phosphoribosyltransferase |
| 213923_at | RAP2B, member of RAS oncogene family |
| 213947_s_at | Rho-related BTB domain containing 2 [BLAST] |
| 213977_s_at | neuronal guanine nucleotide exchange factor |
| 213998_s_at | DEAD/H (Asp-Glu-Ala-Asp/His) box polypeptide 17 (72 kD) |
| 214022_s_at | interferon induced transmembrane protein 1 (9-27) |
| 214035_x_at | nuclear pore complex interacting protein |

TABLE 2-continued genes up-regulated at day 5

| Gene Name | Gene Description |
|---|---|
| 214093_s_at | RNA polymerase I associated factor, 53 kD |
| 214097_at | ribosomal protein S21 |
| 214100_x_at | LUC7-like (*S. cerevisiae*) |
| 214113_s_at | RNA binding motif protein 8A |
| 214149_s_at | Consensus includes gb: AI252582 /FEA = EST /DB_XREF = gi: 3849111 /DB_XREF = est: qv25b02.x1 /CLONE = IMAGE: 1982571 /UG = Hs.24322 ATPase, H+ transporting, lysosomal (vacuolar proton pump) 9 kD |
| 214246_x_at | cholinergic receptor, nicotinic, epsilon polypeptide |
| 214259_s_at | aldo-keto reductase family 7, member A2 (aflatoxin aldehyde reductase) |
| 214356_s_at | pumilio homolog 2 (*Drosophila*) |
| 214484_s_at | protease, serine, 16 (thymus) |
| 214500_at | H2A histone family, member Y |
| 214531_s_at | sorting nexin 1 |
| 214581_x_at | tumor necrosis factor receptor superfamily, member 21 |
| 214657_s_at | Consensus includes gb: AU134977 /FEA = EST /DB_XREF = gi: 10995516 /DB_XREF = est: AU134977 /CLONE = PLACE1000926 /UG = Hs.322149 Human clone 137308 mRNA, partial cds |
| 214679_x_at | Consensus includes gb: AL110227.1 /DEF = *Homo sapiens* mRNA; cDNA DKFZp434J194 (from clone DKFZp434J194). /FEA = mRNA /DB_XREF = gi: 5817165 /UG = Hs.323067 *Homo sapiens* mRNA; cDNA DKFZp434J194 (from clone . . . |
| 214753_at | Consensus includes gb: AW084068 /FEA = EST /DB_XREF = gi: 6039220 /DB_XREF = est: xc26c06.x1 /CLONE = IMAGE: 2585386 /UG = Hs.110630 Human BRCA2 region, mRNA sequence CG006 |
| 214911_s_at | Consensus includes gb: S78771.1 /DEF = NAT = CpG island-associated gene human, mRNA, 1741 nt. /FEA = mRNA /DB_XREF = gi: 244232 /UG = Hs.75243 bromodomain-containing 2 |
| 214919_s_at | baculoviral IAP repeat-containing 6 (apollon) |
| 215001_s_at | glutamate-ammonia ligase (glutamine synthase) |
| 215089_s_at | Protein tyrosine phosphatase, receptor type, epsilon polypeptide |
| 215210_s_at | dihydrolipoamide S-succinyltransferase (E2 component of 2-oxo-glutarate complex) |
| 215245_x_at | fragile X mental retardation 1 [BLAST] |
| 215313_x_at | major histocompatibility complex, class I, A |
| 215464_s_at | phosphoinositide-3-kinase, regulatory subunit 4, p150 |
| 215482_s_at | PRP31 pre-mRNA processing factor 31 homolog (yeast) |
| 215498_s_at | mitogen-activated protein kinase kinase 3 |
| 215690_x_at | GPAA1P anchor attachment protein 1 homolog (yeast) |
| 215696_s_at | aryl-hydrocarbon receptor nuclear translocator 2 |
| 215731_s_at | M-phase phosphoprotein 9 |
| 215807_s_at | plexin B1 |
| 215823_x_at | Consensus includes gb: U64661 /DEF = Human poly(A)-binding protein processed pseudogene3 /FEA = mRNA /DB_XREF = gi: 1519214 /UG = Hs.283767 poly(A)-binding protein, cytoplasmic, pseudogene 3 |
| 215884_s_at | ubiquilin 2 |
| 216033_s_at | chromosome 20 open reading frame 100 |
| 216237_s_at | MCM5 minichromosome maintenance deficient 5, cell division cycle 46 (*S. cerevisiae*) [BLAST] |
| 216264_s_at | laminin, beta 2 (laminin S) |
| 216384_x_at | Consensus includes gb: AF257099 /DEF = *Homo sapiens* prothymosin alpha (PTMA) gene, complete cds /FEA = CDS /DB_XREF = gi: 8037944 /UG = Hs.283947 *Homo sapiens* prothymosin alpha (PTMA) gene, complete cds |
| 216457_s_at | pecanex-like 3 (*Drosophila*) |
| 216565_x_at | Consensus includes gb: AL121994 /DEF = Human DNA sequence from clone RP4-781L3 on chromosome 1p34.3-36.11 Contains a pseudogene similar to IFITM3 (interferon inducedntransmembrane protein 3 (1-8U)), . . . |
| 216620_s_at | Rho guanine nucleotide exchange factor (GEF) 10 |
| 216894_x_at | Consensus includes gb: D64137 /DEF = Human KIP2 gene for Cdk-inhibitor p57KIP2, complete cds (exon1-4) /FEA = mRNA_4 /DB_XREF = gi: 992945 /UG = Hs.106070 cyclin-dependent kinase inhibitor 1C (p57, Kip2) |
| 216913_s_at | Rho-related BTB domain containing 2 [BLAST] |
| 216952_s_at | lamin B2 |
| 217221_x_at | RNA binding motif protein 10 |
| 217301_x_at | retinoblastoma binding protein 4 |
| 217419_x_at | Consensus includes gb: AK021586.1 /DEF = *Homo sapiens* cDNA FLJ11524 fis, clone HEMBA1002547, highly similar to *Homo sapiens* agrin precursor mRNA. /FEA = mRNA /DB_XREF = gi: 10432794 /UG = Hs.273330 *Homo s* . . . |
| 217718_s_at | mitochondrial ribosomal protein L42 |

TABLE 2-continued genes up-regulated at day 5

| Gene Name | Gene Description |
|---|---|
| 217749_at | ring finger protein 12 |
| 217751_at | spastic paraplegia 3A (autosomal dominant) |
| 217755_at | hematological and neurological expressed 1 |
| 217759_at | sperm associated antigen 10 |
| 217767_at | complement component 3 |
| 217770_at | tripartite motif-containing 33 |
| 217779_s_at | zinc finger, DHHC domain containing 7 |
| 217794_at | TAF7-like RNA polymerase II, TATA box binding protein (TBP)-associated factor, 50 kD |
| 217807_s_at | glioma tumor suppressor candidate region gene 2 |
| 217809_at | G protein-coupled receptor kinase-interactor 1 |
| 217836_s_at | chromosome 20 open reading frame 44 |
| 217906_at | cyclin D-type binding-protein 1 |
| 217914_at | nucleoporin 54 kD |
| 217918_at | ORM1-like 2 (S. cerevisiae) |
| 217957_at | ORM1-like 2 (S. cerevisiae) |
| 217969_at | chromosome 11 open reading frame2 |
| 217973_at | hydroxyacid oxidase 2 (long chain) |
| 217983_s_at | RTC domain containing 1 |
| 217984_at | RTC domain containing 1 |
| 218001_at | mitochondrial ribosomal protein S2 [BLAST] |
| 218010_x_at | chromosome 20 open reading frame 149 |
| 218035_s_at | chromosome 20 open reading frame 16 |
| 218059_at | ribosomal protein L26-like 1 |
| 218076_s_at | solute carrier family 38, member 4 |
| 218083_at | prostaglandin E synthase 2 |
| 218090_s_at | gb: NM_018117.8 /DEF = Homo sapiens WD40 repeat domain 11 protein (WDR11), mRNA. /FEA = mRNA /GEN = WDR11 /PROD = WD40 repeat domain 11 protein /DB_XREF = gi: 13324687 /UG = Hs.16677 WD repeat domain 15 /FL = gb . . . |
| 218096_at | chromosome 20 open reading frame 46 |
| 218112_at | mitochondrial ribosomal protein S34 |
| 218123_at | chromosome 21 open reading frame 59 |
| 218134_s_at | LUC7-like (S. cerevisiae) |
| 218145_at | chromosome 20 open reading frame 97 |
| 218180_s_at | RNA binding motif protein 15 |
| 218205_s_at | eukaryotic translation initiation factor 2 alpha kinase 4 |
| 218220_at | chromosome 12 open reading frame 10 |
| 218228_s_at | tankyrase, TRF1-interacting ankyrin-related ADP-ribose polymerase 2 |
| 218241_at | golgi autoantigen, golgin subfamily a, 5 |
| 218244_at | FK506 binding protein 14 (22 kDa) |
| 218263_s_at | ras homolog gene family, member U |
| 218294_s_at | PRP31 pre-mRNA processing factor 31 homolog (yeast) |
| 218315_s_at | chromosome 20 open reading frame 34 |
| 218317_x_at | ganglioside-induced differentiation-associated protein 1-like 1 |
| 218323_at | chromosome 15 open reading frame 12 |
| 218328_at | mitochondrial ribosomal protein S2 |
| 218366_x_at | WD repeat domain 13 |
| 218379_at | RNA binding motif protein 7 |
| 218388_at | 6-phosphogluconolactonase |
| 218391_at | dual specificity phosphatase 12 |
| 218415_at | vacuolar protein sorting 33B (yeast) |
| 218437_s_at | leucine zipper transcription factor-like 1 |
| 218443_s_at | DAZ associated protein 1 |
| 218448_at | chromosome 20 open reading frame 11 |
| 218450_at | heme binding protein 1 |
| 218494_s_at | SLC2A4 regulator |
| 218529_at | toll-like receptor 7 |
| 218592_s_at | cat eye syndrome chromosome region, candidate 5 [BLAST] |
| 218652_s_at | protein phosphatase 1, regulatory (inhibitor) subunit 14D |
| 218659_at | chromosome 20 open reading frame 36 |
| 218697_at | G-2 and S-phase expressed 1 |
| 218744_s_at | protein kinase C and casein kinase substrate in neurons 3 |
| 218755_at | RAB6 interacting, kinesin-like (rabkinesin6) |
| 218756_s_at | matrix metalloproteinase 28 |
| 218767_at | chromosome 12 open reading frame 5 |
| 218773_s_at | kinesin-associated protein 3 |
| 218796_at | chromosome 20 open reading frame 42 |
| 218821_at | aminopeptidase-like 1 |
| 218839_at | hairy/enhancer-of-split related with YRPW motif 1 |
| 218848_at | MEF2-interacting transcription repressor |
| 218856_at | mitochondrial ribosomal protein L35 |
| 218860_at | hypothetical protein, clone MTA.D02.090 |

TABLE 2-continued genes up-regulated at day 5

| Gene Name | Gene Description |
| --- | --- |
| 218865_at | ATP synthase mitochondrial F1 complex assembly factor 1 |
| 218872_at | chromosome 20 open reading frame 11 |
| 218908_at | alveolar soft part sarcoma chromosome region, candidate 1 |
| 218921_at | testicular cell adhesion molecule 1 |
| 218983_at | immediate early response 5 |
| 218986_s_at | aldehyde reductase (aldose reductase) like 6 |
| 219007_at | hypothetical protein FLJ13287 |
| 219041_s_at | pre-B lymphocyte gene 3 |
| 219053_s_at | epsin 3 |
| 219066_at | mitochondrial ribosomal protein S35 |
| 219117_s_at | FK506 binding protein 11 (19 kDa) |
| 219151_s_at | general transcription factor IIE, polypeptide 1 (alpha subunit, 56 kD) |
| 219165_at | arachidonate lipoxygenase 3 |
| 219166_at | mitochondrial ribosomal protein S18A |
| 219188_s_at | chromosome 20 open reading frame 40 |
| 219192_at | vacuolar protein sorting 11 (yeast) |
| 219203_at | chromosome 20 open reading frame 45 |
| 219357_at | mitochondrial ribosomal protein S28 |
| 219534_x_at | cyclin-dependent kinase inhibitor 1C (p57, Kip2) |
| 219571_s_at | G protein-coupled receptor, family C, group 1, member B |
| 219763_at | zinc finger protein 317 |
| 219764_at | frizzled homolog 10 (Drosophila) |
| 219816_s_at | zinc finger, DHHC domain containing 4 |
| 219880_at | conserved intergenic sequence 2 |
| 219911_s_at | solute carrier family 21 (organic anion transporter), member 12 |
| 219914_at | endothelin converting enzyme-like 1 |
| 220079_s_at | pecanex-like 3 (Drosophila) |
| 220212_s_at | neuromedin U |
| 220597_s_at | bridging integrator 3 |
| 220690_s_at | EGF-like-domain, multiple 6 |
| 220748_s_at | serine (or cysteine) proteinase inhibitor, clade A (alpha-1 antiproteinase, antitrypsin), member 10 |
| 220925_at | transgene insertion A2, Pierre Coulombe |
| 221050_s_at | GTP binding protein 2 |
| 221203_s_at | hypoxia-inducible factor 1, alpha subunit inhibitor |
| 221264_s_at | Alpha1, 2-fucosyltransferase a [BLAST] |
| 221269_s_at | SH3 domain binding glutamic acid-rich protein like 3 [BLAST] |
| 221501_x_at | nuclear pore complex interacting protein |
| 221509_at | density-regulated protein |
| 221562_s_at | sirtuin silent mating type information regulation 2 homolog 3 (S. cerevisiae) |
| 221647_s_at | DEAD/H (Asp-Glu-Ala-Asp/His) box polypeptide 35 |
| 221689_s_at | Down syndrome critical region gene 5 |
| 221699_s_at | ganglioside-induced differentiation-associated protein 1-like 1 [BLAST] |
| 221712_s_at | protocadherin beta 17 pseudogene [BLAST] |
| 221725_at | WAS protein family, member 2 |
| 221750_at | Consensus includes gb: BG035985 /FEA = EST /DB_XREF = gi: 12430666 /DB_XREF = est: 602326096F1 /CLONE = IMAGE: 4414319 /UG = Hs.77910 3-hydroxy-3-methylglutaryl-Coenzyme A synthase 1 (soluble) |
| 221766_s_at | Consensus includes gb: AW246673 /FEA = EST /DB_XREF = gi: 6589666 /DB_XREF = est: 2821951.3prime /CLONE = IMAGE: 2821951 /UG = Hs.10784 hypothetical protein FLJ20037 |
| 221786_at | Consensus includes gb: BF197222 /FEA = EST /DB_XREF = gi: 11085906 /DB_XREF = est: 7m88b07.x1 /CLONE = IMAGE: 3561949 /UG = Hs.12342 Homo sapiens clone 24538 mRNA sequence |
| 221789_x_at | solute carrier family 25 (mitochondrial oxodicarboxylate carrier), member 21 |
| 221816_s_at | ankyrin repeat and SOCS box-containing 3 [BLAST] |
| 221827_at | chromosome 20 open reading frame 18 |
| 221918_at | PCTAIRE protein kinase 2 |
| 221919_at | heterogeneous nuclear ribonucleoprotein A1 |
| 221931_s_at | chromosome 20 open reading frame 150 |
| 221932_s_at | insulin-like growth factor 2, antisense |
| 221989_at | ribosomal protein L10 |
| 222010_at | acetyl-Coenzyme A acetyltransferase 2 (acetoacetyl Coenzyme A thiolase) |
| 222011_s_at | acetyl-Coenzyme A acetyltransferase 2 (acetoacetyl Coenzyme A thiolase) |
| 222037_at | MCM4 minichromosome maintenance deficient 4 (S. cerevisiae) |
| 222040_at | heterogeneous nuclear ribonucleoprotein A1 |

TABLE 2-continued genes up-regulated at day 5

| Gene Name | Gene Description |
| --- | --- |
| 222122_s_at | retinoic acid induced 17 [BLAST] |
| 222131_x_at | solute carrier family 25 (mitochondrial oxodicarboxylate carrier), member 21 |
| 222154_s_at | golgi reassembly stacking protein 2, 55 kDa |
| 222155_s_at | chromosome 1 open reading frame 28 |
| 222206_s_at | p21(CDKN1A)-activated kinase 6 |
| 222369_at | ribosomal protein L36a |

TABLE 3 genes down-regulated at day 2

| Gene Name | Gene Description |
| --- | --- |
| 1316_at | thyroid hormone receptor, alpha (erythroblastic leukemia viral (v-erb-a) oncogene homolog, avian) |
| 35150_at | tumor necrosis factor receptor superfamily, member 5 |
| 36829_at | period homolog 1 (*Drosophila*) |
| 37793_r_at | RAD51-like 3 (*S. cerevisiae*) |
| 47571_at | zinc finger protein 236 |
| 49327_at | sirtuin silent mating type information regulation 2 homolog 3 (*S. cerevisiae*) |
| 48612_at | tubulin, beta polypeptide 4, member Q |
| 58900_at | Kruppel-like factor 13 |
| 200706_s_at | fragile X mental retardation, autosomal homolog 2 |
| 200915_x_at | kinectin 1 (kinesin receptor) |
| 200976_s_at | Tax1 (human T-cell leukemia virus type I) binding protein 1 |
| 201057_s_at | golgi autoantigen, golgin subfamily b, macrogolgin (with transmembrane signal), 1 |
| 201070_x_at | splicing factor 3b, subunit 1, 155 kD |
| 201140_s_at | RAB5C, member RAS oncogene family |
| 201278_at | disabled homolog 2, mitogen-responsive phosphoprotein (*Drosophila*) |
| 201386_s_at | DEAD/H (Asp-Glu-Ala-Asp/His) box polypeptide 15 |
| 201567_s_at | golgi autoantigen, golgin subfamily a, 4 |
| 201686_x_at | apoptosis inhibitor 5 |
| 201878_at | ariadne homolog, ubiquitin-conjugating enzyme E2 binding protein, 1 (*Drosophila*) |
| 201884_at | carcinoembryonic antigen-related cell adhesion molecule 5 |
| 201971_s_at | ATPase, H+ transporting, lysosomal 70 kD, V1 subunit A, isoform 1 |
| 202037_s_at | secreted frizzled-related protein 1 |
| 202071_at | syndecan 4 (amphiglycan, ryudocan) |
| 202122_s_at | glycoprotein A33 (transmembrane) |
| 202224_at | Consensus includes gb: BF304695 /FEA = EST /DB_XREF = gi: 11251580 /DB_XREF = est: 601888248F1 /CLONE = IMAGE: 4122466 /UG = Hs.306088 v-crk avian sarcoma virus CT10 oncogene homolog /FL = gb: D10656.1 gb: NM_016823.1 |
| 202340_x_at | nuclear receptor subfamily 4, group A, member 1 |
| 202488_s_at | FXYD domain-containing ion transport regulator 3 |
| 202604_x_at | a disintegrin and metalloproteinase domain 10 |
| 202668_at | ephrin-B2 |
| 202709_at | fibromodulin |
| 202840_at | gb: NM_003487.1 /DEF = *Homo sapiens* TATA box binding protein (TBP)-associated factor, RNA polymerase II, N, 68 kD (RNA-binding protein 56) (TAF2N), mRNA. /FEA = mRNA /GEN = TAF2N /PROD = TATA box binding . . . |
| 202861_at | period homolog 1 (*Drosophila*) |
| 202873_at | ATPase, H+ transporting, lysosomal 42 kD, V1 subunit C, isoform 1 |
| 202902_s_at | cathepsin S |
| 202921_s_at | ankyrin 2, neuronal |
| 203134_at | phosphatidylinositol binding clathrin assembly protein |
| 203243_s_at | transducin (beta)-like 3 |
| 203319_s_at | zinc finger protein 148 (pHZ-52) |
| 203395_s_at | hairy homolog (*Drosophila*) |
| 203511_s_at | potassium large conductance calcium-activated channel, subfamily M beta member 3 |
| 203512_at | potassium large conductance calcium-activated channel, subfamily M beta member 3 |
| 203666_at | stromal cell-derived factor 1 |
| 203758_at | cathepsin O |

TABLE 3-continued genes down-regulated at day 2

| Gene Name | Gene Description |
|---|---|
| 203788_s_at | sema domain, immunoglobulin domain (Ig), short basic domain, secreted, (semaphorin) 3C |
| 203875_at | SWI/SNF related, matrix associated, actin dependent regulator of chromatin, subfamily a, member 1 |
| 203887_s_at | thrombomodulin |
| 203922_s_at | cytochrome b-245, beta polypeptide (chronic granulomatous disease) |
| 203933_at | sema domain, immunoglobulin domain (Ig), short basic domain, secreted, (semaphorin) 3E |
| 203963_at | carbonic anhydrase XII |
| 204042_at | WAS protein family, member 3 |
| 204230_s_at | solute carrier family 17 (sodium-dependent inorganic phosphate cotransporter), member 7 |
| 204232_at | Fc fragment of IgE, high affinity I, receptor for; gamma polypeptide |
| 204243_at | rearranged L-myc fusion sequence |
| 204312_x_at | cAMP responsive element binding protein 1 |
| 204421_s_at | gb: M27968.1 /DEF = Human basic fibroblast growth factor (FGF) mRNA, complete cds. /FEA = mRNA /GEN = FGF2 /DB_XREF = gi: 182562 /UG = Hs.284244 fibroblast growth factor 2 (basic) /FL = gb: M27968.1 gb: NM_002006.1 |
| 204670_x_at | major histocompatibility complex, class II, DR beta 1 |
| 204762_s_at | guanine nucleotide binding protein (G protein), alpha activating activity polypeptide O |
| 204802_at | Ras-related associated with diabetes |
| 204842_x_at | sperm autoantigenic protein 17 |
| 204906_at | ribosomal protein S6 kinase, 90 kD, polypeptide 2 |
| 204923_at | chromosome X open reading frame 9 |
| 205046_at | centromere protein E (312 kD) |
| 205097_at | solute carrier family 26 (sulfate transporter), member 2 |
| 205166_at | calpain 5 |
| 205232_s_at | platelet-activating factor acetylhydrolase 2 (40 kD) |
| 205235_s_at | M-phase phosphoprotein 1 |
| 205312_at | spleen focus forming virus (SFFV) proviral integration oncogene spil |
| 205328_at | claudin 10 |
| 205359_at | A kinase (PRKA) anchor protein 6 |
| 205370_x_at | dihydrolipoamide branched chain transacylase (E2 component of branched chain keto acid dehydrogenase complex; maple syrup urine disease) |
| 205381_at | mesothelin |
| 205431_s_at | bone morphogenetic protein 5 |
| 205520_at | striatin, calmodulin binding protein |
| 205525_at | gb: NM_018495.3 /DEF = Homo sapiens NAG22 protein (LOC55873), mRNA. /FEA = mRNA /GEN = LOC55873 /PROD = NAG22 protein /DB_XREF = gi: 13236500 /UG = Hs.283080 NAG22 protein /FL = gb: AF247820.3 gb: NM_018495.3 |
| 205595_at | desmoglein 3 (pemphigus vulgaris antigen) |
| 205608_s_at | angiopoietin 1 |
| 205636_at | SH3-domain GRB2-like 3 [BLAST] |
| 205729_at | oncostatin M receptor |
| 205752_s_at | glutathione S-transferase M5 |
| 205879_x_at | ret proto-oncogene (multiple endocrine neoplasia and medullary thyroid carcinoma 1, Hirschsprung disease) |
| 205949_at | carbonic anhydrase I |
| 205981_s_at | inhibitor of growth family, member 1-like |
| 206096_at | zinc finger protein 35 (clone HF.10) |
| 206169_x_at | MCF.2 cell line derived transforming sequence-like |
| 206212_at | carboxypeptidase A2 (pancreatic) |
| 206263_at | flavin containing monooxygenase 4 |
| 206291_at | neurotensin |
| 206323_x_at | oligophrenin 1 |
| 206388_at | phosphodiesterase 3A, cGMP-inhibited |
| 206389_s_at | phosphodiesterase 3A, cGMP-inhibited |
| 206456_at | gamma-aminobutyric acid (GABA) A receptor, alpha 5 |
| 206551_x_at | transient receptor potential cation channel, subfamily M, member 4 |
| 206586_at | cannabinoid receptor 2 (macrophage) |
| 206766_at | integrin, alpha 10 |
| 206825_at | oxytocin receptor |
| 206910_x_at | H factor (complement)-like 3 |
| 206936_x_at | chromosome 20 open reading frame 110 |
| 207041_at | mannan-binding lectin serine protease 2 |
| 207064_s_at | amine oxidase, copper containing 2 (retina-specific) |
| 207131_x_at | gamma-glutamyltransferase 1 |

TABLE 3-continued genes down-regulated at day 2

| Gene Name | Gene Description |
|---|---|
| 207152_at | neurotrophic tyrosine kinase, receptor, type 2 |
| 207300_s_at | coagulation factor VII (serum prothrombin conversion accelerator) |
| 207347_at | excision repair cross-complementing rodent repair deficiency, complementation group 6 |
| 207365_x_at | kinetochore associated 1 |
| 207389_at | glycoprotein Ib (platelet), alpha polypeptide |
| 207408_at | organic cationic transporter-like 4 |
| 207608_x_at | cytochrome P450, subfamily I (aromatic compound-inducible), polypeptide 2 |
| 207730_x_at | chromosome 20 open reading frame 11 |
| 207732_s_at | discs, large (Drosophila) homolog 3 (neuroendocrine-dlg) |
| 207734_at | elongation of very long chain fatty acids (FEN1/Elo2, SUR4/Elo3, yeast)-like 2 |
| 207755_at | chromosome 20 open reading frame 48 |
| 207908_at | keratin 2A (epidermal ichthyosis bullosa of Siemens) |
| 207936_x_at | ret finger protein-like 3 |
| 207938_at | protease inhibitor 15 |
| 207953_at | Consensus includes gb: AF010144.1 /DEF = Homo sapiens neuronal thread protein AD7c-NTP mRNA, complete cds. /FEA = mRNA /PROD = neuronal thread protein AD7c-NTP /DB_XREF = gi: 3002526 /UG = Hs.129735 neuronal . . . |
| 207969_x_at | acrosomal vesicle protein 1 [BLAST] |
| 208120_x_at | gb: NM_031221.1 /DEF = Homo sapiens hypothetical protein FKSG63 (FKSG63), mRNA. /FEA = mRNA /GEN = FKSG63 /PROD = hypothetical protein FKSG63 /DB_XREF = gi: 13654297 /FL = gb: NM_031221.1 |
| 208124_s_at | sema domain, immunoglobulin domain (Ig), transmembrane domain (TM) and short cytoplasmic domain, (semaphorin) 4F |
| 208137_x_at | gb: NM_030972.1 /DEF = Homo sapiens hypothetical protein MGC5384 (MGC5384), mRNA. /FEA = mRNA /GEN = MGC5384 /PROD = hypothetical protein MGC5384 /DB_XREF = gi: 13775165 /FL = gb: NM_030972.1 |
| 208138_at | gastrin |
| 208185_x_at | Consensus includes gb: NM_016415.1 /DEF = Homo sapiens clone FLB3816 (LOC51216), mRNA. /FEA = mRNA /GEN = LOC51216 /PROD = clone FLB3816 /DB_XREF = gi: 10047109 /UG = Hs.277887 clone FLB3816 /FL = gb: NM_016415.1 . . . |
| 208238_x_at | protocadherin beta 1 |
| 208246_x_at | protein phosphatase 1, regulatory (inhibitor) subunit 12C |
| 208306_x_at | major histocompatibility complex, class II, DR beta 4 |
| 208351_s_at | mitogen-activated protein kinase 1 |
| 208360_s_at | gb: NM_015870.1 /DEF = Homo sapiens endogenous retrovirus H D1 leader regionintegrase-derived ORF1, ORF2, and putative envelope protein (HSU88895), mRNA. /FEA = mRNA /GEN = HSU88895 /PROD = endogenous re . . . |
| 208382_s_at | DMC1 dosage suppressor of mck1 homolog, meiosis-specific homologous recombination (yeast) |
| 208447_s_at | phosphoribosyl pyrophosphate synthetase 1 |
| 208486_at | cytochrome P450, subfamily IVA, polypeptide 11 [BLAST] |
| 208520_at | olfactory receptor, family 10, subfamily H, member 3 |
| 208730_x_at | RAB2, member RAS oncogene family |
| 208763_s_at | delta sleep inducing peptide, immunoreactor |
| 208860_s_at | alpha thalassemia/mental retardation syndrome X-linked (RAD54 homolog, S. cerevisiae) |
| 208868_s_at | GABA(A) receptor-associated protein like 1 |
| 208869_s_at | GABA(A) receptor-associated protein like 1 |
| 209312_x_at | gb: U65585.1 /DEF = Homo sapiens MHC class II antigen (HLA-DRB1) mRNA, HLA-DRB1*PBL allele, complete cds. /FEA = mRNA /GEN = HLA-DRB1 /PROD = MHC class II antigen /DB_XREF = gi: 5478215 /UG = Hs.180255 major . . . |
| 209436_at | spondin 1, (f-spondin) extracellular matrix protein |
| 209535_s_at | LIM and SH3 protein 1 |
| 209701_at | desmin [BLAST] |
| 209703_x_at | component of oligomeric golgi complex 4 |
| 209790_s_at | caspase 6, apoptosis-related cysteine protease [BLAST] |
| 209875_s_at | secreted phosphoprotein 1 (osteopontin, bone sialoprotein I, early T-lymphocyte activation 1) |
| 209882_at | Ric-like, expressed in many tissues (Drosophila) |
| 209913_x_at | synaptosomal-associated protein, 91 kD homolog (mouse) |
| 210048_at | N-ethylmaleimide-sensitive factor attachment protein, gamma |
| 210226_at | nuclear receptor subfamily 4, group A, member 1 |
| 210412_at | glutamate receptor, ionotropic, N-methyl D-aspartate 2B |

TABLE 3-continued genes down-regulated at day 2

| Gene Name | Gene Description |
|---|---|
| 210686_x_at | gb: BC001407.1 /DEF = *Homo sapiens*, Similar to cytochrome c-like antigen, clone MGC: 2960, mRNA, complete cds. /FEA = mRNA /PROD = Similar to cytochrome c-like antigen /DB_XREF = gi: 12655110 /UG = Hs. 253070 . . . |
| 210739_x_at | solute carrier family 4, sodium bicarbonate cotransporter, member 4 |
| 210757_x_at | disabled homolog 2, mitogen-responsive phosphoprotein (*Drosophila*) |
| 210796_x_at | sialic acid binding Ig-like lectin 6 |
| 210836_x_at | phosphodiesterase 4D, cAMP-specific (phosphodiesterase E3 dunce homolog, *Drosophila*) |
| 210837_s_at | phosphodiesterase 4D, cAMP-specific (phosphodiesterase E3 dunce homolog, *Drosophila*) |
| 210912_x_at | glutathione S-transferase M4 |
| 210923_at | chromosome 20 open reading frame 82 |
| 210944_s_at | calpain 3, (p94) |
| 210962_s_at | A kinase (PRKA) anchor protein (yotiao) 9 |
| 211014_s_at | promyelocytic leukemia |
| 211026_s_at | monoglyceride lipase [BLAST] |
| 211040_x_at | gb: BC006325.1 /DEF = *Homo sapiens*, G-2 and S-phase expressed 1, clone MGC: 12560, mRNA, complete cds. /FEA = mRNA /PROD = G-2 and S-phase expressed 1 /DB_XREF = gi: 13623450 /FL = gb: BC006325.1 |
| 211071_s_at | chromosome 12 open reading frame 8 [BLAST] |
| 211074_at | gb: AF000381.1 /DEF = *Homo sapiens* non-functional folate binding protein mRNA, complete cds. /FEA = mRNA /PROD = non-functional folate binding protein /DB_XREF = gi: 2565195 /FL = gb: AF000381.1 |
| 211096_at | pre-B-cell leukemia transcription factor 2 |
| 211113_s_at | ATP-binding cassette, sub-family G (WHITE), member 1 |
| 211139_s_at | NGFI-A binding protein 1 (EGR1 binding protein 1) |
| 211277_x_at | amyloid beta (A4) precursor protein (protease nexin-II, Alzheimer disease) |
| 211316_x_at | CASP8 and FADD-like apoptosis regulator |
| 211323_s_at | inositol 1,4,5-triphosphate receptor, type 1 |
| 211328_x_at | hemochromatosis |
| 211364_at | methylthioadenosine phosphorylase |
| 211416_x_at | gamma-glutamyltransferase 1 |
| 211452_x_at | leucine rich repeat (in FLII) interacting protein 1 [BLAST] |
| 211460_at | testis-specific transcript, Y-linked 9 |
| 211464_x_at | caspase 6, apoptosis-related cysteine protease |
| 211504_x_at | Rho-associated, coiled-coil containing protein kinase 2 |
| 211574_s_at | membrane cofactor protein (CD46, trophoblast-lymphocyte cross-reactive antigen) |
| 211657_at | carcinoembryonic antigen-related cell adhesion molecule 6 (non-specific cross reacting antigen) [BLAST] |
| 211685_s_at | neurocalcin delta [BLAST] |
| 211693_at | [BLAST] |
| 211713_x_at | histone deacetylase 4 [BLAST] |
| 211768_at | gb: BC006080.1 /DEF = *Homo sapiens*, Williams-Beuren syndrome chromosome region 5, clone MGC: 12566, mRNA, complete cds. /FEA = mRNA /PROD = Williams-Beuren syndrome chromosome region 5 /DB_XREF = gi: 13543 . . . |
| 211769_x_at | tumor differentially expressed 1 [BLAST] |
| 211781_x_at | gb: BC006164.1 /DEF = *Homo sapiens*, clone MGC: 13219, mRNA, complete cds. /FEA = mRNA /PROD = Unknown (protein for MGC: 13219) /DB_XREF = gi: 13544062 /FL = gb: BC006164.1 |
| 211801_x_at | hypoxia-inducible factor 1, alpha subunit inhibitor |
| 211810_s_at | galactosylceramidase (Krabbe disease) |
| 211814_s_at | cyclin E2 |
| 211918_x_at | placenta-specific 3 [BLAST] |
| 212196_at | tumor necrosis factor receptor superfamily, member 19-like [BLAST] |
| 212233_at | chromosome 1 open reading frame 2 |
| 212514_x_at | Consensus includes gb: R60068 /FEA = EST /DB_XREF = gi: 830763 /DB_XREF = est: yh12h07.s1 /CLONE = IMAGE: 43138 /UG = Hs.147916 DEADH (Asp-Glu-Ala-AspHis) box polypeptide 3 |
| 212736_at | Consensus includes gb: BE299456 /FEA = EST /DB_XREF = gi: 9183204 /DB_XREF = est: 600944717T1 /CLONE = IMAGE: 2960548 /UG = Hs.6349 Human Chromosome 16 BAC clone CIT987SK-A-362G6 |
| 212876_at | UDP-Gal: betaGlcNAc beta 1,4-galactosyltransferase, polypeptide 4 |
| 212884_x_at | apolipoprotein E [BLAST] |
| 213109_at | myelin transcription factor 1-like |
| 213193_x_at | T cell receptor beta locus |

TABLE 3-continued genes down-regulated at day 2

| Gene Name | Gene Description |
|---|---|
| 213270_at | membrane protein, palmitoylated 2 (MAGUK p55 subfamily member 2) [BLAST] |
| 213297_at | nucleolar protein family A, member 2 (H/ACA small nucleolar RNPs) |
| 213307_at | Consensus includes gb: AF131790.1 /DEF = *Homo sapiens* clone 24903 mRNA sequence. /FEA = mRNA /DB_XREF = gi: 4406618 /UG = Hs.12696 cortactin SH3 domain-binding protein |
| 213406_at | golgi associated, gamma adaptin ear containing, ARF binding protein 1 |
| 213486_at | retinoic acid induced 17 [BLAST] |
| 213816_s_at | met proto-oncogene (hepatocyte growth factor receptor) |
| 213936_x_at | surfactant, pulmonary-associated protein B |
| 214007_s_at | protein tyrosine kinase 9 [BLAST] |
| 214336_s_at | coatomer protein complex, subunit alpha |
| 214421_x_at | cytochrome P450, subfamily IIC (mephenytoin 4-hydroxylase), polypeptide 9 [BLAST] |
| 214558_at | G protein-coupled receptor 12 |
| 214594_x_at | ATPase, Class I, type 8B, member 1 |
| 214656_x_at | myosin IC |
| 214698_at | Consensus includes gb: AW190873 /FEA = EST /DB_XREF = gi: 6465353 /DB_XREF = est: x166a01.x1 /CLONE = IMAGE: 2679624 /UG = Hs.145078 regulator of differentiation (in *S. pombe*) 1 |
| 214707_x_at | Alstrom syndrome 1 |
| 214715_x_at | Consensus includes gb: AK024789.1 /DEF = *Homo sapiens* cDNA: FLJ21136 fis, clone CAS07469. /FEA = mRNA /DB_XREF = gi: 10437175 /UG = Hs.206882 *Homo sapiens* mRNA for FLJ00032 protein, partial cds |
| 214720_x_at | Consensus includes gb: BF981643 /FEA = EST /DB_XREF = gi: 12384455 /DB_XREF = est: 602305961F1 /CLONE = IMAGE: 4397295 /UG = Hs.79844 DKFZP564M1416 protein |
| 214849_at | Consensus includes gb: AW500220 /FEA = EST /DB_XREF = gi: 7112628 /DB_XREF = est: UI-HF-BN0-akd-c-02-0-UI.r1 /CLONE = IMAGE: 3076610 /UG = Hs.332496 Human DNA sequence from clone 108K11 on chromosome 6p21 Cont . . . |
| 214902_x_at | Consensus includes gb: AL080232.1 /DEF = *Homo sapiens* mRNA; cDNA DKFZp586A061 (from clone DKFZp586A061). /FEA = mRNA /DB_XREF = gi: 5262725 /UG = Hs.220696 *Homo sapiens* mRNA; cDNA DKFZp586A061 (from clone . . . |
| 214906_x_at | ATPase, H+ transporting, lysosomal 31 kD, V1 subunit E isoform 2 |
| 214923_at | Consensus includes gb: AK001155.1 /DEF = *Homo sapiens* cDNA FLJ10293 fis, clone NT2RM1000280, highly similar to VACUOLAR ATP SYNTHASE SUBUNIT D (EC 3.6.1.34). /FEA = mRNA /DB_XREF = gi: 7022230 /UG = Hs.30 . . . |
| 214933_at | calcium channel, voltage-dependent, P/Q type, alpha 1A subunit |
| 214951_at | UDP-N-acetyl-alpha-D-galactosamine: (N-acetylneuraminyl)-galactosylglucosylceramide N-acetylgalactosaminyltransferase (GalNAc-T) |
| 214953_s_at | amyloid beta (A4) precursor protein (protease nexin-II, Alzheimer disease) |
| 215032_at | nudix (nucleoside diphosphate linked moiety X)-type motif 11 |
| 215067_x_at | chromosome 20 open reading frame 48 |
| 215178_x_at | N-acylsphingosine amidohydrolase (acid ceramidase)-like |
| 215179_x_at | carboxypeptidase N, polypeptide 1, 50 kD |
| 215236_s_at | phosphatidylinositol binding clathrin assembly protein |
| 215366_at | sorting nexin 6 |
| 215373_x_at | chromosome 20 open reading frame 48 |
| 215383_x_at | Consensus includes gb: AL137312.1 /DEF = *Homo sapiens* mRNA; cDNA DKFZp761K23121 (from clone DKFZp761K23121). /FEA = mRNA /DB_XREF = gi: 6807797 /UG = Hs.293681 *Homo sapiens* mRNA; cDNA DKFZp761K23121 (from . . . |
| 215404_x_at | prostate tumor over expressed gene 1 |
| 215439_x_at | F-box and leucine-rich repeat protein 11 |
| 215467_x_at | empty spiracles homolog 1 (*Drosophila*) |
| 215479_at | immunoglobulin superfamily, member 9 [BLAST] |
| 215511_at | Consensus includes gb: U19345.1 /DEF = *Homo sapiens* AR1 (TCF20) mRNA, partial cds. /FEA = mRNA /GEN = TCF20 /PROD = AR1 /DB_XREF = gi: 2924754 /UG = Hs.201668 transcription factor 20 (AR1) |
| 215529_x_at | RecQ protein-like (DNA helicase Q1-like) |
| 215553_x_at | chromosome 6 open reading frame 22 |
| 215587_x_at | chromosome 20 open reading frame 48 |
| 215588_x_at | Consensus includes gb: AK024958.1 /DEF = *Homo sapiens* cDNA: FLJ21305 fis, clone COL02124. /FEA = mRNA /DB_XREF = gi: 10437382 /UG = Hs.287658 *Homo sapiens* cDNA: FLJ21305 fis, clone COL02124 |

TABLE 3-continued genes down-regulated at day 2

| Gene Name | Gene Description |
| --- | --- |
| 215604_x_at | optic atrophy 3 (autosomal recessive, with chorea and spastic paraplegia) |
| 215609_at | Consensus includes gb: AK023895.1 /DEF = Homo sapiens cDNA FLJ13833 fis, clone THYRO1000676. /FEA = mRNA /DB_XREF = gi: 10435969 /UG = Hs.296745 Homo sapiens cDNA FLJ13833 fis, clone THYRO1000676 |
| 215628_x_at | Consensus includes gb: AL049285.1 /DEF = Homo sapiens mRNA; cDNA DKFZp564M193 (from clone DKFZp564M193). /FEA = mRNA /DB_XREF = gi: 4500045 /UG = Hs.302053 Homo sapiens mRNA; cDNA DKFZp564M193 (from clone . . . |
| 215766_at | Consensus includes gb: AL096729.1 /DEF = Homo sapiens mRNA; cDNA DKFZp434D044 (from clone DKFZp434D044). /FEA = mRNA /DB_XREF = gi: 5419863 /UG = Hs.146581 Homo sapiens mRNA; cDNA DKFZp434D044 (from clone . . . |
| 215825_at | Consensus includes gb: AF070579.1 /DEF = Homo sapiens clone 24487 mRNA sequence. /FEA = mRNA /DB_XREF = gi: 3387951 /UG = Hs.283819 Homo sapiens clone 24487 mRNA sequence |
| 215856_at | Consensus includes gb: AK025833.1 /DEF = Homo sapiens cDNA: FLJ22180 fis, clone HRC00936. /FEA = mRNA /DB_XREF = gi: 10438467 /UG = Hs.287692 Homo sapiens cDNA: FLJ22180 fis, clone HRC00936 |
| 215910_s_at | carbohydrate (chondroitin) synthase 1 |
| 215978_x_at | Consensus includes gb: AK021514.1 /DEF = Homo sapiens cDNA FLJ11452 fis, clone HEMBA1001435. /FEA = mRNA /DB_XREF = gi: 10432710 /UG = Hs.148598 Homo sapiens cDNA FLJ11452 fis, clone HEMBA1001435 |
| 216051_x_at | Consensus includes gb: AK022045.1 /DEF = Homo sapiens cDNA FLJ11983 fis, clone HEMBB1001337. /FEA = mRNA /DB_XREF = gi: 10433364 /UG = Hs.193162 Homo sapiens cDNA FLJ11983 fis, clone HEMBB1001337 |
| 216061_x_at | platelet-derived growth factor beta polypeptide (simian sarcoma viral (v-sis) oncogene homolog) |
| 216159_s_at | prostate tumor over expressed gene 1 |
| 216187_x_at | Consensus includes gb: AF222691.1 /DEF = Homo sapiens Alu repeat (LNX1) mRNA sequence. /FEA = mRNA /DB_XREF = gi: 12655850 /UG = Hs.307008 Homo sapiens Alu repeat (LNX1) mRNA sequence |
| 216196_at | chromosome 20 open reading frame 136 [BLAST] |
| 216220_s_at | adenosine A1 receptor |
| 216229_x_at | Consensus includes gb: X81001.1 /DEF = H. sapiens HCG II mRNA. /FEA = mRNA /DB_XREF = gi: 531407 /UG = Hs.69707 HCGII-7 protein |
| 216292_at | Consensus includes gb: AK024455.1 /DEF = Homo sapiens mRNA for FLJ00047 protein, partial cds. /FEA = mRNA /GEN = FLJ00047 /PROD = FLJ00047 protein /DB_XREF = gi: 10440423 /UG = Hs.287753 Homo sapiens mRNA for . . . |
| 216294_s_at | ubiquitin specific protease 24 |
| 216374_at | Consensus includes gb: AC006986 /DEF = Homo sapiens BAC clone RP11-155J5 from Y /FEA = CDS /DB_XREF = gi: 4753246 /UG = Hs.283908 Homo sapiens BAC clone RP11-155J5 from Y |
| 216453_at | chromosome 20 open reading frame 4 [BLAST] |
| 216459_x_at | Consensus includes gb: AL137624.1 /DEF = Homo sapiens mRNA; cDNA DKFZp434M1812 (from clone DKFZp434M1812). /FEA = mRNA /DB_XREF = gi: 6808420 /UG = Hs.306476 Homo sapiens mRNA; cDNA DKFZp434M1812 (from clo . . . |
| 216524_x_at | Consensus includes gb: AL049260.1 /DEF = Homo sapiens mRNA; cDNA DKFZp564E233 (from clone DKFZp564E233). /FEA = mRNA /DB_XREF = gi: 4500007 /UG = Hs.302050 Homo sapiens mRNA; cDNA DKFZp564E233 (from clone . . . |
| 216661_x_at | cytochrome P450, subfamily IIC (mephenytoin 4-hydroxylase), polypeptide 9 |
| 216735_x_at | prostate tumor over expressed gene 1 [BLAST] |
| 216745_x_at | Consensus includes gb: AK024606.1 /DEF = Homo sapiens cDNA: FLJ20953 fis, clone ADSE01979. /FEA = mRNA /DB_XREF = gi: 10436920 /UG = Hs.306697 Homo sapiens cDNA: FLJ20953 fis, clone ADSE01979 |
| 216791_at | lysyl oxidase-like 4 [BLAST] |
| 216859_x_at | Consensus includes gb: AL080112.1 /DEF = Homo sapiens mRNA; cDNA DKFZp586H0722 (from clone DKFZp586H0722). /FEA = mRNA /DB_XREF = gi: 5262539 /UG = Hs.332731 Homo sapiens mRNA; cDNA DKFZp586H0722 (from clo . . . |
| 216873_s_at | ATPase, Class I, type 8B, member 2 |
| 216936_at | Consensus includes gb: X81637.1 /DEF = H. sapiens clathrin light chain b gene. /FEA = mRNA /DB_XREF = gi: 963046 /UG = Hs.73919 clathrin, light polypeptide (Lcb) |
| 216993_s_at | Consensus includes gb: U32169 /DEF = Human pro-a2 chain of collagen type XI (COL11A2) gene, complete cds /FEA = mRNA_3 /DB_XREF = gi: 1000744 /UG = Hs.121509 collagen, type XI, alpha 2 |
| 217020_at | retinoic acid receptor, beta |
| 217052_x_at | Consensus includes gb: AK024108.1 /DEF = Homo sapiens cDNA FLJ14046 fis, clone HEMBA1006461. /FEA = mRNA /DB_XREF = gi: 10436406 /UG = Hs.142677 Homo sapiens cDNA FLJ14046 fis, clone HEMBA1006461 |

TABLE 3-continued genes down-regulated at day 2

| Gene Name | Gene Description |
|---|---|
| 217117_x_at | Consensus includes gb: AF007194.1 /DEF = *Homo sapiens* mucin (MUC3) mRNA, partial cds. /FEA = mRNA /GEN = MUC3 /PROD = mucin /DB_XREF = gi: 2853300 /UG = Hs.129782 mucin 3A, intestinal |
| 217189_s_at | chromosome 1 open reading frame 16 |
| 217269_s_at | protease, serine, 7 (enterokinase) |
| 217315_s_at | kallikrein 13 |
| 217377_x_at | ets variant gene 6 (TEL oncogene) |
| 217446_x_at | Consensus includes gb: AL080160.1 /DEF = *Homo sapiens* mRNA; cDNA DKFZp434M054 (from clone DKFZp434M054). /FEA = mRNA /DB_XREF = gi: 5262622 /UG = Hs.274517 *Homo sapiens* mRNA; cDNA DKFZp434M054 (from clone . . . |
| 217457_s_at | RAP1, GTP-GDP dissociation stimulator 1 |
| 217465_at | NCK-associated protein 1 [BLAST] |
| 217480_x_at | G protein-coupled receptor 2 |
| 217579_x_at | activity-distance traveled 4 |
| 217629_at | chromosome 22 open reading frame 20 |
| 217643_x_at | Consensus includes gb: AA443771 /FEA = EST /DB_XREF = gi: 2156446 /DB_XREF = est: zw95f08.s1 /CLONE = IMAGE: 784743 /UG = Hs.270138 ESTs |
| 217679_x_at | N-acetylglucosamine kinase |
| 217703_x_at | Consensus includes gb: AA401963 /FEA = EST /DB_XREF = gi: 2055965 /DB_XREF = est: zu53c08.s1 /CLONE.IMAGE: 741710 /UG = Hs.194107 ESTs, Moderately similar to ALU7_HUMAN ALU SUBFAMILY SQ SEQUENCE CONTAMINATIO . . . |
| 217713_x_at | chromosome 20 open reading frame 43 |
| 217715_x_at | thymidine kinase 2, mitochondrial |
| 217787_s_at | UDP-N-acetyl-alpha-D-galactosamine: polypeptide N-acetylgalactosaminyltransferase 2 (GalNAc-T2) |
| 217859_s_at | synaptojanin 2 binding protein |
| 217862_at | protein inhibitor of activated STAT, 1 |
| 217878_s_at | Consensus includes gb: AI203880 /FEA = EST /DB_XREF = gi: 3756486 /DB_XREF = est: qf77g07.x1 /CLONE = IMAGE: 1756092 /UG = Hs.172405 cell division cycle 27 /FL = gb: NM_001256.1 |
| 218155_x_at | zinc finger protein 334 |
| 218211_s_at | transgene insertion 202, William Muller |
| 218554_s_at | solute carrier family 22 (organic anion/cation transporter), member 11 |
| 218820_at | LIM homeobox 9 |
| 218949_s_at | chromosome 15 open reading frame 12 |
| 219014_at | toll-like receptor 8 |
| 219183_s_at | pleckstrin homology, Sec7 and coiled/coil domains 4 |
| 219194_at | sema domain, immunoglobulin domain (Ig), transmembrane domain (TM) and short cytoplasmic domain, (semaphorin) 4G |
| 219206_x_at | mitochondrial ribosomal protein L48 |
| 219221_at | engulfment and cell motility 3 (ced-12 homolog, *C. elegans*) |
| 219228_at | chromosome Y open reading frame 14 |
| 219290_x_at | dual adaptor of phosphotyrosine and 3-phosphoinositides |
| 219398_at | zinc finger protein 338 |
| 219472_at | matrix metalloproteinase 28 |
| 219508_at | glucosaminyl (N-acetyl) transferase 3, mucin type |
| 219677_at | UDP-glucuronate decarboxylase 1 |
| 219679_s_at | gb: NM_018604.1 /DEF = *Homo sapiens* hypothetical protein PRO1741 (PRO1741), mRNA. /FEA = mRNA /GEN = PRO1741 /PROD = hypothetical protein PRO1741 /DB_XREF = gi: 8924074 /UG = Hs.306067 hypothetical protein PRO . . . |
| 219702_at | placenta-specific 1 |
| 219860_at | chromosome 6 open reading frame 20 |
| 219910_at | coronin, actin binding protein, 1A |
| 219977_at | aryl hydrocarbon receptor interacting protein-like 1 |
| 220071_x_at | fidgetin |
| 220113_x_at | lysyl oxidase-like 4 |
| 220115_s_at | gb: NM_006727.1 /DEF = *Homo sapiens* cadherin 10, type 2 (T2-cadherin) (CDH10), mRNA. /FEA = mRNA /GEN = CDH10 /PROD = cadherin 10, type 2 (T2-cadherin) /DB_XREF = gi: 5802995 /UG = Hs.92489 cadherin 10, type 2 . . . |
| 220232_at | chromosome 20 open reading frame 39 |
| 220252_x_at | optic atrophy 3 (autosomal recessive, with chorea and spastic paraplegia) |
| 220287_at | a disintegrin-like and metalloprotease (reprolysin type) with thrombospondin type 1 motif, 9 |
| 220352_x_at | gb: NM_024305.1 /DEF = *Homo sapiens* hypothetical protein MGC4278 (MGC4278), mRNA. /FEA = mRNA /GEN = MGC4278 /PROD = hypothetical protein MGC4278 /DB_XREF = gi: 13236535 /UG = Hs.318780 hypothetical protein MG . . . |
| 220398_at | matrix metalloproteinase 28 |
| 220446_s_at | carbohydrate (N-acetylglucosamine 6-O) sulfotransferase 4 |

TABLE 3-continued genes down-regulated at day 2

| Gene Name | Gene Description |
|---|---|
| 220452_x_at | gb: NM_021031.1 /DEF = *Homo sapiens* cytochrome c-like antigen (CYCL), mRNA. /FEA = mRNA /GEN = CYCL /PROD = cytochrome c-like antigen /DB_XREF = gi: 10518341 /UG = Hs.262219 cytochrome c-like antigen /FL = gb: NM . . . |
| 220560_at | chromosome 11 open reading frame 21 |
| 220574_at | chromosome 20 open reading frame 48 |
| 220591_s_at | optic atrophy 3 (autosomal recessive, with chorea and spastic paraplegia) |
| 220671_at | CCR4 carbon catabolite repression 4-like (*S. cerevisiae*) |
| 220684_at | T-box 21 |
| 220720_x_at | tubulin, alpha 4 |
| 220725_x_at | UDP-glucuronate decarboxylase 1 |
| 220776_at | potassium inwardly-rectifying channel, subfamily J, member 14 |
| 220796_x_at | brain and acute leukemia, cytoplasmic |
| 220800_s_at | tropomodulin 3 (ubiquitous) |
| 220833_at | myosin XVA |
| 220838_at | chromosome 20 open reading frame 21 |
| 220853_at | Kruppel-like factor 15 |
| 220944_at | RAB25, member RAS oncogene family |
| 221078_s_at | LUC7-like (*S. cerevisiae*) |
| 221107_at | cholinergic receptor, nicotinic, alpha polypeptide 9 |
| 221155_x_at | DnaJ (Hsp40) homolog, subfamily A, member 4 |
| 221192_x_at | matrix metalloproteinase 28 |
| 221220_s_at | hypoxia-inducible factor 1, alpha subunit inhibitor |
| 221419_s_at | gb: NM_013307.1 /DEF = *Homo sapiens* non-functional folate binding protein (HSAF000381), mRNA. /FEA = CDS /GEN = HSAF000381 /PROD = non-functional folate binding protein /DB_XREF = gi: 7019412 /FL = gb: NM_013307.1 |
| 221443_x_at | protease inhibitor 15 |
| 221460_at | olfactory receptor, family 2, subfamily C, member 1 |
| 221473_x_at | tumor differentially expressed 1 |
| 221541_at | espin |
| 221695_s_at | mitogen-activated protein kinase kinase kinase 2 [BLAST] |
| 221717_at | G protein-coupled receptor 52 |
| 221757_at | chromosome 20 open reading frame 54 |
| 221832_s_at | cysteine and tyrosine-rich 1 [BLAST] |
| 221917_s_at | G-rich RNA sequence binding factor 1 |
| 221997_s_at | Ca<2+>dependent activator protein for secretion [BLAST] |
| 222252_x_at | chromosome 1 open reading frame 6 |
| 222368_at | Consensus includes gb: AW972351 /FEA = EST /DB_XREF = gi: 8162197 /DB_XREF = est: EST384442 /UG = Hs.293451 ESTs |
| 222370_x_at | RAS, guanyl releasing protein 4 |

TABLE 4 genes down-regulated at day 5

| Gene Name | Gene Description |
|---|---|
| 1316_at | thyroid hormone receptor, alpha (erythroblastic leukemia viral (v-erb-a) oncogene homolog, avian) |
| 35150_at | tumor necrosis factor receptor superfamily, member 5 |
| 36829_at | period homolog 1 (*Drosophila*) |
| 37793_r_at | RAD51-like 3 (*S. cerevisiae*) |
| 47571_at | zinc finger protein 236 |
| 49327_at | sirtuin silent mating type information regulation 2 homolog 3 (*S. cerevisiae*) |
| 48612_at | tubulin, beta polypeptide 4, member Q |
| 58900_at | Kruppel-like factor 13 |
| 200706_s_at | fragile X mental retardation, autosomal homolog 2 |
| 200776_s_at | syndecan 3 (N-syndecan) |
| 200915_x_at | kinectin 1 (kinesin receptor) |
| 200976_s_at | Tax1 (human T-cell leukemia virus type I) binding protein 1 |
| 201041_s_at | dual specificity phosphatase 1 |
| 201044_x_at | dual specificity phosphatase 1 |
| 201057_s_at | golgi autoantigen, golgin subfamily b, macrogolgin (with transmembrane signal), 1 |
| 201070_x_at | splicing factor 3b, subunit 1, 155 kD |
| 201140_s_at | RAB5C, member RAS oncogene family |
| 201278_at | disabled homolog 2, mitogen-responsive phosphoprotein (*Drosophila*) |

TABLE 4-continued genes down-regulated at day 5

| Gene Name | Gene Description |
|---|---|
| 201502_s_at | nuclear factor of kappa light polypeptide gene enhancer in B-cells inhibitor, alpha |
| 201567_s_at | golgi autoantigen, golgin subfamily a, 4 |
| 201686_x_at | apoptosis inhibitor 5 |
| 201876_at | paraoxonase 2 |
| 201878_at | ariadne homolog, ubiquitin-conjugating enzyme E2 binding protein, 1 (*Drosophila*) |
| 201884_at | carcinoembryonic antigen-related cell adhesion molecule 5 |
| 201971_s_at | ATPase, H+ transporting, lysosomal 70 kD, V1 subunit A, isoform 1 |
| 202037_s_at | secreted frizzled-related protein 1 |
| 202071_at | syndecan 4 (amphiglycan, ryudocan) |
| 202122_s_at | glycoprotein A33 (transmembrane) |
| 202224_at | Consensus includes gb: BF304695 /FEA = EST /DB_XREF = gi: 11251580 /DB_XREF = est: 601888248F1 /CLONE = IMAGE: 4122466 /UG = Hs.306088 v-crk avian sarcoma virus CT10 oncogene homolog /FL = gb: D10656.1 gb: NM_016823.1 |
| 202488_s_at | FXYD domain-containing ion transport regulator 3 |
| 202604_x_at | a disintegrin and metalloproteinase domain 10 |
| 202709_at | fibromodulin |
| 202840_at | gb: NM_003487.1 /DEF = *Homo sapiens* TATA box binding protein (TBP)-associated factor, RNA polymerase II, N, 68 kD (RNA-binding protein 56) (TAF2N), mRNA. /FEA = mRNA /GEN = TAF2N /PROD = TATA box binding . . . |
| 202861_at | period homolog 1 (*Drosophila*) |
| 202873_at | ATPase, H+ transporting, lysosomal 42 kD, V1 subunit C, isoform 1 |
| 202902_s_at | cathepsin S |
| 202921_s_at | ankyrin 2, neuronal |
| 203134_at | phosphatidylinositol binding clathrin assembly protein |
| 203243_s_at | transducin (beta)-like 3 |
| 203319_s_at | zinc finger protein 148 (pHZ-52) |
| 203395_s_at | hairy homolog (*Drosophila*) |
| 203511_s_at | potassium large conductance calcium-activated channel, subfamily M beta member 3 |
| 203512_at | potassium large conductance calcium-activated channel, subfamily M beta member 3 |
| 203666_at | stromal cell-derived factor 1 |
| 203758_at | cathepsin O |
| 203788_s_at | sema domain, immunoglobulin domain (Ig), short basic domain, secreted, (semaphorin) 3C |
| 203887_s_at | thrombomodulin |
| 203922_s_at | cytochrome b-245, beta polypeptide (chronic granulomatous disease) |
| 203933_at | sema domain, immunoglobulin domain (Ig), short basic domain, secreted, (semaphorin) 3E |
| 203963_at | carbonic anhydrase XII |
| 204042_at | WAS protein family, member 3 |
| 204230_s_at | solute carrier family 17 (sodium-dependent inorganic phosphate cotransporter), member 7 |
| 204232_at | Fc fragment of IgE, high affinity I, receptor for; gamma polypeptide |
| 204243_at | rearranged L-myc fusion sequence |
| 204312_x_at | cAMP responsive element binding protein 1 |
| 204360_s_at | N-acetylglucosaminidase, alpha-(Sanfilippo disease IIIB) |
| 204421_s_at | gb: M27968.1 /DEF = Human basic fibroblast growth factor (FGF) mRNA, complete cds. /FEA = mRNA /GEN = FGF2 /DB_XREF = gi: 182562 /UG = Hs.284244 fibroblast growth factor 2 (basic) /FL = gb: M27968.1 gb: NM_002006.1 |
| 204670_x_at | major histocompatibility complex, class II, DR beta 1 |
| 204762_s_at | guanine nucleotide binding protein (G protein), alpha activating activity polypeptide O |
| 204802_at | Ras-related associated with diabetes |
| 204842_x_at | sperm autoantigenic protein 17 |
| 205046_at | centromere protein E (312 kD) |
| 205097_at | solute carrier family 26 (sulfate transporter), member 2 |
| 205232_s_at | platelet-activating factor acetylhydrolase 2 (40 kD) |
| 205235_s_at | M-phase phosphoprotein 1 |
| 205328_at | claudin 10 |
| 205359_at | A kinase (PRKA) anchor protein 6 |
| 205381_at | mesothelin |
| 205431_s_at | bone morphogenetic protein 5 |
| 205520_at | striatin, calmodulin binding protein |
| 205525_at | gb: NM_018495.3 /DEF = *Homo sapiens* NAG22 protein (LOC55873), mRNA. /FEA = mRNA /GEN = LOC55873 /PROD = NAG22 protein |

TABLE 4-continued genes down-regulated at day 5

| Gene Name | Gene Description |
|---|---|
| | /DB_XREF = gi: 13236500 /UG = Hs.283080 NAG22 protein /FL = gb: AF247820.3 gb: NM_018495.3 |
| 205595_at | desmoglein 3 (pemphigus vulgaris antigen) |
| 205608_s_at | angiopoietin 1 |
| 205636_at | SH3-domain GRB2-like 3 [BLAST] |
| 205729_at | oncostatin M receptor |
| 205752_s_at | glutathione S-transferase M5 |
| 205879_x_at | ret proto-oncogene (multiple endocrine neoplasia and medullary thyroid carcinoma 1, Hirschsprung disease) |
| 206096_at | zinc finger protein 35 (clone HF.10) |
| 206212_at | carboxypeptidase A2 (pancreatic) |
| 206263_at | flavin containing monooxygenase 4 |
| 206291_at | neurotensin |
| 206388_at | phosphodiesterase 3A, cGMP-inhibited |
| 206389_s_at | phosphodiesterase 3A, cGMP-inhibited |
| 206456_at | gamma-aminobutyric acid (GABA) A receptor, alpha 5 |
| 206586_at | cannabinoid receptor 2 (macrophage) |
| 206766_at | integrin, alpha 10 |
| 206825_at | oxytocin receptor |
| 206910_x_at | H factor (complement)-like 3 |
| 206936_x_at | chromosome 20 open reading frame 110 |
| 207041_at | mannan-binding lectin serine protease 2 |
| 207064_s_at | amine oxidase, copper containing 2 (retina-specific) |
| 207131_x_at | gamma-glutamyltransferase 1 |
| 207347_at | excision repair cross-complementing rodent repair deficiency, complementation group 6 |
| 207408_at | organic cationic transporter-like 4 |
| 207608_x_at | cytochrome P450, subfamily I (aromatic compound-inducible), polypeptide 2 |
| 207732_s_at | discs, large (*Drosophila*) homolog 3 (neuroendocrine-dlg) |
| 207755_at | chromosome 20 open reading frame 48 |
| 207908_at | keratin 2A (epidermal ichthyosis bullosa of Siemens) |
| 207936_x_at | ret finger protein-like 3 |
| 207938_at | protease inhibitor 15 |
| 207969_x_at | acrosomal vesicle protein 1 [BLAST] |
| 208124_s_at | sema domain, immunoglobulin domain (Ig), transmembrane domain (TM) and short cytoplasmic domain, (semaphorin) 4F |
| 208138_at | gastrin |
| 208185_x_at | Consensus includes gb: NM_016415.1 /DEF = *Homo sapiens* clone FLB3816 (LOC51216), mRNA. /FEA = mRNA /GEN = LOC51216 /PROD = clone FLB3816 /DB_XREF = gi: 10047109 /UG = Hs.277887 clone FLB3816 /FL = gb: NM_016415.1 . . . |
| 208351_s_at | mitogen-activated protein kinase 1 |
| 208360_s_at | gb: NM_015870.1 /DEF = *Homo sapiens* endogenous retrovirus H D1 leader regionintegrase-derived ORF1, ORF2, and putative envelope protein (HSU88895), mRNA. /FEA = mRNA /GEN = HSU88895 /PROD = endogenous re . . . |
| 208382_s_at | DMC1 dosage suppressor of mck1 homolog, meiosis-specific homologous recombination (yeast) |
| 208447_s_at | phosphoribosyl pyrophosphate synthetase 1 |
| 208486_at | cytochrome P450, subfamily IVA, polypeptide 11 [BLAST] |
| 208679_s_at | actin related protein 2/3 complex, subunit 2 (34 kD) |
| 208730_x_at | RAB2, member RAS oncogene family |
| 208763_s_at | delta sleep inducing peptide, immunoreactor |
| 208860_s_at | alpha thalassemia/mental retardation syndrome X-linked (RAD54 homolog, *S. cerevisiae*) |
| 208868_s_at | GABA(A) receptor-associated protein like 1 |
| 208869_s_at | GABA(A) receptor-associated protein like 1 |
| 208937_s_at | inhibitor of DNA binding 1, dominant negative helix-loop-helix protein |
| 209312_x_at | gb: U65585.1 /DEF = *Homo sapiens* MHC class II antigen (HLA-DRB1) mRNA, HLA-DRB1*PBL allele, complete cds. /FEA = mRNA /GEN = HLA-DRB1 /PROD = MHC class II antigen /DB_XREF = gi: 5478215 /UG = Hs.180255 major . . . |
| 209436_at | spondin 1, (f-spondin) extracellular matrix protein |
| 209535_s_at | LIM and SH3 protein 1 |
| 209701_at | desmin [BLAST] |
| 209703_x_at | component of oligomeric golgi complex 4 |
| 209790_s_at | caspase 6, apoptosis-related cysteine protease [BLAST] |
| 209882_at | Ric-like, expressed in many tissues (*Drosophila*) |
| 210048_at | N-ethylmaleimide-sensitive factor attachment protein, gamma |
| 210191_s_at | putative homeodomain transcription factor 1 |
| 210226_at | nuclear receptor subfamily 4, group A, member 1 |
| 210412_at | glutamate receptor, ionotropic, N-methyl D-aspartate 2B |

TABLE 4-continued genes down-regulated at day 5

| Gene Name | Gene Description |
|---|---|
| 210639_s_at | APG5 autophagy 5-like (*S. cerevisiae*) |
| 210739_x_at | solute carrier family 4, sodium bicarbonate cotransporter, member 4 |
| 210757_x_at | disabled homolog 2, mitogen-responsive phosphoprotein (*Drosophila*) |
| 210796_x_at | sialic acid binding Ig-like lectin 6 |
| 210830_s_at | paraoxonase 2 |
| 210836_x_at | phosphodiesterase 4D, cAMP-specific (phosphodiesterase E3 dunce homolog, *Drosophila*) |
| 210837_s_at | phosphodiesterase 4D, cAMP-specific (phosphodiesterase E3 dunce homolog, *Drosophila*) |
| 210912_x_at | glutathione S-transferase M4 |
| 210923_at | chromosome 20 open reading frame 82 |
| 210944_s_at | calpain 3, (p94) |
| 210962_s_at | A kinase (PRKA) anchor protein (yotiao) 9 |
| 211014_s_at | promyelocytic leukemia |
| 211026_s_at | monoglyceride lipase [BLAST] |
| 211040_x_at | gb: BC006325.1 /DEF = *Homo sapiens*, G-2 and S-phase expressed 1, clone MGC: 12560, mRNA, complete cds. /FEA = mRNA /PROD = G-2 and S-phase expressed 1 /DB_XREF = gi: 13623450 /FL = gb: BC006325.1 |
| 211071_s_at | chromosome 12 open reading frame 8 [BLAST] |
| 211074_at | gb: AF000381.1 /DEF = *Homo sapiens* non-functional folate binding protein mRNA, complete cds. /FEA = mRNA /PROD = non-functional folate binding protein /DB_XREF = gi: 2565195 /FL = gb: AF000381.1 |
| 211096_at | pre-B-cell leukemia transcription factor 2 |
| 211113_s_at | ATP-binding cassette, sub-family G (WHITE), member 1 |
| 211139_s_at | NGFI-A binding protein 1 (EGR1 binding protein 1) |
| 211277_x_at | amyloid beta (A4) precursor protein (protease nexin-II, Alzheimer disease) |
| 211316_x_at | CASP8 and FADD-like apoptosis regulator |
| 211328_x_at | hemochromatosis |
| 211364_at | methylthioadenosine phosphorylase |
| 211416_x_at | gamma-glutamyltransferase 1 |
| 211460_at | testis-specific transcript, Y-linked 9 |
| 211464_x_at | caspase 6, apoptosis-related cysteine protease |
| 211504_x_at | Rho-associated, coiled-coil containing protein kinase 2 |
| 211574_s_at | membrane cofactor protein (CD46, trophoblast-lymphocyte cross-reactive antigen) |
| 211657_at | carcinoembryonic antigen-related cell adhesion molecule 6 (non-specific cross reacting antigen) [BLAST] |
| 211685_s_at | neurocalcin delta [BLAST] |
| 211713_x_at | histone deacetylase 4 [BLAST] |
| 211769_x_at | tumor differentially expressed 1 [BLAST] |
| 211781_x_at | gb: BC006164.1 /DEF = *Homo sapiens*, clone MGC: 13219, mRNA, complete cds. /FEA = mRNA /PROD = Unknown (protein for MGC: 13219) /DB_XREF = gi: 13544062 /FL = gb: BC006164.1 |
| 211801_x_at | hypoxia-inducible factor 1, alpha subunit inhibitor |
| 211810_s_at | galactosylceramidase (Krabbe disease) |
| 211814_s_at | cyclin E2 |
| 211918_x_at | placenta-specific 3 [BLAST] |
| 212196_at | tumor necrosis factor receptor superfamily, member 19-like [BLAST] |
| 212233_at | chromosome 1 open reading frame 2 |
| 212514_x_at | Consensus includes gb: R60068 /FEA = EST /DB_XREF = gi: 830763 /DB_XREF = est: yh12h07.s1 /CLONE = IMAGE: 43138 /UG = Hs.147916 DEADH (Asp-Glu-Ala-AspHis) box polypeptide 3 |
| 212736_at | Consensus includes gb: BE299456 /FEA = EST /DB_XREF = gi: 9183204 /DB_XREF = est: 600944717T1 /CLONE = IMAGE: 2960548 /UG = Hs.6349 Human Chromosome 16 BAC clone CIT987SK-A-362G6 |
| 212876_at | UDP-Gal: betaGlcNAc beta 1,4-galactosyltransferase, polypeptide 4 |
| 212884_x_at | apolipoprotein E [BLAST] |
| 213139_at | snail homolog 2 (*Drosophila*) |
| 213193_x_at | T cell receptor beta locus |
| 213297_at | nucleolar protein family A, member 2 (H/ACA small nucleolar RNPs) |
| 213307_at | Consensus includes gb: AF131790.1 /DEF = *Homo sapiens* clone 24903 mRNA sequence. /FEA = mRNA /DB_XREF = gi: 4406618 /UG = Hs.12696 cortactin SH3 domain-binding protein |
| 213406_at | golgi associated, gamma adaptin ear containing, ARF binding protein 1 |
| 213486_at | retinoic acid induced 17 [BLAST] |
| 213816_s_at | met proto-oncogene (hepatocyte growth factor receptor) |
| 213936_x_at | surfactant, pulmonary-associated protein B |
| 214007_s_at | protein tyrosine kinase 9 [BLAST] |

TABLE 4-continued genes down-regulated at day 5

| Gene Name | Gene Description |
|---|---|
| 214336_s_at | coatomer protein complex, subunit alpha |
| 214421_x_at | cytochrome P450, subfamily IIC (mephenytoin 4-hydroxylase), polypeptide 9 [BLAST] |
| 214656_x_at | myosin IC |
| 214698_at | Consensus includes gb: AW190873 /FFA = EST /DB_XREF = gi: 6465353 /DB_XREF = est: x166a01.x1 /CLONE = IMAGE: 2679624 /UG = Hs.145078 regulator of differentiation (in S. pombe) 1 |
| 214720_x_at | Consensus includes gb: BF981643 /FEA = EST /DB_XREF = gi: 12384455 /DB_XREF = est: 602305961F1 /CLONE = IMAGE: 4397295 /UG = Hs.79844 DKFZP564M1416 protein |
| 214849_at | Consensus includes gb: AW500220 /FEA = EST /DB_XREF = gi: 7112628 /DB_XREF = est: UI-HF-BN0-akd-c-02-0-UI.r1 /CLONE = IMAGE: 3076610 /UG = Hs.332496 Human DNA sequence from clone 108K11 on chromosome 6p21 Cont . . . |
| 214906_x_at | ATPase, H+ transporting, lysosomal 31 kD, V1 subunit E isoform 2 |
| 214923_at | Consensus includes gb: AK001155.1 /DEF = *Homo sapiens* cDNA FLJ10293 fis, clone NT2RM1000280, highly similar to VACUOLAR ATP SYNTHASE SUBUNIT D (EC 3.6.1.34). /FEA = mRNA /DB_XREF = gi: 7022230 /UG = Hs.30 . . . |
| 214933_at | calcium channel, voltage-dependent, P/Q type, alpha 1A subunit |
| 214951_at | UDP-N-acetyl-alpha-D-galactosamine: (N-acetylneuraminyl)-galactosylglucosylceramide N-acetylgalactosaminyltransferase (GalNAc-T) |
| 214953_s_at | amyloid beta (A4) precursor protein (protease nexin-II, Alzheimer disease) |
| 215032_at | nudix (nucleoside diphosphate linked moiety X)-type motif 11 |
| 215178_x_at | N-acylsphingosine amidohydrolase (acid ceramidase)-like |
| 215236_s_at | phosphatidylinositol binding clathrin assembly protein |
| 215366_at | sorting nexin 6 |
| 215439_x_at | F-box and leucine-rich repeat protein 11 |
| 215479_at | immunoglobulin superfamily, member 9 [BLAST] |
| 215588_x_at | Consensus includes gb: AK024958.1 /DEF = *Homo sapiens* cDNA: FLJ21305 fis, clone COL02124. /FEA = mRNA /DB_XREF = gi: 10437382 /UG = Hs.287658 *Homo sapiens* cDNA: FLJ21305 fis, clone COL02124 |
| 215609_at | Consensus includes gb: AK023895.1 /DEF = *Homo sapiens* cDNA FLJ13833 fis, clone THYRO1000676. /FEA = mRNA /DB_XREF = gi: 10435969 /UG = Hs.296745 *Homo sapiens* cDNA FLJ13833 fis, clone THYRO1000676 |
| 215758_x_at | zinc finger protein 253 |
| 215766_at | Consensus includes gb: AL096729.1 /DEF = *Homo sapiens* mRNA; cDNA DKFZp434D044 (from clone DKFZp434D044). /FEA = mRNA /DB_XREF = gi: 5419863 /UG = Hs.146581 *Homo sapiens* mRNA; cDNA DKFZp434D044 (from clone . . . |
| 215825_at | Consensus includes gb: AF070579.1 /DEF = *Homo sapiens* clone 24487 mRNA sequence. /FEA = mRNA /DB_XREF = gi: 3387951 /UG = Hs.283819 *Homo sapiens* clone 24487 mRNA sequence |
| 215856_at | Consensus includes gb: AK025833.1 /DEF = *Homo sapiens* cDNA: FLJ22180 fis, clone HRC00936. /FEA = mRNA /DB_XREF = gi: 10438467 /UG = Hs.287692 *Homo sapiens* cDNA: FLJ22180 fis, clone HRC00936 |
| 215910_s_at | carbohydrate (chondroitin) synthase 1 |
| 216061_x_at | platelet-derived growth factor beta polypeptide (simian sarcoma viral (v-sis) oncogene homolog) |
| 216159_s_at | prostate tumor over expressed gene 1 |
| 216196_at | chromosome 20 open reading frame 136 [BLAST] |
| 216220_s_at | adenosine A1 receptor |
| 216292_at | Consensus includes gb: AK024455.1 /DEF = *Homo sapiens* mRNA for FLJ00047 protein, partial cds. /FEA = mRNA /GEN = FLJ00047 /PROD = FLJ00047 protein /DB_XREF = gi: 10440423 /UG = Hs.287753 *Homo sapiens* mRNA for . . . |
| 216294_s_at | ubiquitin specific protease 24 |
| 216374_at | Consensus includes gb: AC006986 /DEF = *Homo sapiens* BAC clone RP11-155J5 from Y /FEA = CDS /DB_XREF = gi: 4753246 /UG = Hs.283908 *Homo sapiens* BAC clone RP11-155J5 from Y |
| 216661_x_at | cytochrome P450, subfamily IIC (mephenytoin 4-hydroxylase), polypeptide 9 |
| 216735_x_at | prostate tumor over expressed gene 1 [BLAST] |
| 216745_x_at | Consensus includes gb: AK024606.1 /DEF = *Homo sapiens* cDNA: FLJ20953 fis, clone ADSE01979. /FEA = mRNA /DB_XREF = gi: 10436920 /UG = Hs.306697 *Homo sapiens* cDNA: FLJ20953 fis, clone ADSE01979 |
| 216791_at | lysyl oxidase-like 4 [BLAST] |

TABLE 4-continued genes down-regulated at day 5

| Gene Name | Gene Description |
|---|---|
| 216859_x_at | Consensus includes gb: AL080112.1 /DEF = *Homo sapiens* mRNA; cDNA DKFZp586H0722 (from clone DKFZp586H0722). /FEA = mRNA /DB_XREF = gi: 5262539 /UG = Hs.332731 *Homo sapiens* mRNA; cDNA DKFZp586H0722 (from clo . . . |
| 216873_s_at | ATPase, Class I, type 8B, member 2 |
| 216936_at | Consensus includes gb: X81637.1 /DEF = *H. sapiens* clathrin light chain b gene. /FEA = mRNA /DB_XREF = gi: 963046 /UG = Hs.73919 clathrin, light polypeptide (Lcb) |
| 216993_s_at | Consensus includes gb: U32169 /DEF = Human pro-a2 chain of collagen type XI (COL11A2) gene, complete cds /FEA = mRNA_3 /DB_XREF = gi: 1000744 /UG = Hs.121509 collagen, type XI, alpha 2 |
| 217020_at | retinoic acid receptor, beta |
| 217117_x_at | Consensus includes gb: AF007194.1 /DEF = *Homo sapiens* mucin (MUC3) mRNA, partial cds. /FEA = mRNA /GEN = MUC3 /PROD = mucin /DB_XREF = gi: 2853300 /UG = Hs.129782 mucin 3A, intestinal |
| 217189_s_at | chromosome 1 open reading frame 16 |
| 217269_s_at | protease, serine, 7 (enterokinase) |
| 217315_s_at | kallikrein 13 |
| 217377_x_at | ets variant gene 6 (TEL oncogene) |
| 217457_s_at | RAP1, GTP-GDP dissociation stimulator 1 |
| 217465_at | NCK-associated protein 1 [BLAST] |
| 217480_x_at | G protein-coupled receptor 2 |
| 217703_x_at | Consensus includes gb: AA401963 /FEA = EST /DB_XREF = gi: 2055965 /DB_XREF = est: zu53c08.s1 /CLONE = IMAGE: 741710 /UG = Hs.194107 ESTs, Moderately similar to ALU7_HUMAN ALU SUBFAMILY SQ SEQUENCE CONTAMINATIO . . . |
| 217787_s_at | UDP-N-acetyl-alpha-D-galactosamine: polypeptide N-acetylgalactosaminyltransferase 2 (GalNAc-T2) |
| 217859_s_at | synaptojanin 2 binding protein |
| 217862_at | protein inhibitor of activated STAT, 1 |
| 217878_s_at | Consensus includes gb: AI203880 /FEA = EST /DB_XREF = gi: 3756486 /DB_XREF = est: qf77g07.x1 /CLONE = IMAGE: 1756092 /UG = Hs.172405 cell division cycle 27 /FL = gb: NM_001256.1 |
| 218211_s_at | transgene insertion 202, William Muller |
| 218554_s_at | solute carrier family 22 (organic anion/cation transporter), member 11 |
| 218949_s_at | chromosome 15 open reading frame 12 |
| 219014_at | toll-like receptor 8 |
| 219032_x_at | opsin 3 (encephalopsin, panopsin) |
| 219183_s_at | pleckstrin homology, Sec7 and coiled/coil domains 4 |
| 219194_at | sema domain, immunoglobulin domain (Ig), transmembrane domain (TM) and short cytoplasmic domain, (semaphorin) 4G |
| 219221_at | engulfment and cell motility 3 (ced-12 homolog, *C. elegans*) |
| 219228_at | chromosome Y open reading frame 14 |
| 219398_at | zinc finger protein 338 |
| 219472_at | matrix metalloproteinase 28 |
| 219677_at | UDP-glucuronate decarboxylase 1 |
| 219679_s_at | gb: NM_018604.1 /DEF = *Homo sapiens* hypothetical protein PRO1741 (PRO1741), mRNA. /FEA = mRNA /GEN = PRO1741 /PROD = hypothetical protein PRO1741 /DB_XREF = gi: 8924074 /UG = Hs.306067 hypothetical protein PRO . . . |
| 219702_at | placenta-specific 1 |
| 219757_s_at | chromosome 20 open reading frame 21 |
| 219860_at | chromosome 6 open reading frame 20 |
| 219910_at | coronin, actin binding protein, 1A |
| 219977_at | aryl hydrocarbon receptor interacting protein-like 1 |
| 220115_s_at | gb: NM_006727.1 /DEF = *Homo sapiens* cadherin 10, type 2 (T2-cadherin) (CDH10), mRNA. /FEA = mRNA /GEN = CDH10 /PROD = cadherin 10, type 2 (T2-cadherin) /DB_XREF = gi: 5802995 /UG = Hs.92489 cadherin 10, type 2 . . . |
| 220287_at | a disintegrin-like and metalloprotease (reprolysin type) with thrombospondin type 1 motif, 9 |
| 220398_at | matrix metalloproteinase 28 |
| 220446_s_at | carbohydrate (N-acetylglucosamine 6-O) sulfotransferase 4 |
| 220560_at | chromosome 11 open reading frame 21 |
| 220574_at | chromosome 20 open reading frame 48 |
| 220725_x_at | UDP-glucuronate decarboxylase 1 |
| 220776_at | potassium inwardly-rectifying channel, subfamily J, member 14 |
| 220800_s_at | tropomodulin 3 (ubiquitous) |
| 220833_at | myosin XVA |
| 220838_at | chromosome 20 open reading frame 21 |
| 220853_at | Kruppel-like factor 15 |
| 220944_at | RAB25, member RAS oncogene family |
| 221078_s_at | LUC7-like (*S. cerevisiae*) |
| 221107_at | cholinergic receptor, nicotinic, alpha polypeptide 9 |

TABLE 4-continued genes down-regulated at day 5

| Gene Name | Gene Description |
| --- | --- |
| 221220_s_at | hypoxia-inducible factor 1, alpha subunit inhibitor |
| 221460_at | olfactory receptor, family 2, subfamily C, member 1 |
| 221473_x_at | tumor differentially expressed 1 |
| 221541_at | espin |
| 221695_s_at | mitogen-activated protein kinase kinase kinase 2 [BLAST] |
| 221717_at | G protein-coupled receptor 52 |
| 221757_at | chromosome 20 open reading frame 54 |
| 221832_s_at | cysteine and tyrosine-rich 1 [BLAST] |
| 221917_s_at | G-rich RNA sequence binding factor 1 |
| 221997_s_at | Ca$<$2+$>$dependent activator protein for secretion [BLAST] |
| 222368_at | Consensus includes gb: AW972351 /FEA = EST /DB_XREF = gi: 8162197 /DB_XREF = est: EST384442 /UG = Hs.293451 ESTs |
| 222370_x_at | RAS, guanyl releasing protein 4 |

The invention claimed is:

1. A method of treating a subject suffering from a cancer selected from the group consisting of breast cancer and liver cancer, the method comprising:
    (i) preparing a pharmaceutical composition by a method comprising
        (a) comminuting rhizomes of *Fagopyrum dibotrys*;
        (b) extracting the comminuted material with a solvent comprising a $C_1$-$C_4$ alcohol to produce a liquid extract; and
        (c) removing solvent from the liquid extract to produce a dried or concentrated material; and optionally
        (d) fractionating the dried or concentrated material; and
    (ii) administering the pharmaceutical composition to the subject.

2. A method according to claim 1 wherein the solvent comprises ethanol.

3. A method according to claim 1 wherein an excipient is added to the liquid extract and step (c) comprises drying under reduced pressure to produce a dry material.

4. The method according to claim 1 wherein the cancer is breast cancer.

5. The method according to claim 1 wherein the cancer is liver cancer.

* * * * *